(12) United States Patent
Schwab et al.

(10) Patent No.: US 7,425,334 B2
(45) Date of Patent: Sep. 16, 2008

(54) METHODS OF MAKING ANTIBODIES THAT BIND NOGO

(75) Inventors: Martin E. Schwab, Zurich (CH); Maio S. Chen, Zurich (CH)

(73) Assignee: The University of Zurich (CH)

( * ) Notice: Subject to any disclaimer, the term of this patent is extended or adjusted under 35 U.S.C. 154(b) by 0 days.

(21) Appl. No.: 11/044,899

(22) Filed: Jan. 26, 2005

(65) Prior Publication Data

US 2005/0260616 A1 Nov. 24, 2005

Related U.S. Application Data

(63) Continuation of application No. 09/830,972, filed as application No. PCT/US99/26160 on Nov. 5, 1999.

(60) Provisional application No. 60/107,446, filed on Nov. 6, 1998.

(51) Int. Cl.
*A61K 39/00* (2006.01)
*A61K 38/18* (2006.01)

(52) U.S. Cl. ..................... 424/185.1; 514/12

(58) Field of Classification Search ............ None
See application file for complete search history.

(56) References Cited

U.S. PATENT DOCUMENTS

| 4,196,265 | A | * | 4/1980 | Koprowski et al. ....... 435/70.21 |
|---|---|---|---|---|
| 5,250,414 | A | | 10/1993 | Schwab et al. |
| 5,684,133 | A | | 11/1997 | Schwab et al. |
| 6,103,232 | A | | 8/2000 | Schwab et al. |
| 2002/0010324 | A1 | | 1/2002 | Michalovich et al. |
| 2002/0072493 | A1 | | 6/2002 | Schwartz et al. |

FOREIGN PATENT DOCUMENTS

| EP | 046 523 A1 | | 3/1982 |
|---|---|---|---|
| EP | 155 433 A1 | | 9/1985 |
| EP | 159 289 A1 | | 10/1985 |
| EP | 233 838 A2 | | 8/1987 |
| WO | WO 90/05191 | | 5/1990 |
| WO | WO 93/00427 | | 1/1993 |
| WO | WO 98/06841 | | 2/1998 |
| WO | 98/17687 | * | 4/1998 |
| WO | WO 98/17687 | | 4/1998 |
| WO | WO 00/05364 | | 2/2000 |
| WO | 00/11015 | * | 3/2000 |
| WO | WO 00/31235 | | 6/2000 |
| WO | WO 01/36631 | * | 5/2001 |

OTHER PUBLICATIONS

Schwab et al. 1991. Journal of Neuroscience 11(3):709-721.*
Harlow 1988. Antibodies: A Laboratory Manual, pp. 23-35 and 53-60.*
U.S. Appl. No. 2003/0134301.*
Geysen et al. 1988. Journal of Molecular Recognition 1:32-41.*
Ex parte Kubin, Board of Patent Appeals and Interferences, 2007-0819.*
U.S. Appl. No. 10/624,626, filed Jan. 1, 2001, Michalovich et al.
U.S. Appl. No. 10/172,329, filed Jun. 14, 2002, Michalovich et al.
U.S. Appl. No. 09/359,208, filed Jul. 22, 1999, Michalovich et al.
Aguayo et al., Ensheathment and myelination of regenerating PNS fibres by transplanted optic nerve glia. 1978, Neurosci. Lett. 9: 97-104.
Almenoff and Orlowski, Membrane-bound kidney neutral metalloendopeptidase: interaction with synthetic substrates, natural peptides, and inhibitors. Biochemistry. Feb 1, 1983;22(3):590-599.
Amberger et al., Can rat Glioblastoma cells use a specific proteolytic mechanism to overcome the inhibitory substrate effect of CNS white matter for invasive cell migration? Experientia. 1991; 47, A2.
Bandtlow et al., Brain macrophage migration in CNS tissue in vitro, involvement of a metalloprotease. Experientia, 1989, 45(Abstr.): A30.
Bandtlow et al. The *Escherichia coli*-derived Fab fragment of the IgM/kappa antibody IN-I recognizes and neutralizes myelin-associated inhibitors of neurite growth. Eur J Biochem. Oct. 15, 1996;241(2):468-475.
Bandtlow et al., Cellular localization of nerve growth factor synthesis by in situ hybridization. Soc. Neurosci. Abstr. 1987, 13:1616.
Bandtlow et al. Role of intracellular calcium in NI-35-evoked collapse of neuronal growth cones. Science. Jan. 1, 1993;259(5091):80-83.
Bandtlow et al., Can myelin neurite growth inhibitor protein causes collapse and retraction of rat DRG growth cones by changes in intracellular calcium. Experientia 1990, 46, A74.
Bandtlow et al., Purification and biochemical characterization of rat and bovine CNS myelin associated neurite growth inhibitors NI-35 And NI-250. Soc. Neurosci. Abstract, 1991, vol. 17, No. 2, p. 1495, No. 598.11.
Barinaga M. Neurotrophic factors enter the clinic. Science. May 6, 1994;264(5160):772-774.
Bastmeyer et al., Encounter of goldfish retinal axons with rat CNS myelin and oligodendrocytes. Eur. J. Neurosci., Suppl. 1988, 1:207.
Bastmeyer et al., Rat CNS-myelin and Oligodendrocytes Impair the growth of goldfish retinal axons in vitro. Soc. Neurosci. Abstr. 1988, 14:452.
Benacerraf et al. (edtors). Figure 3.1: Schematic representation of an IgG antibody molecule. in Textbook of Immunology (Williams & Wilkins, 1979), pp. 32.
Benfey and Aguayo, Extensive elongation of axons from rat brain into peripheral nerve grafts. Nature. Mar. 11, 1982;296(5853):150-152.
Bjorklund and Stenevi, Regeneration of monoaminergic and cholinergic neurons in the mammalian central nervous system. Physiol Rev. Jan. 1979; 59(1):62-100.
Boggust et al., Inhibition of collagen peptidase in HeLa cells and human tumours by compounds including drugs used in cancer therapy. Br J Cancer. Aug. 1978;38(2):329-334.

(Continued)

*Primary Examiner*—Daniel E. Kolker
(74) *Attorney, Agent, or Firm*—Edwards Angell Palmer & Dodge LLP; Kathleen Williams; Amy DeCloux

(57) ABSTRACT

The present invention relates to the gene, Nogo, its encoded protein products, as well as derivatives and analogs thereof. Production of Nogo proteins, derivatives, and antibodies is also provided. The invention further relates to therapeutic compositions and methods of diagnosis and therapy.

7 Claims, 41 Drawing Sheets

OTHER PUBLICATIONS

Figure 3B:
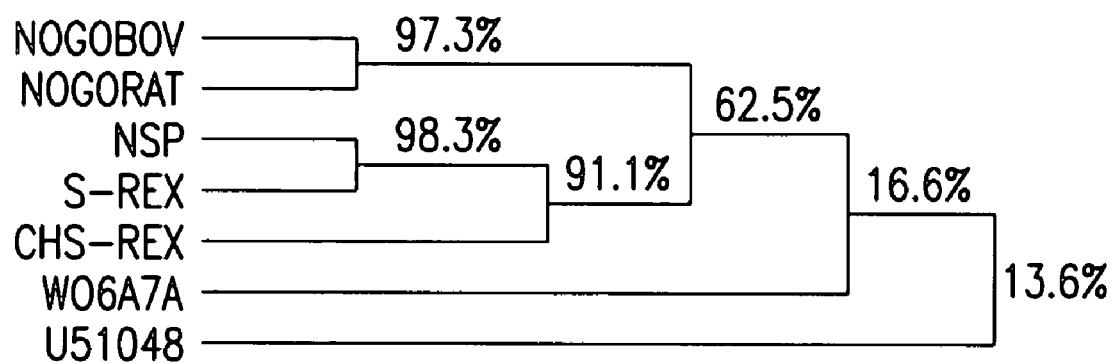

Boggust et al., Inhibition of collagen peptidase in HeLa cells and humna tumours by compounds including drugs used in cancer therapy. Chem. Abst. 1979, 90: 66525q.

Brecknell et al., Axonal regeneration. Biol Rev Camb Philos Soc. May 1996;71(2):227-255.

Bregman et al., Recovery from spinal cord injury mediated by antibodies to neurite growth inhibitors. Nature. Nov. 30, 1995;378(6556):498-501.

Bregman, Spinal cord transplant permit the growth of sertonergic axons across the site of neonatal spinal cord transection. Brain Res. Aug. 1987;431(2):265-279.

Bregman et al., Transplants, neurotrophic factors and myelin-associated neurite growth inhibitors. Effects on recovery of locomotor function after spinal cord injury in adult rats. Soc. Neurosci., 1996, vol. 22, part 1, p. 764.

Brochier, et al., Immunomodulating IL-6 activity by murine monoclonal antibodies. Int J Immunopharmacol. Jan. 1995;17(1):41-48.

Brösamle et al., Recombinant Fab-fragment against myelin-associated neurite growth inhibitors promotes axonal regeneration of lesioned corticospinal fibers in adult rat. Society for neuroscience Abstracts, 1996, vol. 22, part 2, p. 314, Abstract 130.2.

Brösamle et al., Recombinant Humanized IN-1 Fab-fragment promotes axonal regeneration of lisioned corticosponal fibers in adult rat. Soc. Neurosci, 1998, vol. 24, part 2, p. 1559.

Brösamle C. et al., Nerve fiber regeneration in adult CNS induced by a recombinant, humanized IN-I antibody fragment. Göttingen Neurobiol. Conference 1999, 2:833.

Buffo A et al., Application of IN-I antibodies to the adult rat cerebellum induces the outgrowth of intact purkinje cell axons. Soc Neurosci, 1999, 25(1) 1000 sec 402.1.

Cadelli et al. Oligodendrocyte- and myelin-associated inhibitors of neurite outgrowth: their involvement in the lack of CNS regeneration. Exp Neurol. Jan. 1992;115(1):189-192.

Cadelli and Schwab, Regeneration of Lesioned Septohippocampal Acetylcholinesterase-positive Axons is Improved by Antibodies against the Myelin-associated Neurite growth Inhibitors NI-35/250. Eur J Neurosci. 1991;3(9):825-832.

Cadelli et al., Regeneration of lesioned fiber tracts in the hippocampus and spinal cord of rats. Experientia 1991, 47, A2.

Caputo et al., Proteoglycan degradation by a chondrocyte metalloprotease. Effects of synthetic protease inhibitors. Biochem Pharmacol. Apr. 1, 1987;36(7):995-1002.

Carbonetto et al., Nerve fiber growth in culture on tissue substrata from central and perpheral nervous systems. J Neurosci. Feb. 1987;7(2):610-620.

Carlson et al., Synaptic vesicles and the synaptic extracellular matrix contain an identical proteoglycan-like antigen. J. Cell Biochem. 1984, 8 Part B: 293.

Caroni and Schwab, Antibody against myelin-associated inhibitor of neurite growth neutralizes nonpermissive substrate properties of CNS white matter. Neuron. Mar. 1988;1(1):85-96.

Caroni et al., Central nervous system regeneration: oligodendrocytes and myelin as non-permissive substrates for neurite growth. Prog Brain Res. 1988;78:363-370.

Caroni et al., A cell surface molecule that inhibits neurite outgrowth and cell locomotion. J. Cell Biol. 1986, 103 (5 Part 2): 470A.

Caroni et al., Two membrane protein fractions from rat central myelin with inhibitory properties for neurite growth and fibroblast spreading. Chem. Abst. 1988, 108: 219574X.

Caroni et al., Two membrane protein fractions from rat central myelin with inhibitory properties for neurite growth and fibroblast spreading. J Cell Biol. Apr. 1988;106(4):1281-1288.

Caroni and Schwab, Proteins of rat CNS white matter and of myelin forming oligodendrocytes are potent inhibitors of neurite outgrowth and cell locomotion. Soc. Neurosci. Abstr. 1987, 13: 1040.

Caroni et al., Presynaptic neurons may contribute a unique glycoprotein to the extracellular matrix at the synapse. Nature. Apr. 4-10, 1985;314(6010):441-443.

Caroni et al., Antibody against myelin-associated inhibitor of neurite growth neutralizes nonpermissive substrate properties of CNS white matter. Neuron. Mar. 1988; 1(1):85-96.

Caroni and Schwab, Two membrane proteins of myelin and oligodendrocytes inhibit neurite outgrowth and fibroblast migration. Experientia 1987,43: P 654.

Caroni and Schwab, Codistribution of neurite growth inhibitors and oligodendrocytes in rat CNS: appearence follows nerve fiber growth and precedes myelination. Dev Biol. Dec. 1989; 136(2):287-295.

Caroni et al., Potent membrane-bound inhibitors of neurite growth on the surface of cultured oligodendrocytes and in CNS white matter. Europ. J. Neurosci., Suppl. 1988, 1: 103.

Caroni et al., Cell surface inhibitors of neurite growth on differentiated oligodendrocytes: Appearence after nerve fiber growth and before myelination. Soc. Neurosci. Abstr. 1988, 14: 497.

Caroni and Schwab, Oligodendrocytes and CNS myelin contain inhibitory substrates for neurite growth. Experientia 1988, 44(Abstr.):A28.

Chen MS et al. Neurite outgrowth inhibitory factors in CNS myelin: molecular characterization of NOGO (NI-35/250). Soc. For Neuroscience 1998, 24(2):1766 sec 697.3.

Chen MS et al. Inhibitory activity and Domain(s) of the myelin protein NOGO-A. Soc Neurosci 1999, 25(1) 2030, Sec 806.3.

Chen et al., Expression of transformation-associated protease(s) that degrade fibronectin at cell contact sites. J Cell Biol. Apr. 1984; 98(4):1546-1555.

Chen and Chen, Fibronectin-degrading proteases from the membranes of transformed cells. Cell. Jan 30, 1987;48(2):193-203.

Chen et al., Efferent Projections of the facial motor cortex in the New World monkey *Saguinus labiatus*. Gottingen Neurobiology Conference, 1994, vol. II. p. 905.

Chen et al., Nogo-A is a myelin-associated neurite outgrowth inhibitor and an antigen for monoclonal antibody IN-1. Nature. Jan. 27, 2000;403(6768):434-439.

Chiquet-Ehrismann et al., Tenascin: an extracellular matrix protein involved in tissue interactions during fetal development and oncogenesis. Cell. Oct. 10, 1986;47(1):131-139.

Chiu et al., A monoclonal antibody that blocks the activity of a neurite regeneration-promoting factor: Studies on the binding site and its localization in vivo. J Cell Biol. Oct. 1986;103(4):1383-1398.

Coleman et al., Synthesis and incorporation of myelin polypeptides into CNS myelin. J Cell Biol. Nov. 1982;95(2 Pt 1):598-608.

Commissiong, Fetal locus coeruleus transplanted into the transected spinal cord of the adult rat: some observations and implications. Neuroscience. Jul 1984;12(3):839-853.

Cornbrooks et al., In vivo and in vitro observations on laminin production by Schwann cells. Proc Natl Acad Sci U S A. Jun. 1983;80(12):3850-3854.

Couch and Strittmatter, Rat myoblast fusion requires metalloendoprotease activity. Cell. Jan. 1983; 32(1):257-65.

Daniloff et al., Altered expression of neuronal cell adhesion molecules induced by nerve injury and repair. J Cell Biol. Sep. 1986;103(3):929-945.

Dutly and Schwab, How is oligodendrocyte differentiation and myelin formation regulated? Schweiz Arch Neurol Psychiatr. 1989;140(1):19-21.

Dutly et al., in Differentiation and Functions of Glial Cells: Proceedings of a Satellite Meeting of the International Society for Neurochemistry held in Rome, Italy, Apr. 19-21, 1989 (G. Levi, ed.; Wiley-Liss, 1990), pp. 149-150.

Dyer, 1951, "An Index of Tumor Chemotherapy" pp. 69, National Cancer Institute, National Institutes of Health.

Edelman GM, Expression of cell adhesion molecules during embryogenesis and regeneration. Exp. Cell Res. 1984, 161: 1-16.

Fischer et al., Neurite outgrowth patterns in cerebellar microexplant cultures are affected by antibodies to the cell surface glycoprotein L1. J Neurosci. Feb. 1986;6(2):605-12.

Fouad K et al. Neurite outgrowth patterns in cerebellar microexplant cultures are affected by antibodies to the cell surface glycoprotein L1. Soc Neurosci 1999, 25(1) 226 sec 91.7.

Guenther et al., A glia-derived neurite-promoting factor with protease inhibitory activity. EMBO J. Aug. 1985;4(8):1963-1966.

Guenther et al., A glia-derived neurite-promoting factor with protease inhibitory activity. Chem. Abst. 1985, 103: 270640z.

Hammerschlag et al., Metalloendoprotease inhibitors block fast axonal transport. J Neurochem. Jan. 1989;52(1):268-273.

Harris, and Emery, Therapeutic antibodies—the comming of age. Trends Biotechnol. Feb 1993;11(2):42-44.

Hawkins and Seeds, Effect of proteases and their inhibitors on neurite outgrowth from neonatal mouse sensory ganglia in culture. Brain Res. Nov. 19, 1986;398(1):63-70.

Hird V. et al. 1990. Immunotherapy with monoclonal antibodies. Chap. 17 In: Gene & Cancer, Eds. Carney D. & Sikora, K. pp. 183-189.

Hood et al. eds. Homology units in immunoglobulins correspond to molecular domains with different functions. in Immunology (The Benjamin/Cummings Publishing Company, Inc., 1978) pp. 214-219.

Huber A et al. Functional and developmental expression analysis of Nogo, a major inhibitor of CNS regeneration. Göttingen Neurobiol. Conference 1999, 2:834.

Huber et al. Developmental expression pattern and functional analysis of NOGO (formerly NI-35/250), a major inhibitor of CNS regeneration. Soc. For Neuroscience 1998, 24(2): 1559 sec 616.6.

Huber AB et al. Expression pattern of NOGO, a neurite outgrowth inhibitor, during development and in the adult rat. Soc Neurosci 1999, 25(1) 1263 Sec 505.2.

Huber and Schwab, Nogo-A, a potent inhibitor of neurite outgrowth and regeneration. Biol Chem. May-Jun. 2000;381(5-6):407-419.

Huber et al., Functional and expression analysis of NI-220. a putative inhibitor to CNS regeneration. Europ. J. Neurosci Suppl. 1998, 10, p. 61.

Johnson et al., Brain-derived neurotrophic factor supports the survival of cultured rat retinal ganglion cells. J Neurosci. Oct. 1986;6(10):3031-3038.

Johnson et al., Expression and structure of the human NGF receptor. Cell. Nov. 21, 1986;47(4):545-54.

Kapfhammer et al., Antibody neutralization of neurite growth inhibitors from oligodendrocytes results in expanded pattern of postnatally sprouting retinocollicular axons. J Neurosci. Jun. 1992;12(6):2112-2119.

Kapfhammer and Schwab, Inverse patterns of myelination and GAP-43 expression in the adult CNS: neurite growth inhibitors as regulators of neuronal plasticity? J Comp Neurol. Feb. 8, 1994;340(2):194-206.

Kapfhammer and Schwab, Myelin and GAP-43 have a pattern of complementary regional distribution in CNS gray matter of normal adult rats. Soc Neurosci. Abstract, 1992, vol. 18, Part 1, 262.12.

Kato et al., Inhibition of growth of mouse neuroblastoma cells by protein factor derived from rat glioblasts. Dev. Brain Res. 1982, 3: 645-651.

Keynes and Cook, Repulsive and Inhibitory signals. Curr Opin Neurobiol. Feb. 1995;5(1):75-82.

Kromer et al., Innervation of embryonic hippocampal implants by regene-ratings axons of cholinergic septal neurons in the adult rat. Brain Res. Apr. 6, 1981;210(1-2):153-171.

Lieberman, AR., The axon reaction: a review of the principal features of perikaryal responses to axon injury. Int Rev Neurobiol. 1971;14:49-124.

Liesi, P. Laminin-immunoreactive glia distinguish regenerative adult CNS systems from non-regenerative ones. EMBO J. Oct. 1985;4(10):2505-2511.

Liesi, P. Do neurons in the vertebrate CNS migrate on laminin? EMBO J. May 1985;4(5):1163-1170.

Lindner et al., Experimental modification of postnatal cerebellar granule cell migration in vitro. Brain Res. Jul. 9, 1986;377(2):298-304.

Mahdavi and Hynes, Proteolytic enzymes in normal and transformed cells. Biochim Biophys Acta. Mar. 7, 1979;583(2):167-178.

Mason et al., The hypogonadal mouse: reproductive functions restored by gene therapy. Science. Dec. 12, 1986;234(4782):1372-1378.

Matrisian et al., The mRNA coding for the secreted protease transin is expressed more abundantly in malignant than in benign tumors. Proc Natl Acad Sci U S A. Dec. 1986;83(24):9413-9417.

McConnell and Berry, Regeneration of ganglion cell axons in the adult mouse retina. Brain Res. Jun. 10, 1982;241(2):362-365.

Metz et al., Blockade of myelin-associated neurite growth inhibitors after unilateral pyramidotomy in adult rats results in functional recovery of forelimb use. Soc. Neurosci., 1997, vol. 23, part 1, p. 1196.

Mignatti et al., Tumor invasion through the human amniotic membrane: requirement for a proteinase cascade. Cell. Nov. 21, 1986;47(4):487-498.

Milstein, in Handbook of Experimental Immunology 4th ed. (Blackwell Scientific Publications, 1986) Chap. 107, pp. 107.1-107.13.

Mirsky et al., Distribution of the adhesion molecules N-CAM and L1 on peripheral neurons and glia in adult rats. J Neurocytol. Dec. 1986; 15(6):799-815.

Monard et al., Inhibition of protease activity can lead to neurite extension in neuroblastoma cells. Prog Brain Res. 1983;58:359-364.

Mullins and Rohrlich, The role of proteinases in cellular invasiveness. Biochim Biophys Acta. Dec. 29, 1983;695(3-4):177-214.

Mundy and Strittmatter, Requirement for metalloendoprotease in exocytosis: evidence in mast cells and adrenal chromaffin cells. Cell. Mar. 1985;40(3):645-656.

Nornes et al., Reinnervation of the denervated adult spinal cord of rats intraspinal transplants of embryonic brain stem neurons. Cell Tissue Res. 1983;230(1):15-35.

Osband and Ross, Problems in the investigational study and clinical use of cancer immunotherapy. Immunol Today. Jun. 1990;11(6):193-195.

Paganetti et al., Glioblastoma infiltration into central nervous system tissue in vitro: involvement of a metalloprotease. J Cell Biol. Dec. 1988; 107(6 Pt 1):2281-2291.

Pagnetti and Schwab, Glioblastoma infiltration into CNS tissue in vitro: the rile of a metalloprotease. Europ. J. Neurosci. Suppl. 1990, 3, 206.

Pagnetti and Schwab, Glioblastoma cells overcome CNS tissue inhibitory substrate properties by means of metalloprotoases. Europ. J. Neurosci., Suppl. 1, 1988, p. 240.

Pagnetti and Schwab, Glioblastoma infiltration into CNS tissue in vitro: involvement of two distinct proteases. Soc. Neurosci. Abstr. 1989, 15:507.

Pagnetti and Schwab, Glioblastoma infiltration into CNS tissue in vitro: involvement of two distinct proteases. J. Neuro-Oncology 1989,, 7, Suppl., p. 24.

Pagnetti et al., Oligodendrocytes inhibit neuronal growth cone movement. Experentia 1989, 45, A30.

Pittman, RN, Release of Plasminogen activator and a calcium-dependent metalloprotease from cultured sympathetic and sensory neurons. Dev Biol. Jul. 1985;110(1):91-101.

Quigley, JP, Association of a protease (plasminogen activator) with a specific membrane fraction isolated from transformed cells. J Cell Biol. Nov. 1976;71(2):472-486.

Rainetreau Q et al. Anatomical reorganization of the spinal tracts after corticospinal tract lesion: a role for the rubrospinal tract? Soc Neurosci 1999, 25(1) 2031, Sec 806.14.

Readhead et al. Expression of a myelin basic protein gene in transgenic shiverer mice: correction of the dysmyelinating phenotype. Cell. Feb. 27, 1987;48(4):703-712.

Richardson et al., Regeneration of long spinal axons in the rat. J Neurocytol. Feb. 1984; 13(1):165-182.

Sakazaki et al., Characterization and partial purification of neuroblastoma growth inhibitory factor from the culture medium of glioblasts. Brain Res. Feb. 28, 1983;262(1):125-135.

Sanes, JR, Roles of extracellular matrix in neural development. Annu Rev Physiol. 1983;45:581-600.

Saneto et al., In Neurochemistry: a practical approach (Tuner ed; IRL Press, 1987) pp. 28-63.

Savio and Schwab, Rat CNS white matter, but not gray matter, is non-permissive for neuronal cell adhesion and fiber outgrowth. J Neurosci. Apr. 1989;9(4):1126-1133.

Savio and Schwab, Rat CAN white matter is a non-permissive substrate for neuronal cell adhesion and neurite growth. Neurosci. Lett., Suppl. 1988, 33: S172.

Savio and Schwab, CNS white matter is a non-permissive substrate for neuron adhesion and neurite growth. Experientia 1988, 44 (Abstr.):A27.
Savio and Schwab, CNS white matter, but not gray matter, is a non-permissive substrate for neuron adhesion and neurite growth. Eur. J. Neurosci., Suppl. 1988, 1: 207.
Savio et al., Cortico-spinal tract regeneration occurs in x-irradiated myelin-free rat spinal cord or by application of an antibody against myelin-associated neurite growth inhibitors. Soc. Neurosci. Abstract, 1989, 15:317.
Schmidt et al., Soc. Neurosci. Abstract vol. 17, 1991, No. 372.7.
Schnell and Schwab, Axonal regeneration in the rat spinal cord produced by an antibody against myelin-associated neurite growth inhibitors. Nature. Jan. 18, 1990;343(6255):269-272.
Schnell and Schwab, Sprouting and regeneration of lesioned corticospinal tract fibres in the adult rat spinal cord. Eur J Neurosci. Sep. 1, 1993; 5(9):1156-1171.
Schnell et al., Neurotrophin-3 enhances sprouting of corticospinal tract during development after adult spinal cord lesion. Nature. Jan. 13, 1994;367(6459):170-173.
Schwab and Caroni, Rat CNS myelin and a subtype of oligodendrocytes in culture represent a non-permissive substrate for neurite outgrowth. Neurosci. Lett. 1986, 26:S19.
Schwab, A subtype of oligodendroglial cells represents a non-permissive substrate for neuronal attachment and fiber growth. Experientia 1986, 42: 632.
Schwab, Neurite growth inhibitors in the central nervous system; roles in development and regeneration. in Neural Development. T. Wiesel et al, eds., 1991, vol. VII, pp. 49-50.
Schwab and Caroni, Rat CNS myelin and subtype of oligodendrocytes in culture represent a non-permissive substrate for neurite growth and fibroblast spreading. Soc. Neurosci. 1986, 12:12.
Schwab and Thoenen, Dissociated neurons regenerate into sciatic but not optic nerve explants in culture irrespective of neurotrophic factors. J Neurosci. Sep. 1985;5(9):2415-2423.
Schwab, Myelin-associated inhibitors of neurite growth. Exp Neurol. Jul. 1990;109(1):2-5.
Schwab and Savio, Regional appearance of myelin constituents in the developing rat spinal cord. Soc. Neurosci. Abstr. 1988, 14: 1200.
Schwab et al., Oligodendrocytes and CNS myelin are non-permissive substrates for neurite growth and fibroblast spreading in vitro. Chem. Abst. 1987, 109: 108200y.
Schwab, Neurite growth inhibitors in the mammalian central nervous system. I.B.R.O. News 1989, 17:7.
Schwab, Neuron-glia interactions in the development and regeneration of the central nervous system. Neurosci Lett., Suppl. 1989, 36 suppl.
Schwab, Substrates inhibiting neurite growth in the CNS. Experientia 1989, 45(Abstr.): A1.
Schwab et al., Myelin-associated inhibitors of nerve fiber growth. J. Neuro-Oncology 1989, 7(Suppl.):S26.
Schwab et al., Symposium. Inhibitory influences on growth cones and cells. Soc. Neurosci. Abstr. 1989, 15: 1106.
Schwab et al., Oligodendrocytes and myelin inhibit growth of neurites in the mammalian CNS. Psychopharmacology, 1988; 96. suppl. 15.
Schwab and Schnell, Region-specific appearance of myelin constituents in the developing rat spinal cord. J Neurocytol. Apr. 1989; 18(2):161-169.
Schwab, M., Inhibitors of nerve fiber growth in the central nervous system. 1989 AAAS Annual Meeting, (155th National Meeting, San Francisco, Jan. 14-19) Abstracts of Papers, 1988, (88-30):63.
Schwab et al., Growth factors and substrate pathways for peripheral nerve cells,—an overview. Neurosci. Lett., Suppl. 1984, 18: S423.
Schwab, Interaction of neurons with nerve explants and dissociated glial cells in culture. Neurosci. Lett., Suppl. 1985, 22: S365.
Schwab and Thoenen, in Experimental Brain Research, Suppl. 13: Process of Recovery From Neural Trauma, International Symposium, Israel, Jun. 1984 (Gilad et al., eds.; Springer-Verlag, 1986), pp. 205-214.
Schwab et al., Oligodendrocytes and CNS myelin are non-permissive substrates for neurite growth and fibroblast spreading in vitro. J Neurosci. Jul. 1988;8(7):2381-2393.

Schwab et al., Oligodendrocytes and myelin as non-permissive substrates for neurite regeneration. J. Neurochem. 1987, 48(Suppl.):S17.
Schwab et al., 1991 ,Neutie growth inhibitors in the adult mammalian central nervous system. Neurodegenerative Disorders: Mechanisms and Prospectts for Therapy. Price et al., eds., J. Wiley & Sons Ltd., Life Sci. Res. Report LS51, pp. 157-164.
Schwartz, M, Molecular and cellular aspects of nerve regeneration. CRC Crit Rev Biochem. 1987;22(2):89-110.
Schwartz and Spirman, Sprouting from chicken embryo dorsal root ganglia induced by nerve growth factor is specifically inhibited by affinity-purified antiganglioside antibodies. Proc Natl Acad Sci U S A. Oct. 1982;79(19):6080-6083.
So and Aguayo, Lengthy regrowth of cut axons from ganglion cells after peripheral nerve transplantation into the retina of adult rats. Brain Res. Mar. 4, 1985;328(2):349-354.
Sonnenfeld and Ishii, Nerve growth factor effects and receptors in cultured human neuroblastoma cell lines. J Neurosci Res. 1982; 8(2-3):375-31.
Spillmann et al., Purification of a neurite growth inhibitor (NI-250) from bovine CNS myelin. NATO ASI Series 1995, H92:23-28.
Spillmann et al., High molecular weight protein of human central nervous system myelin inhibits neurite outgrowth: an effect which can be neutralized by the monoclonal antibody IN-1. Eur J Neurosci. Mar. 1997;9(3):549-55.
Spillmann et al., Purification of a neurite growth inhibitor (NI-250) from bovine CNS myelin. Experientia, 1995, vol. 51, pp. A44.
Spillmann et al., Purification of a neurite growth inhibitor (NI-250) from bovine CNS myelin. Protein Sci., 1995, vol. 4, Suppl. 1, p. 90.
Spillmann et al., Purification of a neurite growth inhibitor (NI-250) from bovine CNS myelin Soc. Neurosci., 1995, vol. 21, part 2, p. 1560.
Spillmann, et al., Purification and molecular cloning of an inhibitor to CNS regeneration. Soc. Neurosci., 1996, vol. 22, part 1, p. 734.
Spillmann et al., Identification and characterization of a bovine neurite growth inhibitor (bNI-220). J Biol Chem. Jul. 24, 1998;273(30);19283-19293.
Stallcup et al., Antibody against growth factor-inducible large external (NILE) glycoprotein labels nerve fiber tracts in the developing rat nervous system. J Neurosci. Apr. 1985;5(4):1090-101.
Tatagiba et al., Regeneration of the anotomized auditory nerve in the adult rat promoted by intrathecal application of a recombinant IN-1 Fab. Neurosci Abstract, 1996, vol. 22, part 1, p. 315.
Tatagiba et al., Regeneration of the axotomized auditory nerve in the adult rat. Soc. Neurosci., 1998, vol. 24, part 2, p. 1559.
Tessier-Lavigne and Goodman, The molecular biology of axon guidance. Science. Nov. 15, 1996;274(5290):1123-1133.
Thallmair Thallmair et al., Neurite growth inhibitors restrict plasticity and functional recovery following corticospinal tract lesions. Nat Neurosci. Jun. 1998;1(2):124-131.
Thallmair et al. Neutralization of the IN-1 antigen leads to increased plastic fiber growth after unilateral cortical lesions in adult rats. Soc Neurosci 1999, 25(1) 2029, Sec 806.2.
Thallmair M et al. Increased corticofugal plasticity after unilateral cortical lesions in adult rats and neutralization of the IN-1 antigen. Göttingen Neurobiol. Conference 1999, 2:829.
Thallmair et al., Neutralization of myelin-associated neurite growth inhibitors increased plastic fiber growth after unilateral pyramidal tract lesions in the adult rat spinal cord. Soc. Neurosci., 1997, vol. 23, part 1, p. 609.
Thoenen et al., In Repair and Regeneration of the Nervous System (Nicholls, ed.; Springer-Verlag, 1982), pp. 173-185.
Tobey et al., Neurite extension by neuroblastoma cells on substratum-bound fibronectin's cell-binding fragment but not on the heparan sulfate-binding protein, platelet factor-4. Exp Cell Res. Jun. 1985;158(2):395-412.
Turner et al., Extract from brain stimulates neurite outgrowth from fetal rat retinal explants. Brain Res. Dec. 1982;282(1):77-83.
Tuszynski et al., Nerve growth infusions combined with fetal hippocampal grafts enhance reconstruction of the lesioned septohippocampal projection. Neuroscience. 1990;36(1):33-44.
Van der Haas ME, et al. Myelin-associated neurite outgrowth inhibitory factors: recombinant expression of Nogo (NI-220/250). Soc. For Neuroscience 1998, 24(2): 1559 sec 616.7.

Van der Haas et al., Recombinant expression of the myelin-associated neurite outgrowth inhibitor. Europ. J. Neurosci. Suppl. 1998, 10, p. 61.

Vanselow et al., Interactions between fibers from chick embryonic retinal explants and central glial cells from the postnatal rat optic nerve. Eur. J. Neurosci., Suppl. 1988, 1:240.

Weibel et al., Regeneration of lesioned rat optic nerve fibers is improved after neutralization of myelin-associated neurite growth inhibitors. Brain Res. Apr. 11, 1994;642(1-2):259-266.

Weinberg and Spencer, Studies on the control of myelinogenesis. 3. Signalling of oligodendrocyte myelination by regeneration peripheral axons. Brain Res. Feb. 23, 1979;162(2):273-279.

Westall et al., Brain-derived fibroblast growth factor: identity with a fragment of the basic protien of myelin. Proc Natl Acad Sci U S A. Oct. 1978;75(10):4675-4678.

Wilhelm et al., Human skin fibroblast stromelysin: structure, glycosylation, substrate specificity, and differential expression in normal and tumorigenic cells. Proc Natl Acad Sci U S A. Oct. 1987;84(19):6725-6729.

Zagrebelsky et al., Myelin-associated neurite growth inhibitors control the expression of growth-associated molecules in adult rat perkinje cells. Soc. Neurosci., 1998, vol. 24, part 2, p. 1754.

Z'Graggen et al. Functional recovery and enhanced corticofugal plasticity after unilateral pyramidal tract lesion and blockade of myelin-associated neurite growth inhibitors in adult rats. J. Neurosci. Jun. 15, 1998;18(12):4744-4757.

Z'Graggen et al., Plasticity of corticofugal projections following unilateral pyramidotomy and blockade of myelin associated neurite growth inhibitors in adult rats. Soc. Neurosci, 1997, vol. 23 part 2, p. 1449.

Zucker et al., Diversity of melanoma plasma membrane proteinases: inhibition of collagenolytic and cytolytic activities by minocycline. J Natl Cancer Inst. Sep. 1985;75(3):517-525.

Schwab et al. Antibodies against myelin associated neurite growth inhibitors and bridges improved regeneration of lesioned nerve fibers in spinal cord and optic nerve. Soc. For Neurosci. Abstract, 1990, vol. 16, 169.

Wells (Sep. 18, 1990) "Additivity of Mutational Effects in Proteins." Biochemistry 29(37): 8509-8517.

Ngo et al. (Mar. 2, 1995) "The Protein Folding Problem and Tertiary Structure Prediction, Chapter 14: Computational Complexity Protein structure Prediction, and the Levinthal Paradox", pp. 492-495.

Bork (2000) "Powers and Pitfalls in Sequence Analysis: The 70% Hurdle." Genome Research 10:398-400.

Skolnick and Fetrow (2000) "From gene to protein structure and function: novel applications of computational approaches in the genomic era." Trends in Biotech. 18(1):34-39.

Doeks et al., (Jun. 1998) "Protein annotation: detective work for function prediction." Trends in Genetics 14(6): 248-250.

Smith and Zhang (Nov. 1997) "The challenges of genome sequence annotation or 'The devil is in the details'." Nature Biotechnology 15:1222-1223.

Brenner (Apr. 1999) "Errors in genome annotation." Trends in Genetics 15(4): 132-133.

Bork and Bairoch (Oct. 1996) "Go hunting in sequence database but watch out for the traps." Trends in Genetics 12(10):425-427.

Morris et al., (1999), "Cloning and Characterization of a 22 kDa protein from rat adipocytes: a new member of the reticulon family." Biochim. Biophys. Acta 1450: 68-76.

Chen et al., (Jan 27, 2007) "Nogo-A is a meyelin-associated neurite outgrowth inhibitory and an antigen for monoclonal antibody IN-1". Nature 403: 434-439.

GrandPre et al. (2002) "Nogo-66 receptor antagonist peptide promotes axonal regeneration." Nature 417:547-551.

Schendel 1998, Expression of Proteins in *Escherichia coli*—Overview of Protein Expression in *E. coli*. In: Current Protocols in Molecular Biology 16.1.1-16.1.3, John Wiley & Sons, Inc.

Sambrook et al., Analysis and Cloning of Eukaryotic Genomic DNA (p. 9.49) In: Molecular Cloning: A Laboratory Manual, 1989, Cold Spring Harbor Laboratory Press.

Prinjha et al., 2000, Inhibitor of Neurite Outgrowth in Humans, Nature 403:383-384.

Hopp and Woods, 1981, Prediction of Protein Antigenic Determinants from Amino Acid Sequences, PNAS 78:3824.

Genbank Accession No. AF051335, Jan 19, 2000.
Genpept Accession No. NP_989697, Nov. 18, 2006.
Genbank Accession No. AAF01564, Jan. 19, 2000.
Genbank Accession No. AAD27783, Nov. 21, 2002.
Genbank Accession No. AAG12205, Sep. 9, 2000.
Genbank Accession No. AAG43160, Jan. 2, 2001.
Genbank Accession No. BAA83712, Sep. 3, 1999.
Genbank Accession No. AJ242961, Jan. 28, 2000.
Genbank Accession No. BAA74909, Jan. 10, 2004.
Genbank Accession No. Q9NQC3, Nov. 16, 2001.

* cited by examiner

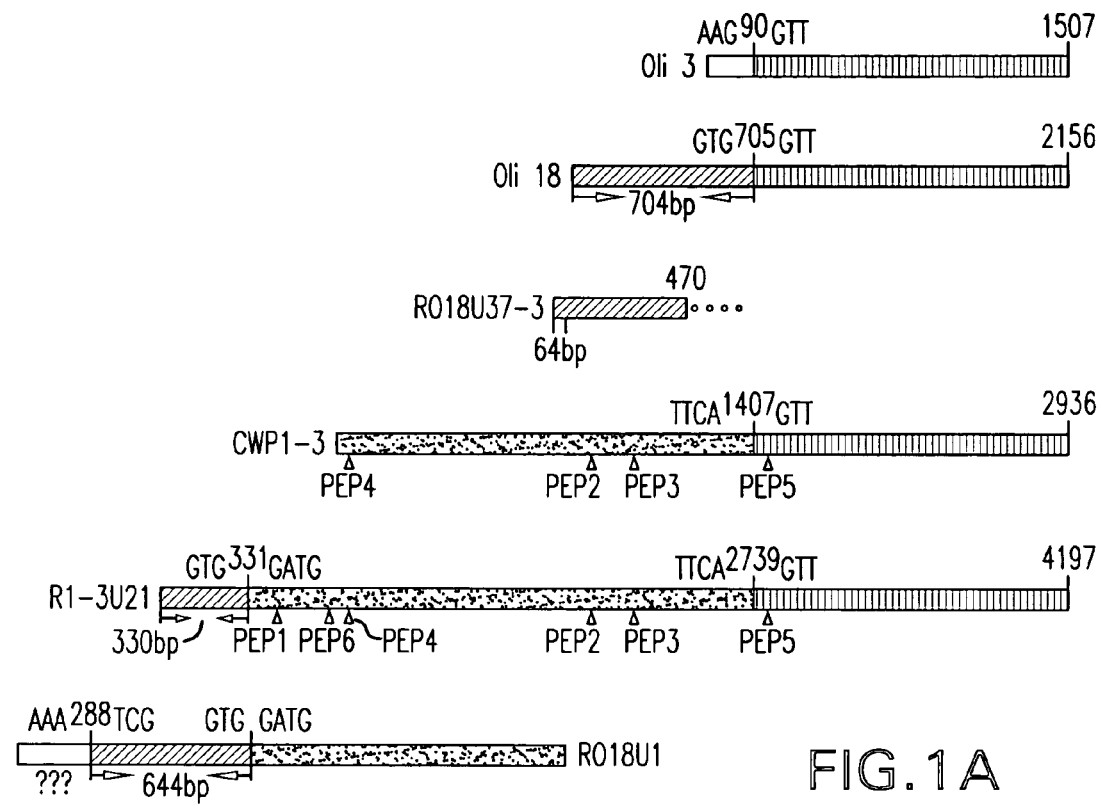
FIG.1A
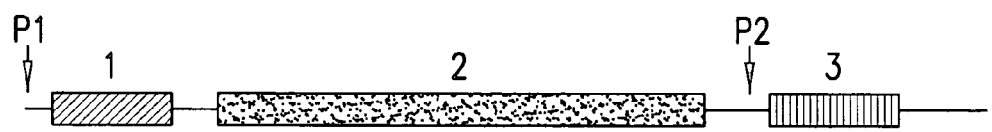
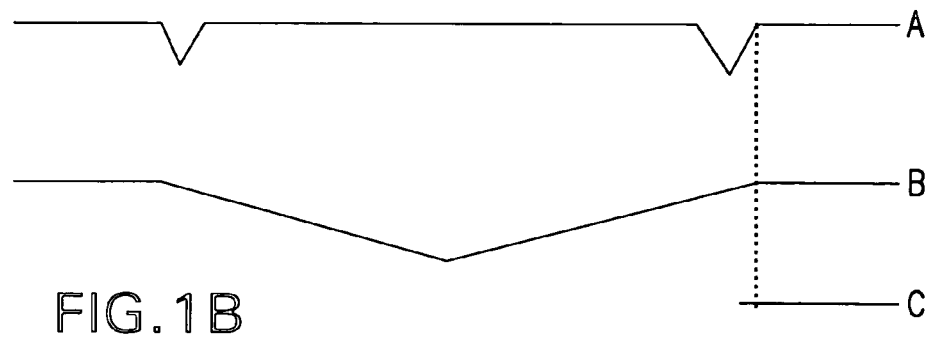
FIG.1B

```
                                          ATTG CTCGTCTGGG GGCTGCAGCC TGGGACAGGG CGGGTGCCAC ATCTCGATCG
CGAAGGCAGG AGAAGCAGTC TCATTGTTCC GGGAGCCGTC GCCTCTGCAG GTTCTTCGGC GCCTCCTGGC ACGACTCCGG CCTGCCAGTC
TTGCCCAACC CCCACAACCG CCCGCGACTC TGAGGAGAAG CGGCCCTGCG GGGCTGTAG CTGCAGCATC GTCGGCGACC CGCCAGCC(ATG)GAAGACATA     4
                                                                                        M  E  D  I
```

```
GACCAGTCGT GGCTGGTCTC CTCGTCCACG GACAGCCCGC CCCGGCCTTC AGTACCAGT  TGTGACGGA GCCCGAGGAC GAGGAGGAC      37
D   Q  S  S  L  V  V  S  S  S  T  D  S  P  P  R  P  P  P  A  F  K  Y  Q   F  V  T  E  P  E  D  E  E  D
                                                                               △
```

[Figure 2A1 continues with DNA and protein sequence]

FIG.2A1

```
ATTTGTAAAT AGAGATTTAG CAGAATTTC AGAATTAGAA TATTCAGAAA TGGATCATC TTTTAAAGGC TCCCAAAAG GAGAGTCAGC CATATTAGTA
 P  F  V  N  R  D  L  A  E  F  S  E  L  E  Y  S  E  M  G  S  [S] F  K  G  [S] P  K  G  E  S  A  I  L  V   304

GAAACACTA AGGAGAAGT AATTGTGAGG AGTAAAGACA AAGAGGATTT AGTTGTAGT GCAGCCCTTC ACAGTCCACA AGAATCACCT GTGGGTAAAG
 E  N  T  K  E  E  V  I  V  R  S  K  D  K  E  D  L  V  C  S  A  A  L  H  S  P  Q  E  S  P  V  G  K       337

AAGACAGAGT TGTGTCTCCA GAAAAGACAA TGGACATTTT TAATGAAATG CAGATGTCAG TAGTAGCACC TGTGAGGGAA GAGTATGCAG ACTTTAAGCC
 E  D  R  V  V  V  S  P  E  K  T  M  D  I  F  N  E  M  Q  M  S  V  V  A  P  V  R  E  E  Y  A  D  F  K    370

ATTTGAACAA GCATGGGAAG TGAAAGATAC TTATGAGGGA AGTAGGGATG TGCTGGCTGC TAGAGCTAAT GTGGAAGTA AAGTGGACAG AAAATGCTTG
 P  F  E  Q  A  W  E  V  K  D  T  Y  E  G  S  R  D  V  L  A  A  R  A  N  V  E  S  K  V  D  R  K  C  I    404

GAAGATAGCC TGGAGCAAAA AAGTCTTGGG AAGGATAGTG AAGGCAGAAA TGAGGATGCT TCTTTCCCCA GTACCCCAGA ACCTGTGAAG GACAGCTCCA
 E  D  S  L  E  Q  K  S  L  G  K  D  S  E  G  R  N  E  D  A  S  F  P  S  T  P  E  P  V  K  D [S] S       437

GAGCATATAT TACCTGTGCT TCCTTTACTT CAGCAACCGA AGCACCACA GCAAACACTT TCCCTTGTT AGAAGATCAT ACTTCAGAAA ATAAAACAGA
 R  A  Y  I  T  C  A  S  F  T  S  A  T  E  S  T  T  A  N  T  F  P  L  L  E  D  H  T  S  E  N  K  T      470
                                                                                                   ─────

TGAAAAAAAA ATAGAAGAAA GGAAGGCCCA AATTATAACA GAGAAGACTA GCCCCAAAAC GTCAAATCCT TTCCTTGTAG CAGTACAGGA TTCTGAGGCA
 D  E  K  K  I  E  E  R  K  A  Q  I  I  [E] K  T [S] P  K  T  S  N  P  F  L  V  A  V  Q  D  S  E  A     504
                                                                                                 △

GATTATGTTA CAACAGATAC CTTATCAAAG GTGACTGAGG CAGCAGTGTC AAACATGCCT GAAGGTCTGA CGGCCAGATT AGTTCAGGAA GCATGTGAAA
 D  Y  V  T  T  D  T  L  S  K  V  T  E  A  A  V  S  N  M  P  E  G  L  T  P  D  L  V  Q  E  A  C  E      537

GTGAACTGAA TGAAGCCACA GGTACAAAGA TTGCTTATGA AACAAAAGTG GACTTGGTCC AAACATCAGA AGCTATACAA GAATCACTTT ACCCCACAGC
 S  E  L  N  E  A  T  G  T  K  I  A  Y  E  T  K  V  D  L  V  Q  T  S  E  A  I  Q  E  S  L  Y  P  T      570

ACAGCTTTGC CCATCATTTG AGGAAGCTGA AGCAACTCCG TCACCAGTTT TGCCTGATAT TGTTATGGAA GCACCATTAA ATTCTCTCCT TCCAAGCGCT
 A  Q  L  C  P  S  F  E  E  A  E  A  T  P  S  P  V  L  P  D  I  V  M  E  A  P  L  N  S  L  L  P  S  A   604
              △

FIG.2A2
```

```
GGTGCTTCTG TAGTGCAGCC CAGTGTATCC CACTCCTCC AGTTAGTTAT GACAGTATAA AGCTTGAGCC TGAAACCCC CCACCATATG
 G  A  S   V  V  Q    P  S  V  S   P  L  E   A  P  P    P  V  S  Y  D ⑤ I  K  L  E   P  E  N  P    P  P  Y                                         637

AACAAGCCAT GAATGTAGCA CTAAAAGCTT TGGAACAAA GGAAGGAATA AAAGAGCCTG AAAGTTTTAA TGCAGCTGTT CAGGAAACAG AAGCTCCTTA
 E  E  A  M  N  V  A  L  K  A    L  G  T    K  E  G    I  K  E  P    E  S  F  N  A  A  V  Q  E  T    E  A  P                                       670

TATATCCATT GGCTGTGATT TAATTAAAGA AACAAAGCTC TCCACTGAGC CAAGTCCAGA TTTCTCTAAT TATTCAGAAA TAGCAAAATT CGAGAAGTCG
 Y  I  S  I    G  C  D    L  I  K   E  T  K  L    S  T  E    P  S  P    D  F  S  N    Y  S  E   I  A  K   F  E  K  S                              704

GTGCCCGAAC AGGCTGAGCT AGTGGAGGAT TCCTCACCTG AATCTGAACC AGTTGACTTA TTTAGTGATG ATTCGATTCC TGAAGTCCCA CAAACACAAG
 V  P  E  H  A  E    L  V  E  D    S  S  P    E  S  E   P  V  D  L   F  S  D  D  S  I   P  E  V  P    Q  T  Q                                     737
                                                 △

AGGAGCTGT GATGCTCATG AAGGAGAGTC TCACTGAAGT GTAGCCCAGC ACAAAGAGGA GAGACTTAGT GCCTCACCTC AGGAGCTAGG
 E  E  A  V  M  L  M    K  E  S    L  T  E    V  S  E  T    V  A  Q    H  K  E  E  R  L  S   A  S  P    Q  E  L                                   770

AAAGCCATAT TTAGAGTCTT TTCAGCCCAA TTTACATAGT ACAAAAGATG CTGCATCTAA TGACATTCCA ACATTGACCA AAAAGGAGAA AATTTCTTTG
 G  K  P  Y   L  E  S    F  Q  P    N  L  H ⑤ T  K  D    A  A  S    N  D  I  P    T  L  T    K  K  E    K  I  S  L                                 804

CAAATGGAAG AGTTTAATAC TGCAATTTAT TCAAATGATG ACTTACTTTC TTCTAAGGAA GACAAAATAA AAGAAAGTGA AACATTTTCA GATTCATCTC
 Q  M  E  E  F  N  T    A  I  Y    S  N  D    D  L  L  ⑤ S  K  E    D  K  I    K  E  S    E  T  F  S    D  S  S                                    837

CGATTGAGAT AATAGATGAA TTTCCCACGT TTGTCAGTGC TAAAGATGAT TCTCCTAAAT TAGCCAAGGA GTACACTGAT CTAGAAGTAT CGGACAAAAG
 P  I  E   I  I  D  E    F  P  T    F  V  S⑤  A  K  D  D ⑤ P  K    L  A  K    E  Y  T  D    L  E  V ⑤ D  D  K                                     870
                                                                                              △

TGAAATTGCT AATATCCAAA GCGGGGCAGA TTCATTGCCT TGCTTAGAAT TGCCCTGTGA CCTTTCTTTC AAGAATATAT ATCCTAAAGA TGAAGTACAT
 S  E  I  A   N  I  Q    S  G  A    D  S  L  P    C  L  E    L  P  C    D  L  ⑤ F  K  N  I    Y  P  K    D  E  V  H                                904

GTTTCAGATG AATTCTCCGA AAATAGGTCC AGTGTATCTA AGGCATCCAT ATCGCCTTCA AATGTCTCTG CTTTGGAACC TCAGACAGAA ATGGGCAGCA
 V  S  D  E  F  S  E    N  R  S    S  V  S    K  A  S    I  S  P  S    N  V  S    A  L  E    P  Q  T  E    M  G  S                                 937
```

FIG.2A3

```
TAGTTAAATC CAAATCACTT ACGAAAGAAG CAGAGAAAAA ACTTCCTTCT GACACAGAGA AAGAGGACAG ATCCCTGTCA GCTGTATTGT CAGCAGAGCT   970
 I  V  K   S  K  S  L    T  K  E    A  E  K  K  L  P   S   D   D    E   K  E  D    R  S  L  S    A  V  L    S  A  E

GAGTAAAACT TCAGTTGTTG ACCTCCTCTA CTGGAGAGAC ATTAAGAAGA CTGGAGTGGT GTTTGGTGCC AGCTTATTCC TGCTGCTGTC TCTGACAGTG  1004
 L  S  K  T    S  V  V    D  L  L    Y  W  R  D    I  K  K    T  G  V    V  F  G  A    S  L  F    L  L  L    S  L  T  V

TTCAGCATTG TCAGTGTAAC GGGCTACATT GCCCTTGGCC TGCTCTCGGT GACTATCAGC TTTAGGATAT ATAAGGGCGT TATTCAGGCT ATCCAGAAAT  1037
 F  S  I    V  S  V  T    A  Y  I    A  L  A    L  L  S    V  T  I    S    F  R  I    Y  K  G    V  I  Q  A    I  Q  K

TCAGATGAAGG CCACCCATTC AGGGCATATT TAGAATCTGA AGTTGCTATA TCAGAGGAAT TGGTTCAGAA ATACAGTAAT TCTGCTCTTG GTCATGTGAA  1070
 S  D  E    G  H  P  F    R  A  Y    L  E  S    E  V  A  I    S  E  E    L  V  Q    K  Y  S  N    S  A  L    G  H  V

CAGCACAATA AAAGAACTGA GGCGGCTTTT CTTAGTTGAT GATTTAGTG GATTCCCTGAA GTTTGCAGTG TTGATGTGGG TGTTTACTTA TGTTGGTGCC  1104
 N   S    I    K  E  L    R  R  L    F   L  V  D    D  L  V    D    L  K  F  A  V    L  M  W    V  F  T    Y  V  G  A

TTGTTCAATG GTCTGACACT ACTGATTTTA GCTCTCATCT CACTCTTCAG TATTCCTGTT ATTTATGAAC GGCATCAGGT GCAGATAGAT CATTATCTAG  1137
 L  F  N    G  L  T    L  L  I  L    A  L  I    S  L  F    S  I  P  V    I  Y  E    R  H  Q    V  Q  I  D    H  Y  L

GACTTGCAAA CAAGAGTGTT AAGGATGCCA TGGCCAAAAT CCAAGCAAAA ATCCCTGGAT TGAAGCGCAA AGCAGATTGA AAAAGCCCCA AACAGAAGTT  1163
 G   L  A    N  K   S     K  D  A    M  A  K    I  Q  A  K    I  P  G    L  K  R    R  K  A  D  *

CATCTTTAAA GGGGACACTC ACTTGATTAC GGGGGTGGGA GGGTCAGGGG TGAGCCCTTG GTGGCCGTGC GGTTTCAGCT CTTTATTTTT AGCAGTGCAC
TGTTTGAGGA AAAATTACCT GTCTTGACTT GTCTGTGTTA TCATCTTAAG TATTGTAAGC TGCTCTGTAT GGATCTCATT GTAGTCACAC TTGTCTTCCC
CAATGAGGCG CCTGGTGAAT AAAGGACTCG GGGAAAGCTG TGCATTGTAT GGTCAGTGTG TGCTGTGTAT CTGTGCAGG GTAGTCTAGC TGTATGCAGA GAGTGTAAA GAAGGCAAAT
CTAAAGCAGA GTGGAAAACT CTGTGTTATT CCTTGCAGCT AGATCTTTAA CCTACCACC TGTTTTCAAG GACTGAATT CAATATGAAT GTTTAGATGA GAGTCATACTA
TATATGTTTT CACAAAGTTG TAGGAGTGCT CACAGACTCT GAAATTCTAT GGACTGAATT TCATGCTTCC AAATGTTTGC AGTTATCAAA CATTGTTATG CAAGAAATCA
TAGGAAGAGA AATGTATTTG TTAATTTTGT TCAACTTGTA TTTGTGTTTA GGGCGTACTG AGCCGTACTG TTGAACTGTA AAGCAAAGT ATCAATAAAG CTTATAGACT
TAAAATGCAA ACTTATACCA
TAAAAAAAAA AAAAAAAAAA
```

FIG. 2A4 peptide 1:      EYLGDLPAVLPTE        peptide 4:      KXFEXVWEV
    (bovine)    EYLGDLPAVLPTE            (bovine)    KPFERVWEV
    (rat)       gYLGnLsAVsssE            (rat)       KPFEQaWEV peptide 2:      EIAEIQDG ESL         peptide 5:      VVDLLYWRDIK
    (bovine)    EIAdIQDGagSL             (bovine)    VVDLLYWRDIK
    (rat)       EIAnIQsGadSL             (rat)       VVDLLYWRDIK peptide 3:      KXYLESIQPSLGITK      peptide 6:      KAVAAEASMREEYADF
    (bovine)    KPYLESfQPSLGITK          (bovine)    KgVAAEASMgEEYADF
    (rat)       KPYLESfQPnLhsTK          (rat)       mqmsvvApvREEYADF

FIG.2B

FIG. 3A

Figure 6A:
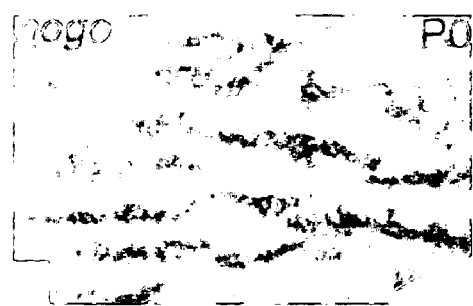
Figure 6B:
Figure 6C:
Figure 6D:

 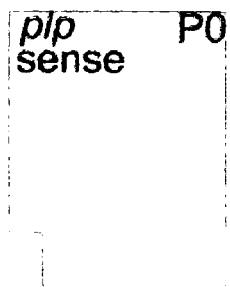 
FIG.6E     FIG.6F     FIG.6G
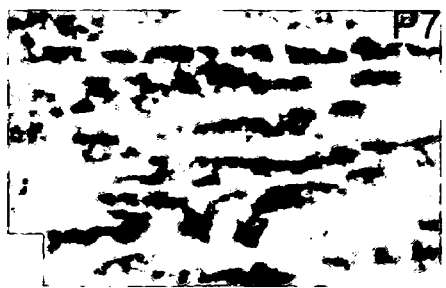 
FIG.6H     FIG.6I

| CULTURE | pre-472 | AS 472 |
|---|---|---|
| 1 | − | ++ |
| 2 | − | +++ |
| 3 | + | +++ |
| 4 | + | − |
| 5 | − | +++ |
| 6 | + | +++ |
| 7 | ++ | ++ |
| 8 | + | ++ |
| 9 | + | ++ |
| 10 | − | +++ |

AXONS/NERVE: −=0; +=1-20; ++=20-50; +++=50->300

```
          10         20         30         40         50         60
    CTATCTCCTC TCTCAGCCGC TGCTTTTAAA GAACGTGAAT ACCTTGGTGA TTTACCAGCA
          70         80         90        100        110        120
    GTACTGCCCA CTGAAGGAAC ACTTCCAGCA ACTTCAAATG AAGCTTCTAA AGCATTCTCA
         130        140        150        160        170        180
    GAGAAGGCAA AAAATCCATT TGTAGAGAGA AATTTAACAG AATTTTCAGA ATTGGAATAT
         190        200        210        220        230        240
    TCAGAAATGG AATCATCATT CAGTGGCTCT CAAAAGGCAG AACCTGCCGT AACAGTAGCG
         250        260        270        280        290        300
    AATCCTAGGG ACGAAATAGT TGTGAGGAGT AGAGATAAAG AAGAGGACTT AGTTAGTCTT
         310        320        330        340        350        360
    AACATCCTTC ATACTCAGCA GGAGTTATCT ACAGTCCTTA CGAAATCAGT TGAAGAAGAA
         370        380        390        400        410        420
    GATAGAGTTC TGTCTCCAGA AAAAACAAAG GACAGTTTTA AGGAAAAGGG AGTTGCAGCA
         430        440        450        460        470        480
    GAAGCTTCTA TGGGGGAGGA ATATGCAGAC TTCAAACCAT TTGAGCGAGT ATGGGAAGTG
         490        500        510        520        530        540
    AAAGATACTT ACAAGCAAGA TAGTGATGTT TTGATTGCTG GAGGTAATAT AGAGAGCAAA
         550        560        570        580        590        600
    TTGGAAGGTA AAGTGGATAA GAAACACTTT TCAGATAGCC TTGAACAAAC AAATCGTGAA
         610        620        630        640        650        660
    AAAGATAGTG AAAGCAGTAA TGATGACACT TCATTTCCCA GTACACCAGA AGCTGTAAGA
         670        680        690        700        710        720
    GGTGGTTCCG GAGCGTACAT CACGTGTGCT CCCTTTAACC CAACAACTGA GAATGTTTCA
         730        740        750        760        770        780
    ACAAACATTT TTCCCTTGTT GGAAGATCAT ACTTCGGAAA ATAAGACAGA TGAAAAAAAG
         790        800        810        820        830        840
    ATAGAAAAAA AAAGGCACAA ATTGTAACAG AGAAGAATGC AAGTGTCAAG ACATCAAACC
         850        860        870        880        890        900
    CTTTCCTTAT GGCAGCACAG GAGTCTAAGA CAGATTACGT TACAACAGAT CATGTGTCAA
         910        920        930        940        950        960
    AGGTGACCGA GGAAGTAGTG GCAAACATGC CTGAAGGTCT AACCCCAGAT TTGGTTCAGG
         970        980        990       1000       1010       1020
    AAGCATGTGA AAGTGAATTG AATGAAGCTA CTGGTACAAA AATTGCCTTT GAAACAAAAA
        1030       1040       1050       1060       1070       1080
    TGGACCTGGT TCAAACTTCA GAAGCTGTGC AGGAGTCACT TTACCCTGTA ACACAGCTTT
        1090       1100       1110       1120       1130       1140
    GCCCATCTTT TGAAGAATCT GAAGCTACTC CGTCACCGGT TTTGCCTGAC ATTGTCATGG
        1150       1160       1170       1180       1190       1200
    AAGCACCATT AAATTCTGTA GTTCCTAGTG CTGGTGCTTC TGCAGTGCAG CTCAGTTCAT
        1210       1220       1230       1240       1250       1260
```

FIG.12A

```
CACCATTAGA AACTCTTCCT TCAGTTAATT ATGAAAGCAT AAAGTTTGAG CCTGAAAATC
    1270       1280       1290       1300       1310       1320
CCCCACCATA TGAGGAGGCC ATGAATGTAT CACTAAAAAA AGAATCAGGA ATGAATGAAG
    1330       1340       1350       1360       1370       1380
AAATCACAGA GCCTGAAGGT ATTAGTGTAG CTGTTCAGGA AACAGAAGCT CCTTATATAT
    1390       1400       1410       1420       1430       1440
CTATTGCATG TGATTTAATT AAAGAAACAA AGATCTCTAC TGAACCGACT CCAGATTTCT
    1450       1460       1470       1480       1490       1500
CTAGTTATTC AGAAATAGCA GAAGTTGCAC AGCCAGTGCC CGAGCATTCT GAGCTAGTTG
    1510       1520       1530       1540       1550       1560
AAGATTCCTC CCCCGATTCT GAACCAGTTG ACTTATTTAG TGATGATTCA ATACCCGAAG
    1570       1580       1590       1600       1610       1620
TTCCACAAAA ACAAGATGAA GCTGTAATAC TTGTGAAAGA AAACCTCACT GAAATTTCAT
    1630       1640       1650       1660       1670       1680
CTGAGTCAAT GACAGGACAT GACAATAAGG GAAAACTCAG TGCTTCACCA TCACCTGAGG
    1690       1700       1710       1720       1730       1740
GAGGAAAACC GTATTTGGAG TCTTTTCAGC CCAGTTTAGG CATCACAAAA GATACCTTAG
    1750       1760       1770       1780       1790       1800
CACCTGATGA AGTTTCAGCA TTGACCCAAA AGGAGAAAAT CCCTTTGCAG ATGGAGGAGC
    1810       1820       1830       1840       1850       1860
TCAATACTGC AGTTTATTCA AGTGATGGCT TATTCATTGC TCAGGAAGCA AACCTAAGAG
    1870       1880       1890       1900       1910       1920
AAAGTGAAAC ATTTTCAGAT TCATCTCCGA TTGAGATTAT AGATGAGTTC CCGACCTTTG
    1930       1940       1950       1960       1970       1980
TCAGTTCTAA AGCAGATTCT TCTCCTACAT TAGCCAGGGA ATACACTGAC CTAGAAGTAG
    1990       2000       2010       2020       2030       2040
CCCACAAAAG TGAAATTGCT GACATCCAGG ATGGAGCTGG GTCATTGGCT TGTGCAGGAT
    2050       2060       2070       2080       2090       2100
TGCCCCATGA CCTTTCTTTC AAGAGTATAC AACCTAAAGA GGAAGTTCAT GTCCCAGATG
    2110       2120       2130       2140       2150       2160
AGTTCTCCAA AGATAGGGGT GATGTTTCAA AGGTGCCCGT ACTGCCTCCA GATGTTTCTG
    2170       2180       2190       2200       2210       2220
CTTTGGATGC TCAAGCAGAG ATAGGCAGCA TAGAAAAACC CAAAGTTCTT GTGAAAGAAG
    2230       2240       2250       2260       2270       2280
CCGAGAGAAA ACTTCCTTCT GATACAGAAA AAGAGCGAAG ATCTCCATCT GCTATATTTT
    2290       2300       2310       2320       2330       2340
CAGCAGAGCT GAGTAAAACT TCAGTTGTTG ACCTCCTCTA CTGGAGAGAC ATTAAGAAGA
    2350       2360       2370       2380       2390       2400
CTGGAGTGGT GTTTGGTGCC AGCTTGTTCC TGCTGCTCTC GCTGACAGTA TTCAGCATTG
    2410       2420       2430       2440       2450       2460
```

FIG.12B

```
TGAGTGTAAC GGCCTACATT GCCTTGGCCC TGCTCTCTGT GACTATCAGC TTTAGGATAT
    2470       2480       2490       2500       2510       2520
ATAAGGGTGT GATCCAGGCT ATCCAGAAAT CTGATGAAGG CCACCCATTC AGGGCATATT
    2530       2540       2550       2560       2570       2580
TGGAATCTGA AGTTGCTATA TCTGAGGAGT TGGTTCAGAA GTACAGCAAT TCTGCTCTTG
    2590       2600       2610       2620       2630       2640
GTCATGTTAA CTGCACAATA AAAGAACTCA GACGCCTCTT CTTAGTTGAT GATTTAGTTG
    2650       2660       2670       2680       2690       2700
ATTCTCTGAA GTTTGCAGTG TTGATGTGGG TATTTACCTA TGTTGGTGCC TTGTTCAATG
    2710       2720       2730       2740       2750       2760
GTCTGACACT ACTAATTTTG GCTCTGATTT CACTCTTCAG TGTTCCTGTT ATTTATGAAC
    2770       2780       2790       2800       2810       2820
GGCATCAGGC GCAAATAGAT CATTATCTGG GACTTGCAAA TAAGAATGTT AAAGATGCTA
    2830       2840       2850       2860       2870       2880
TGGCTAAAAT CCAAGCAAAA ATCCCTGGAT TGAAGCGTAA AGCTGAATGA GAAAGCCTGA
    2890       2900       2910       2920       2930       2940
AAGAGTTAAC AATAGAGGAG TTTATCTTTA AAGGGGATAT TCATTTGATT CCATTGGGGA
    2950       2960       2970       2980       2990       3000
GGGTCAGGGA AGAACAAAGC CTTGACATTG CAGTGCAGTT TCACAGATCT TTATTTTTAG
    3010       3020       3030       3040       3050       3060
CAACGCAGTG TCTGAGGAAA AATGACCTGT CTTGACTGCC CTGTGTTCAT CATCTTAAGT
    3070       3080       3090       3100       3110       3120
ATTGTAAGCT GCTATGTATG GATTTAAATC GTAATCATAT TTGTTTTTCC TGTATGAGGC
    3130       3140       3150       3160       3170       3180
ACTGGTGAAT AAACAAAGAT CTGAGAAAGC TGTATATTAC ACTTTGTCGC AGGTAGTCTT
    3190       3200       3210       3220       3230       3240
GCTGTATTTG GGGAATTGCA AAGAAAGTGG AGCTGACAGA AATAACCCTT TTCACAGTTT
    3250       3260       3270       3280       3290       3300
GTGCACTGTG TACGGTCTGT GTAGGTTGAT GCAGATTTTC TGAAATGAAA TGTTTAGACG
    3310       3320       3330       3340       3350       3360
AGATCATGCC ACCAAGGCAG GAGTGAAAAA GCTTGCCTTT CCTGGTATGT TCTAGGTGTA
    3370       3380       3390       3400       3410       3420
TTGTGAAATT TACTGTTGTA TTAATTGCCA ATATAAGTAA ATATAGATTA TATATATCTA
    3430       3440       3450       3460       3470       3480
TATATAGTGT TTCACGAAGC TTAGCCCTTT ACCTTCCCAG CTGCCCCACA GTGCTTGATA
    3490       3500       3510       3520       3530       3540
CTTCTGTCAT GGGTTTTATG TGTGTAGTCC CAAAGCACAT AAGCTAGGGA GAAACGTACT
    3550       3560       3570       3580       3590       3600
TCTAGGCGCA CTACCATCTG TTTTCAACAC GAACCGACGC CATGCAAACA GAACTCCTCA
    3610       3620       3630       3640       3650       3660
ACATAAACTT CACTGCACAG ACTTACTGTA GTTAATTTTA TCACAAACTC TGGACTGAAT
    3670       3680       3690       3700       3710       3720
```

FIG.12C

```
CTAATGCTTC CAAAAATGTT TGCAAATATC AAACATTGTT ATGTAAGAAA ATATAAATGA
    3730       3740       3750       3760       3770       3780
CGATTTATAC AATTGTGGTT TAAGCTGTAT TGAACTAAAT CTGTGGAATG CATTGTGAAC
    3790       3800       3810       3820       3830       3840
TGTAAAAGCA AAGTATCAAT AAAGCTTATA GACTTAAAAA AAAAAAAAAA AAA.......
```

FIG. 12D

```
  1  MEDLDQSPLVSSS-DSPPRPQPAFKYQFVREPEDEE-EEEEE-EEEDEDE   50
     ||| |||  ||||| ||||||  |||||||| ||||||  |||||  |||  ||
  1  MEDIDQSSLVSSSTDSPPRPPPAFKYQFVTEPEDEEDEEEEEDEEED-DE   50

51  DLEELEVLERKPAAGLSAAPVPTAPAAGAPLMDFGNDFVPPAPRGPLPAA  100
     |||||||||||||||||||  ||  ||  ||| ||   || ||||||||||
 51  DLEELEVLERKPAAGLSAAAVPPA-AA-APLLDFSSDSVPPAPRGPLPAA  100

101  PPVAPERQPSWDPSPVSSTVPAPSPLS-AAAVSPSKLPEDDEPPARPPPP  150
     || |||||||||  ||    ||||  |  ||||  ||||||||||||||||
101  PPAAPERQPSWERSPAA---PAPS-LPPAAAVLPSKLPEDDEPPARPPPP  150

151  PPASVSPQAEPVWTPPAPAPAAPPSTPAAPKRRGS-SG-----AV-----  200
     ||| ||  |||     | || | ||||||||||||| |         |
151  PPAGASPLAEP-----A-AP--P-STPAAPKRRGSGSVDETLFALPAASE  200

201  -VXXXX--KIMDLKEQPGNTISAGQEDFPSVLLETAASXPSLSPLSAASF  250
      |||||    |||||  ||||| | ||||||||||||||||||||||||  ||
201  PVIPSSAEKIMDLMEQPGNTVSSGQEDFPSVLLETAASXPSLSPLSTVSF  250

251  KEHEYLGNLSTVLPTEGTLQE--NVSEASKEVSEKAKTLLID-RDLTEFS  300
     ||| ||||||| |   |||     |||||  |    ||| |   ||| |||
251  KEHGYLGNLSAVSSSEGTIEETLN--EASKELPERA-TNPFVNRDLAEFS  300

301  ELEYSEMGSSFSVSPKAESAVI-VANPREEIIVKNKDEEEKLV-SNNILH  350
     ||||||||||||  |||  |||   |  |  ||  ||  ||   ||  ||
301  ELEYSEMGSSFKGSPKGESA-ILVENTKEEVIVRSKDKED-LVCSAA-LH  350

351  XQQELPTALTKLV-KEDEVVSSEKAKDSFNEKR--VAVEAPMREEYADFK  400
     |  |       |  | |||  |  ||||     |   || ||||||||||
351  SPQESP------VGKEDRVVSPEKTMDIFNEMQMSV-V-APVREEYADFK  400

401  PFERVWEVKDSKEDS-DMLAAGGKIESNLESKVDKKCFADSLEQTNHEKD  450
     ||| |||||||   |  ||||||   |||||||||| ||||||||||  ||
401  PFEQAWEVKDTYEGSRDVLAARA----NVESKVDRKCLEDSLEQKSLGKD  450

451  SESSNDDTSFPSTPEGIKDRSGAYITCAPFNPAATESIAT-NIFPLLEDP  500
     ||  |  ||||||||| |||| |||||||  ||  |||  | |||||||||
451  SEGRNEDASFPSTPEPVKDSSRAYITCASFTSA-TEST-TANTFPLLEDH  500

501  TSENXTDEKKIEEKKAQIVTEKNTSTKTSNPFFVAAQDSETDYVTTDNLT  550
     |||||||||||||| ||||||||  || ||||||| ||||||| ||||||  |
501  TSENXTDEKKIEERKAQIITEK-TSPKTSNPFLVAVQDSEADYVTTDTLS  550

551  KVTEEVVANMPEGLTPDLVQEACESELNEVTGTKIAYETKMDLVQTSEVM  600
     ||||  | ||||||||||||||||||||| ||||||||||| |||||||| |
551  KVTEAAVSNMPEGLTPDLVQEACESELNEATGTKIAYETKVDLVQTSEAI  600
```

FIG.13A

```
601  QESLYPAAQLCPSFEESEATPSPVLPDIVMEAPLNSAVPSAGASVIQPSS  650
     |||||| |||||||||| |||||||||||||||||| |||||||| ||| 
601  QESLYPTAQLCPSFEEAEATPSPVLPDIVMEAPLNSLLPSAGASVVQPSV  650

651  SPLEASS-VNYESIKHEPENPPPYEEAMSVSLKVSGIKEEIKEPENINAA  700
     ||||| | | | ||||||||||||||||| | || ||| ||||| | || 
651  SPLEAPPPVSYDSIKLEPENPPPYEEAMNVALKALGTKEGIKEPESFMAA  700

701  LQETEAPYISIACDLIKETKLSAEPAPDFSDYSEMAKVEQPVPDHSELVE  750
     |||||||||||||||||||||| || ||||| ||||| || || |||||
701  VQETEAPYISIACDLIKETKLSTEPSPDFSNYSEIAKFEKSVPEHAELVE  750

751  DSSPDSEPVDLFSDDSIPDVPQKQDETVMLVKESLTETSFESMIEYENKE  800
     ||||| |||||||||||| ||| ||| ||| ||||| |  | |    ||
751  DSSPESEPVDLFSDDSIPEVPQTQEEAVMLMKESLTEVS-ETVAQH--KE  800

801  K-LSALPPEGGKPYLESFK--L-SLDNTKDTLLPDEVSTLSKKEKIPLQM  850
       |||  |  |||||||| ||    ||||||  |  | | ||||| |||
801  ERLSASPQELGKPYLESFQPNLHS---TKDAASNDIP-TLTKKEKISLQM  850

851  EELSTAVYSNDDLFISKEAQIRETETFSDSSPIEIIDEFPTLISSKTDSF  900
     || ||| ||||||| ||| |  ||||||||||||||||||  ||| | | 
851  EEFNTAIYSNDDLSSSKEDKIKESETFSDSSPIEIIDEFPTFVSAKDDSP  900

901  SKLAREYTDLEVSHKSEIANAPDGAGSLPCTELPHDLSLKNIQPKVEEKI  950
      |||||||||||| ||||||| |  |||||||| |||||| ||| ||| |
901  -KLAKEYTDLEVSDKSEIANIQSGADSLPCLELPCDLSFKNIYPKDEVHV  950

951  SFSDDFSKNGSATSKVLLLPPDVSALGHTQAEIESIVKPKVLEKEAEKKL 1000
     |  | || |  || |||| |||| ||||  | || |||||||| |||||
951  S--DEFSENRSSVSKASISPSNVSALEP-QTEMGSIVKSKSLTKEAEKKL 1000

1001 PSDTEKEDRSPSAIFSADLGKTSVVDLLYWRDIKKTGVVFGASLFLLLSL 1050
     |||||||||| |||||| ||||||||||||||||||||||||||||||||
1001 PSDTEKEDRSLSAVLSAELSKTSVVDLLYWRDIKKTGVVFGASLFLLLSL 1050

1051 TVFSIVSVTAYIALALLSVTISFRIYKGVIQAIQKSDEGHPFRAYLESEV 1100
     ||||||||||||||||||||||||||||||||||||||||||||||||||
1051 TVFSIVSVTAYIALALLSVTISFRIYKGVIQAIQKSDEGHPFRAYLESEV 1100

1101 AISEELVQKYSNSALGHVNCTIKELRRLFLVDDLVDSLKFAVLMWVFTYV 1150
     ||||||||||||||||||| ||||||||||||||||||||||||||||||
1101 AISEELVQKYSNSALGHVNSTIKELRRLFLVDDLVDSLKFAVLMWVFTYV 1150

1151 GALFNGLTLLILALISLFSVPVIYERHQAQIDHYLGLANKNVKDAMAKIQ 1200
     |||||||||||||||||||||||||||| ||||||||||||| |||||||
1151 GALFNGLTLLILALISLFSIPVIYERHQVQIDHYLGLANKSVKDAMAKIQ 1200

1201 AKIPGLKRKAE....................................... 1250
     ||||||||||
1201 AKIPGLKRKAD....................................... 1250
```

FIG.13B

```
  1 CAG GCT TAG TCT GGG GAA GCG GGT GTT TCA TGT CTC AGG GAG
      Q   A   -   S   G   E   A   G   V   S   C   L   R   E

43 AAT TTT GCA GTT TAC AGC GTT TCT GTT GGT ATG CAT AAT TTG
      N   F   A   V   Y   S   V   S   V   G   M   H   N   L
                                                  START
 85 TAA TTG CTG CTG GAG GGC AGA TCG TGG CAA GAA ATG GAC GGA
      -   L   L   L   E   G   R   S   W   Q   E   M   D   G

127 CAG AAG AAA CAT TGG AAG GAC AAG GTT GTT GAC CTC CTC TAC
      Q   K   K   H   W   K   D   K   V   V   D   L   L   Y

169 TGG AGA GAC ATT AAG AAG ACT GGA GTG GTG TTT GGT GCC AGC
      W   R   D   I   K   K   T   G   V   V   F   G   A   S

211 TTA TTC CTG CTG CTG TCT CTG ACA GTG TTC AGC ATT GTC AGT
      L   F   L   L   L   S   L   T   V   F   S   I   V   S

253 GTA ACG GCC TAC ATT GCC TTG GCC CTG CTC TCG GTG ACT ATC
      V   T   A   Y   I   A   L   A   L   L   S   V   T   I

295 AGC TTT AGG ATA TAT AAG GGC GTG ATC CAG GCT ATC CAG AAA
      S   F   R   I   Y   K   G   V   I   Q   A   I   Q   K

337 TCA GAT GAA GGC CAC CCA TTC AGG GCA TAT TTA GAA TCT GAA
      S   D   E   G   H   P   F   R   A   Y   L   E   S   E

379 GTT GCT ATA TCA GAG GAA TTG GTT CAG AAA TAC AGT AAT TCT
      V   A   I   S   E   E   L   V   Q   K   Y   S   N   S

421 GCT CTT GGT CAT GTG AAC AGC ACA ATA AAA GAA CTG AGG CGG
      A   L   G   H   V   N   S   T   I   K   E   L   R   R

463 CTT TTC TTA GTT GAT GAT TTA GTT GAT TCC CTG AAG TTT GCA
      L   F   L   V   D   D   L   V   D   S   L   K   F   A

505 GTG TTG ATG TGG GTG TTT ACT TAT GTT GGT GCC TTG TTC AAT
      V   L   M   W   V   F   T   Y   V   G   A   L   F   N

547 GGT CTG ACA CTA CTG ATT TTA GCT CTG ATC TCA CTC TTC AGT
      G   L   T   L   L   I   L   A   L   I   S   L   F   S
```

FIG. 14A

```
589  ATT CCT GTT ATT TAT GAA CGG CAT CAG GTG CAG ATA GAT CAT
      I   P   V   I   Y   E   R   H   Q   V   Q   I   D   H

631  TAT CTA GGA CTT GCA AAC AAG AGT GTT AAG GAT GCC ATG GCC
      Y   L   G   L   A   N   K   S   V   K   D   A   M   A

673  AAA ATC CAA GCA AAA ATC CCT GGA TTG AAG CGC AAA GCA GAT
      K   I   Q   A   K   I   P   G   L   K   R   K   A   D

STOP
715  TGA AAA AGC CCC AAA CAG AAG TTC ATC TTT AAA GGG GAC ACT
      -   K   S   P   K   Q   K   F   I   F   K   G   D   T

757  CAC TTG ATT ACG GGG GTG GGA GGT CAG GGG TGA GCC CTT GGT
      H   L   I   T   G   V   G   G   Q   G   -   A   L   G

799  GGC CGT GCG GTT TCA GCT CTT TAT TTT TAG CAG TGC ACT GTT
      G   R   A   V   S   A   L   Y   F   -   Q   C   T   V

841  TGA GGA AAA ATT ACC TGT CTT GAC TTC CTG TGT TTA TCA TCT
      -   G   K   I   T   C   L   D   F   L   C   L   S   S

883  TAA GTA TTG TAA GCT GCT GTG TAT GGA TCT CAT TGT AGT CAC
      -   V   L   -   A   A   V   Y   G   S   H   C   S   H

925  ACT TGT CTT CCC CAA TGA GGC GCC TGG TGA ATA AAG GAC TCG
      T   C   L   P   Q   -   G   A   W   -   I   K   D   S

967  GGG AAA GCT GTG CAT TGT ATC TGC TGC AGG GTA GTC TAG CTG
      G   K   A   V   H   C   I   C   C   R   V   V   -   L

1009 TAT GCA GAG AGT TGT AAA GAA GGC AAA TCT GGG GGC AGG GAA
      Y   A   E   S   C   K   E   G   K   S   G   G   R   E

1051 AAC CCT TTT CAC AGT GTA CTG TGT TTG GTC AGT GTA AAA CTG
      N   P   F   H   S   V   L   C   L   V   S   V   K   L

1093 ATG CAG ATT TTT CTG AAA TGA AAT GTT TAG ATG AGA GCA TAC
      M   Q   I   F   L   K   -   N   V   -   M   R   A   Y

1135 TAC TAA AGC AGA GTG GAA AAC TCT GTC TTT ATG GTG TGT TCT
      Y   -   S   R   V   E   N   S   V   F   M   V   C   S
```

FIG.14B

```
1177  AGG TGT ATT GTG AAT TTA CTG TTA TAT TGC CAA TAT AAG TAA
       R   C   I   V   N   L   L   L   Y   C   Q   Y   K   -

1219  ATA TAG ACC TAA TCT ATA TAT AGT GTT TCA CAA AGC TTA GAT
       I   -   T   -   S   I   Y   S   V   S   Q   S   L   D

1261  CTT TAA CCT TGC AGC TGC CCC ACA GTG CTT GAC CTC TGA GTC
       L   -   P   C   S   C   P   T   V   L   D   L   -   V

1303  ATT GGT TAT GCA GTG TAG TCC CAA GCA CAT AAA CTA GGA AGA
       I   G   Y   A   V   -   S   Q   A   H   K   L   G   R

1345  GAA ATG TAT TTG TAG GAG TGC TAC CTA CCA CCT GTT TTC AAG
       E   M   Y   L   -   E   C   Y   L   P   P   V   F   K

1387  AAA ATA TAG AAC TCC AAC AAA AAT ATA GAA TGT CAT TTC AAA
       K   I   -   N   S   N   K   N   I   E   C   H   F   K

1429  GAC TTA CTG TAT GTA TAG TTA ATT TTG TCA CAG ACT CTG AAA
       D   L   L   Y   V   -   L   I   L   S   Q   T   L   K

1471  TTC TAT GGA CTG AAT TTC ATG CTT CCA AAT GTT TGC AGT TAT
       F   Y   G   L   N   F   M   L   P   N   V   C   S   Y

1513  CAA ACA TTG TTA TGC AAG AAA TCA TAA AAT GAA GAC TTA TAC
       Q   T   L   L   C   K   K   S   -   N   E   D   L   Y

1555  CAT TGT GGT TTA AG
       H   C   G   L
```

FIG.14C

METHODS OF MAKING ANTIBODIES THAT BIND NOGO

This application is a continuation of U.S. patent application Ser. No. 09/830,972 filed Sep. 24, 2001, which is the national stage of international patent application no. PCT/US99/26160 filed Nov. 5, 1999, which claims benefit under 35 U.S.C. 0 119(e) of United States provisional application No. 60/107,446 filed Nov. 6, 1998, all of which are incorporated herein by reference in their entireties.

1. INTRODUCTION

The present invention relates to the gene, Nogo, and in particular to Nogo, its encoded protein products, as well as derivatives and analogs thereof. Production of Nogo proteins, derivatives, and antibodies is also provided. The invention further relates to therapeutic compositions and methods of diagnosis and therapy.

2. BACKGROUND OF THE INVENTION

In the central nervous system (CNS) of higher vertebrates, regeneration of axons after injury is almost absent and structural plasticity is limited. Growth inhibitors associated with CNS myelin are likely to play an important role. This is evidenced by a monoclonal antibody (mAb), IN-1, that neutralizes a potent neurite growth inhibitory myelin protein, thereby promoting long-distance axonal regeneration and enhancing compensatory plasticity following spinal cord or brain lesions in adult rats.

A number of in vitro and in vivo observations have revealed a new aspect of neurite growth regulation which is the presence of repulsive and inhibitory signals and factors (Keynes and Cook, 1995, Curr. Opin. Neurosci. 5:75-82). Most of these signals seemed to be proteins or glycoproteins. A first breakthrough towards identification of the factors was the purification and cDNA cloning of a chick brain-derived growth cone collapse inducing molecule, Collapsin-1, now called Semaphorin 3A.

A second group of repulsive guidance cues recently purified and cloned is now designated as Ephrins. They are ligands for the Eph receptor tyrosine kinase family. Ephrin-A5 and Ephrin-A2 are expressed as gradients in the optic tectum of the chick embryo, and their ectopic expression or deletion causes guidance errors of ingrowing retinal axons. Like the Semaphorins, the Ephrin family has 15 to 20 members, each with a complex and dynamic expression in and outside of the nervous system. The functions of most of these molecules remain to be analyzed.

A third group of guidance cues which can repulse growing axons and is expressed in the developing nervous system are the Netrins. Netrin has been purified as a floor plate derived chemoattractant for commissural axons in early spinal cords, like its *C. elegans* ortholog unc-6. Netrin-1 turned out to have repulsive effects for certain types of neurons depending on the type of receptor present on the target neuronal growth cones (Tessier-Lavigne et al., 1996, Science 274:1123-33).

Previously, a potent neurite growth inhibitory activity associated with adult CNS oligodendrocytes and myelin was reported by Canoni and Schwab (1988, J. Cell Biol. 106: 1281-1288). A major constituent is a high molecular weight membrane protein (NI-250, with a smaller component, NI-35, in rat) which was recently purified, and which is related to the subject of the present invention, and is bound by the neutralizing mAb, IN-1 (Canoni and Schwab, 1988, J. Cell Biol. 106:1281-1288; U.S. Pat. Nos. 5,684,133; 5,250,414; PCT Publication WO 93/00427).

Myelin-associated neurite growth inhibitors play a crucial role in preventing regeneration of lesioned CNS axons. When oligodendrocyte development and myelin formation is blocked in chicken or rats, the regeneration permissive period following CNS lesions is prolonged. Indeed, myelin formation coincides in time with the end of the developmental period where the CNS shows high structural plasticity and a high potential for regeneration.

NI-250 and NI-35 are likely to be major components of the myelin-associated growth inhibition as evidenced by in vivo application of IN-1 to spinal cord lesioned adult rats which induced regeneration of corticospinal axons over long distances and allowed motor and behavior functional recovery especially with regard to locomotion. Similar experiments on the optic nerve and the cholinergic septo-hippocampal pathway also demonstrated the in vivo relevance of the IN-1 recognized antigen, NI-35/250 (Schnell and Schwab, 1990, Nature 343:269-272; Bregman et al., 1995, Nature 378:498-501).

Unlesioned fiber systems also respond to the neutralization of neurite growth inhibitors by IN-1. Recent experiments have conclusively shown that following a selective corticospinal tract lesion (pyramidotomy), intact fibers sprout across the midline in the spinal cord and brainstem and establish a bilateral innervation pattern, accompanied by an almost full behavioral recovery of precision movements in the presence of IN-1 (Z'Graggen et al., 1998, J. Neuroscience 18(12): 4744-4757).

Isolation of the gene that encodes the neurite growth inhibitory protein provides multiple opportunities for developing products useful in neuronal regeneration and in treatment of various neurological disorders, including CNS tumor.

Citation of a reference hereinabove shall not be construed as an admission that such reference is available as prior art to the present invention.

3. SUMMARY OF THE INVENTION

The present invention relates to nucleotide sequences of Nogo genes (human, rat and bovine Nogo and Nogo homologs of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the Nogo protein is a rat, bovine or human protein.

The invention also relates to a method of identifying genes which interact with Nogo.

Nogo is a gene provided by the present invention, identified by the method of the invention, that both encodes and interacts with neural growth regulatory proteins.

The invention also relates to Nogo derivatives and analogs of the invention which are functionally active, i.e., they are capable of displaying one or more known functional activities associated with a naturally occurring Nogo protein. For example, a major inhibitory region between amino acids 542 to 722 have been identified. Such functional activities include, but are not limited to, neurite growth inhibition of neural cells, spreading and migration of fibroblasts, or any cell exhibiting neoplastic growth, the ability to interact with or compete for interaction with neural growth regulatory proteins, antigenicity which is the ability to bind (or compete with Nogo for binding) to an anti-Nogo antibody, immunogenicity which is the ability to generate antibody which binds to Nogo. These antibodies having the potential to induce neurite outgrowth or prevent dorsal root ganglia growth cone collapse by inhibiting the function of Nogo, and functional fragments or derivatives of Nogo, with the ability to inhibit neurite outgrowth.

The invention further relates to fragments (and derivatives and analogs thereof) of Nogo which comprise one or more domains of a Nogo protein such as the acidic and proline rich amino terminus (e.g., at amino acids 31 to 58 of SEQ ID NO:2), the highly conserved carboxy terminus, and two hydrophobic stretches of 35 and 36 amino acids length in rat Nogo, also in the carboxy terminus (e.g., at amino acids 988 to 1023, and at 1090 to 1125 of SEQ ID NO:2).

Antibodies to the various Nogo, and Nogo derivatives and analogs, are additionally provided. In particular, by way of example, two antibodies have been derived, the first antibody, termed AS 472, was derived using as immunogen a synthetic peptide corresponding to amino acids 623 to 640 of SEQ ID NO:2, and the second antibody, termed AS Bruna, was generated against the carboxy-terminus, amino acids 762 to 1163 of SEQ ID NO:2, of Nogo.

Methods of production of the Nogo proteins, derivatives and analogs, e.g., by recombinant means, are also provided.

The present invention also relates to therapeutic and diagnostic methods and compositions based on Nogo proteins and nucleic acids. Therapeutic compounds of the invention include but are not limited to Nogo proteins and analogs and derivatives (including fragments) thereof; antibodies thereto; nucleic acids encoding the Nogo proteins, analogs, or derivatives; and Nogo ribozymes or Nogo antisense nucleic acids.

The present invention also relates to therapeutic and diagnostic methods and compositions based on Nogo proteins and nucleic acids and anti-Nogo antibodies. The invention provides for treatment of CNS and neural derived tumors by administering compounds that promote Nogo activity (e.g., Nogo proteins and functionally active analogs and derivatives including fragments thereof; nucleic acids encoding the Nogo proteins, analogs, or derivatives, agonists of Nogo).

The invention also provides for treatment of diseases, disorders or damage which ultimately result in damage of the nervous system; such diseases, disorders or damage include, but are not limited to, central nervous system (CNS) trauma, (e.g. spinal cord or brain injuries), infarction, infection, malignancy, exposure to toxic agents, nutritional deficiency, paraneoplastic syndromes, and degenerative nerve diseases (including but not limited to Alzheimer's disease, Parkinson's disease, Huntington's Chorea, multiple sclerosis, amyotrophic lateral sclerosis, and progressive supra-nuclear palsy); by administering compounds that interfere with Nogo activity (e.g., a dominant negative Nogo derivative; antibodies to Nogo; anti-sense nucleic acids of Nogo; Nogo ribozymes or chemical groups that bind an active site of Nogo).

Animal models, diagnostic methods and screening methods for predisposition to disorders, and methods to identify and evaluate Nogo agonists and antagonists, are also provided by the invention.

The invention also provides a purified protein comprising a fragment of a Nogo protein comprising an amino acid sequence selected from the group consisting of residues 31-57 depicted in FIG. 2*a* (SEQ ID NO:2), residues 11-191 depicted in FIG. 14 (SEQ ID NO:32), residues 988-1023 depicted in FIG. 2*a* (SEQ ID NO:2), residues 1090-1125 depicted in FIG. 2*a* (SEQ ID NO:2), residues 994-1174 depicted in FIG. 13 (SEQ ID NO:29), residues 977-1012 depicted in FIG. 13 (SEQ ID NO:29), and residues 1079-1114 depicted in FIG. 13 (SEQ ID NO:29).

3.1 DEFINITIONS

As used herein, underscoring or italicizing the name of a gene shall indicate the gene, in contrast to its encoded protein product which is indicated by the name of the gene in the absence of any underscoring or italicizing. For example, "Nogo" shall mean the Nogo gene, whereas "Nogo" shall indicate the protein product of the Nogo gene.

4. DESCRIPTION OF THE FIGURES

FIG. 1*a*-1*b*: (a) Nogo cDNA clones: CWP1-3 is a bovine cDNA clone isolated from the screening of a bovine spinal cord white matter cDNA library with degenerated oligonucleotides MSC5-8 (pooled) and MSC9. Complementary RNA derived from this clone was used for subsequent rat cDNA library screening. Oli3 and Oli18 are isolated from an oligo d(T)-primed rat oligodendrocyte library. R1-3U21, RO18U1 and RO18U37-3 are isolated from a hexanucleotides-primed rat brain stem/spinal cord library (Stratagene). The positions of the 6 bovine NI220 (bNI220) peptide sequences are indicated on CWP1-3 and R13U21. Sequences at the junctions of different exons are marked on top of each clone. The question marks indicated on RO18U1 identify the sequence on this clone which does not match sequences from any other Nogo clones. RO18U37-3 was sequenced-only from the 5'-end, and the unsequenced portion is represented by dots. (b) Schematics demonstrating the hypothetical mechanism for the generation of three Nogo transcripts. P1 and P2 represent the putative location of the alternative promoters. The minimum number of three exons is required for generating the three transcripts as shown schematically, although each exon could potentially be split into multiple exons.

FIG. 2A1 to 2A4: Nucleotide (SEQ ID NO:1) and amino acid sequences (SEQ ID NO:2) of Nogo transcript A (sequence generated by connecting RO18U37-3, Oli18, and R1-3U21 cDNA sequences). Oval box: presumed initiation codon; underlined with dots: acidic stretch; □: potential PKC sites; Δ: potential casein kinase II sites; thick underline: carboxy terminal hydrophobic regions and potential transmembrane domains; thin underline: potential N-glycosylation sites. 2B: Peptide sequence comparison between sequenced, purified bovine NI220 (bNI220; SEQ ID NOS:3-8), and the corresponding bovine (SEQ ID NOS:9-14) and rat (SEQ ID NOS:15-20) sequences translated from rat and bovine cDNAs. Rat and bovine amino acid sequences, which do not match the bNI220 peptide sequences, are in lower case.

FIG. 3*a*-3*b*: (a) Amino acid sequence comparison of the carboxy terminal 180 amino acid common regions of NSP (human; SEQ ID NO:21), S-REX (rat)(SEQ ID NO:22), CHS-REX (chicken; SEQ ID NO:23), NOGOBOV (bovine; SEQ ID NO:24), NOGORAT (rat; SEQ ID NO:25), a *C. elegans* EST clone (WO6A7A; SEQ ID NO:26), and a *D. melanogaster* EST clone (US51048; SEQ ID NO:27). (b) Evolutionary conservation of the two hydrophobic regions. Percent similarities within and across species of the common hydrophobic regions are shown. Shaded letters: conserved amino acids.

Figure 4A:
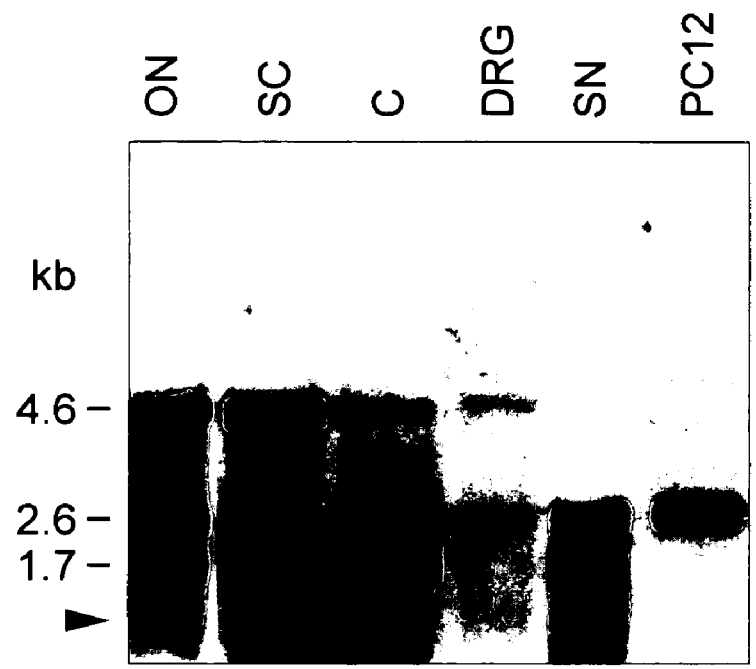
Figure 4B:
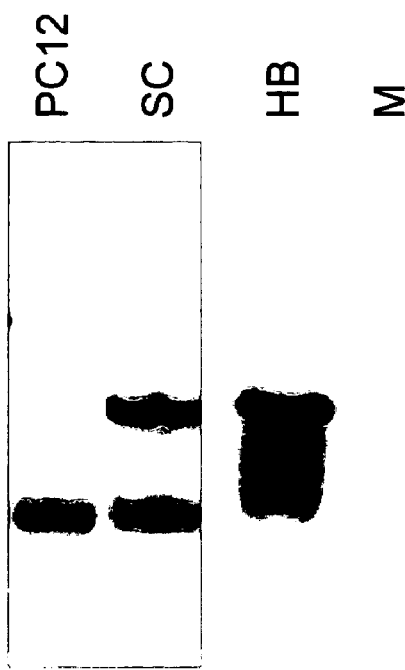
Figure 4C:
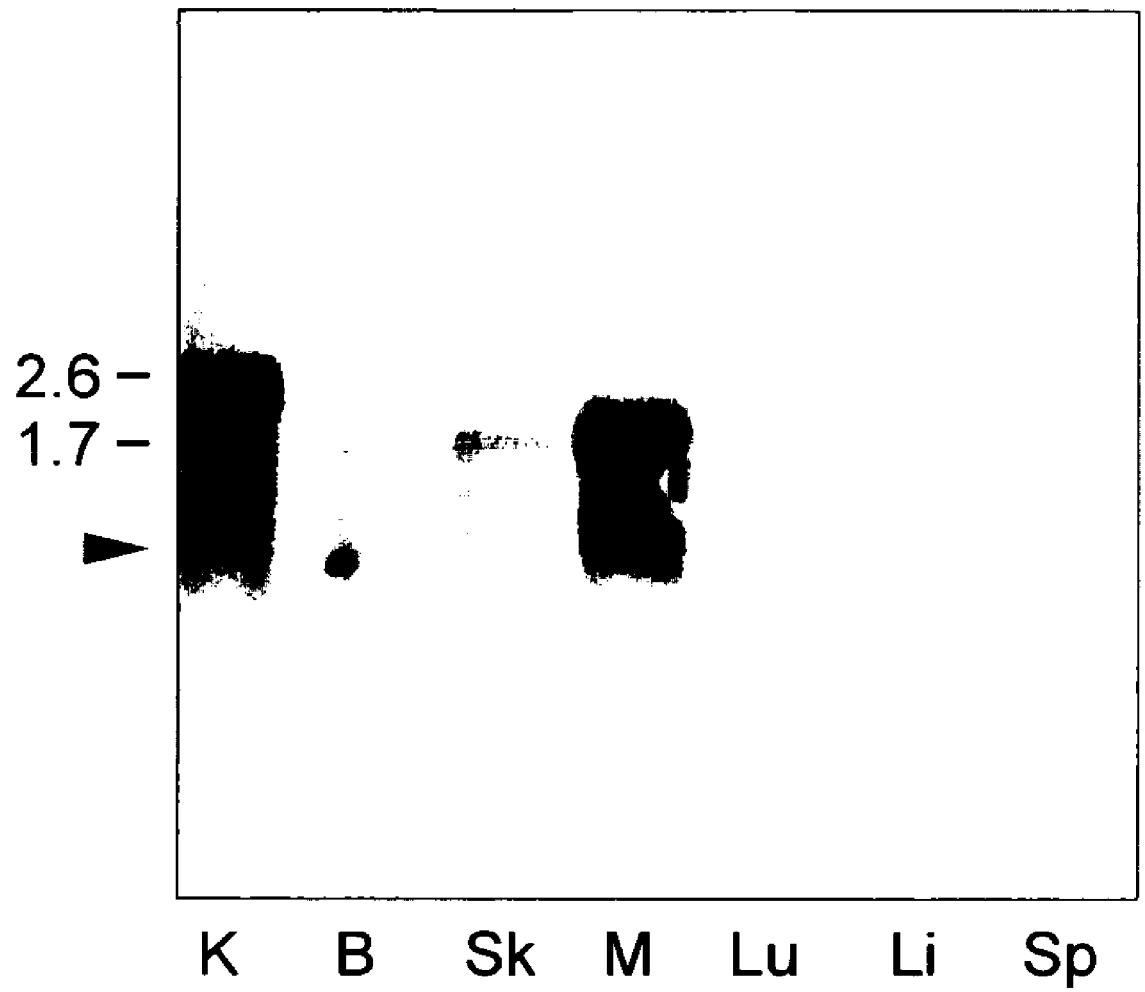

FIG. 4*a*-4*c*: (a) Northern hybridization of various tissues with the Nogo common probe. The common probe contains transcript A sequence between nucleotides 2583-4678. ON, optic nerve; SC, spinal cord; C, cerebral cortex; DRG, dorsal root ganglia; SN, sciatic nerve; PC12, PC12 cell line. (b) Northern hybridization of spinal cord and PC12 cells RNAs with an exon 1-specific probe (left panel) and of hindbrain (HB) and skeletal muscle (M) RNAs with an exon 2 specific probe (right panel). (c) Northern hybridization with the Nogo common probe. K, kidney; B, cartilage (from breastbone); Sk, skin; M, skeletal muscle; Lu, lung; Li, liver; Sp, spleen. The three major transcripts are marked (4.6 kilobases (kb), 2.6 kb, and 1.7 kb). Δ: a diffuse but consistent band about 1.3 kb in size.

FIG. 5a-5f: In situ hybridization of adult rat spinal cord and cerebellum sections. (a, d) Rows of oligodendrocytes (OL) in spinal cord and cerebellum white matter, respectively, can be seen labeled by the Nogo antisense "common" riboprobe. This is very similar to the signals detected when a consecutive spinal cord section was hybridized to an antisense plop riboprobe (b). (c) Neurons in grey matter (GM) were also labeled by the Nogo antisense "common" riboprobe. WM: white matter. Bright field and fluorescent view, respectively, of a cerebellum section double labeled with the Nogo antisense "common" riboprobe (e) and of an anti-GFAP antibody (f). Purkinje cells (double arrowheads) are strongly labeled with the Nogo probe, while astrocytes (arrowheads, black and white) are negative. A few cells in the granular cell layer (Gr) are also labeled with the Nogo probe, m: molecular layer. Scale bar: a, b, d-f: 50 p.m; c: 280 p.m.

FIG. 6a-6i: In situ hybridization of optic nerves at different postnatal days (a,f: P0; b,g: P3; c,h: P7; d,e,i: P22) with either Nogo or plp (antisense or sense) probes. (a-d) Nogo antisense probe; (e) Nogo sense probe; (g-i) plp antisense probe; (f) plp sense probe. Nogo expression in oligodendrocyte precusors can be detected as early as P0, while plp expression was only beginning to be detectable in P3 optic nerves close to the chiasm (g).

Figure 7A:
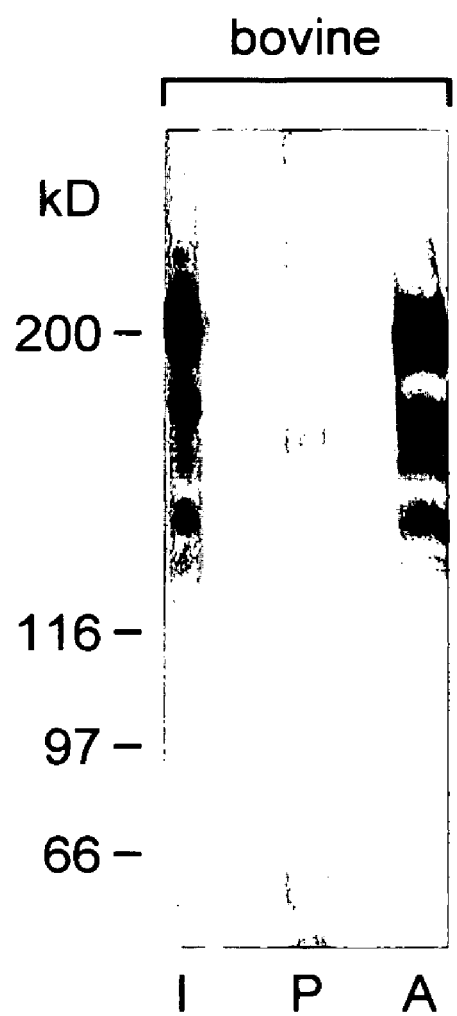
Figure 7B:
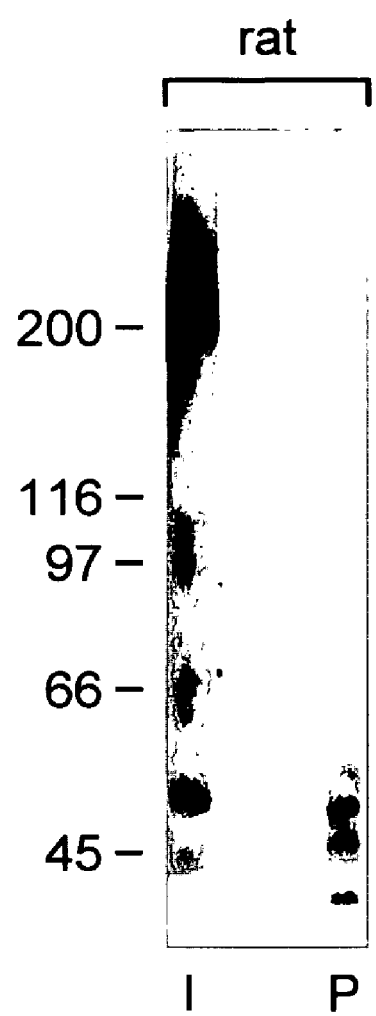
Figure 8C:
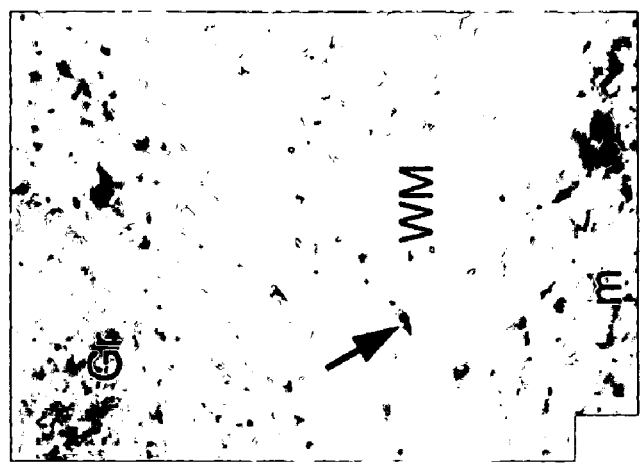
Figure 8B:
Figure 8A:
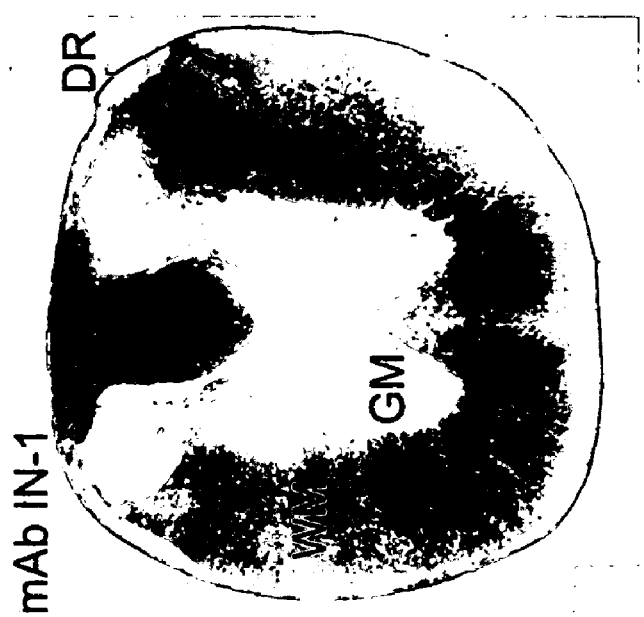
Figure 8F:
Figure 8E:
Figure 8D:
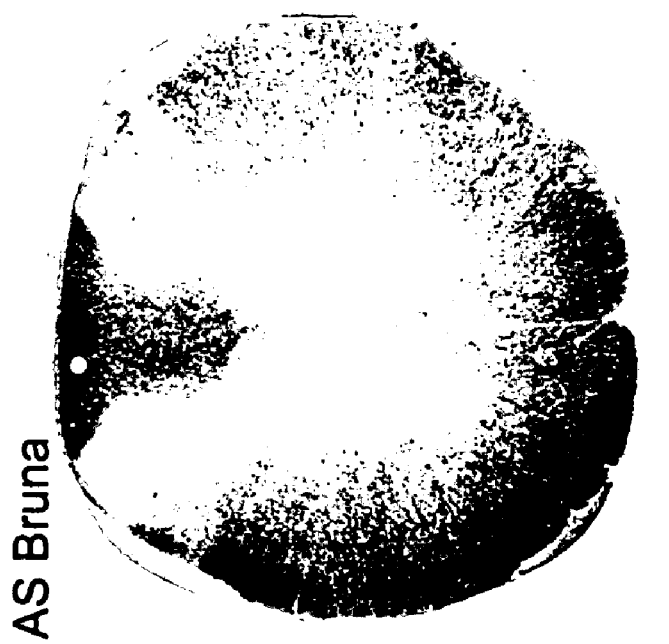
Figure 8G:
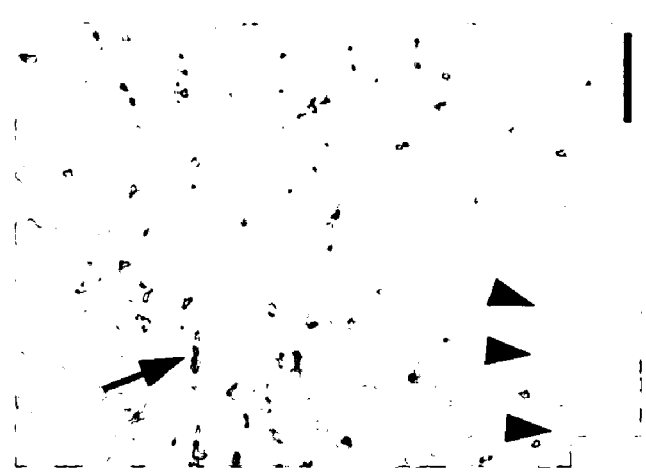
Figure 8H:
Figure 8I:

FIG. 7: AS Bruna and AS 472 both recognize a myelin protein of about 200 kD. Rat myelin extract and bovine q-pool were prepared according to Spillmann et al, 1998, J. Biol. Chem., 273(30):19283-19293. AS Bruna and AS 472 each recognized a 200 kD band as well as several lower bands in bovine myelin, which may be breakdown products of bNI220. AS Bruna stained a band 200 kD in rat myelin. I: AS Bruna; P: AS Bruna, preimmune serum; E: AS 472 affinity purified.

FIGS. 8a-8i: Immunohistochemistry on rat spinal cord and cerebellum using IN-1 (a-e), AS Bruna (d-f), and AS 472 (g-i), as indicated at the left of each panel. A strong myelin staining was observed in both tissues with all three antibodies when the frozen sections were fixed with ethanol/acetic acid (a, b, d, e, g, h). Treatment of the sections with methanol abolished the myelin staining except for oligodendrocyte cell bodies (arrows; c, f, i). Arrowheads: Purkinje cells, WM, white matter; GM, grey matter, DR: dorsal root; Gr, granular cell layer; m, molecular layer. Scale bar: a, d, g: 415 μm; b, c, e, f, h, i: 143 μm.

FIG. 9a-9d: Neutralizing activity of AS 472 and AS Bruna in different bioassays. (a) the NIH 3T3 fibroblasts were plated on cell culture dishes coated with q-pool and pre-treated with IN-1, AS Bruna, AS 472 or the corresponding pre-immune sera. Both polyclonal sera showed even a slightly better neutralization of the inhibitory substrate than IN-1. The pre-immune sera had no significant effect on the spreading of the NIH 3T3 cells. Addition of an excess of the peptide (P472) that was used to raise AS 472 competed the neutralizing activity whereas an unspecific peptide (Px) had no effect. (b) Pre-treatment of the inhibitory substrate with AS Bruna or AS 472 resulted in DRG neurite outgrowth comparable to what can be observed on a laminin substrate. Examples for neurite outgrowth from DRG on q-pool pre-treated with PBS (c; score=0) and pretreated with AS Bruna (d; score=4).

FIG. 10a-10d: Injection of optic nerve explants with AS 472 results in ingrowth of axons. (a) Pairs of adult rat optic nerves were dissected, injected with AS 472 or preimmune serum and placed into chamber cultures such that one end of the nerves was in contact with dissociated P0 rat DRG neurons. (b) After two weeks in vitro, EM sections of the nerves were taken at 3.5 mm from the cut site (arrows in A) and systematically screened for intact axons (3 experiments). (c) Regenerated axon bundles (arrows) grow through degenerating AS 472 injected optic nerve. (d) Regenerating axons in contact with myelin. Magnification: c, 12,000×; d, 35,000×.

Figure 11A:
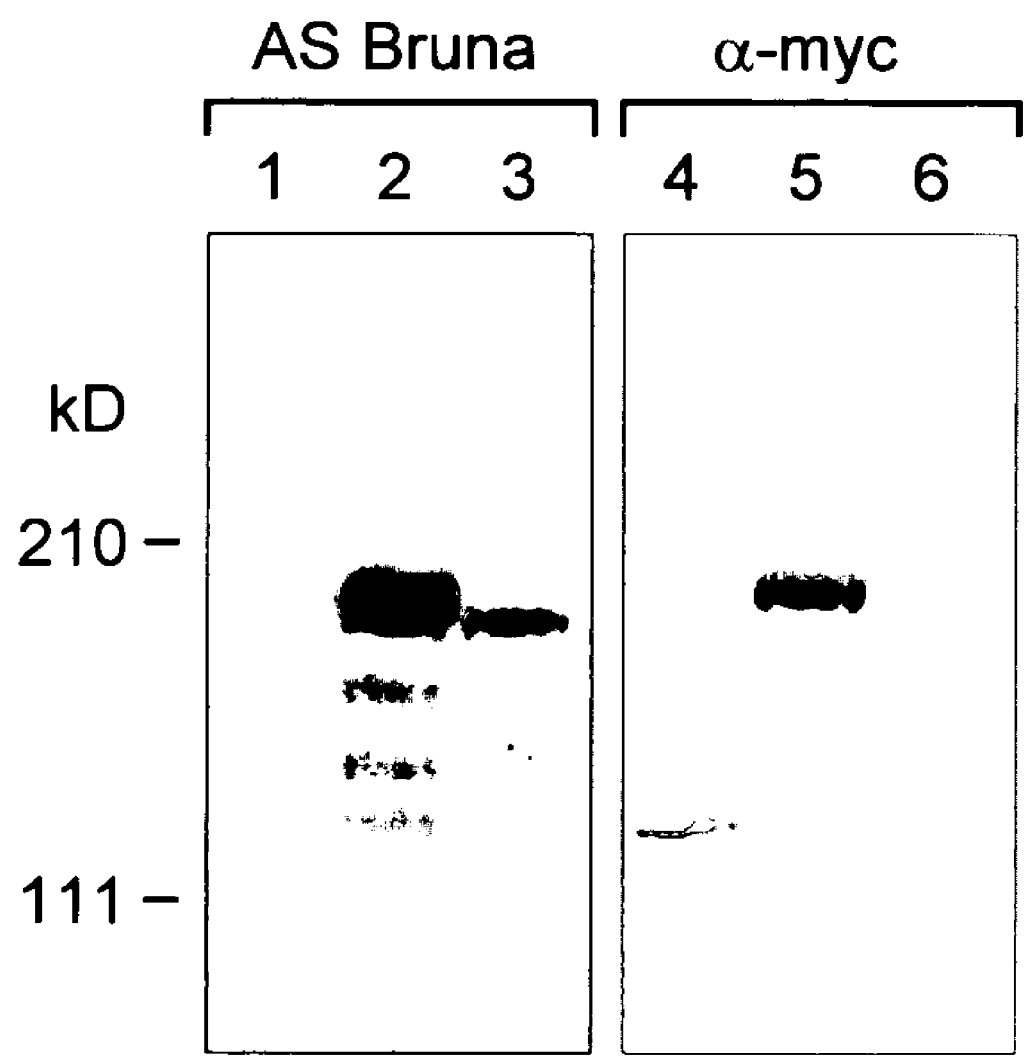
Figure 11B:
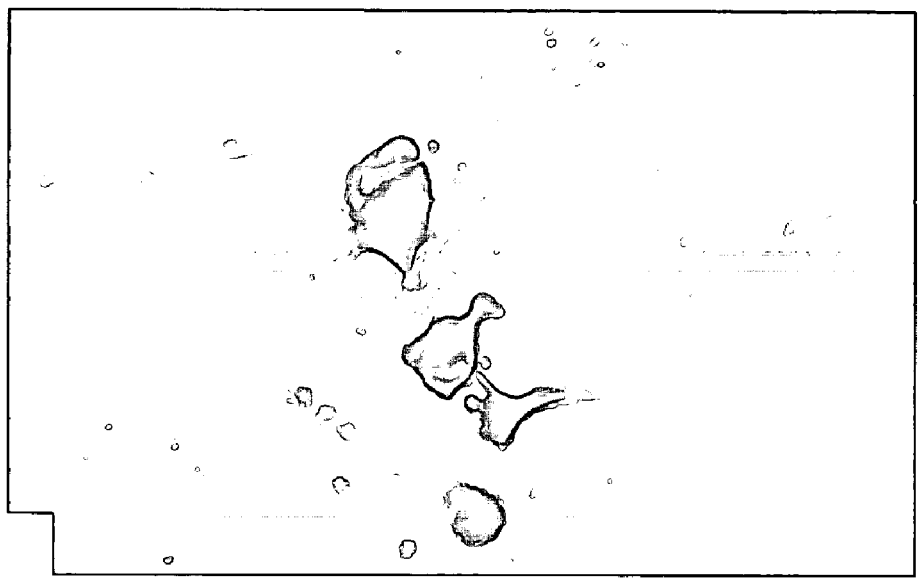
Figure 11C:
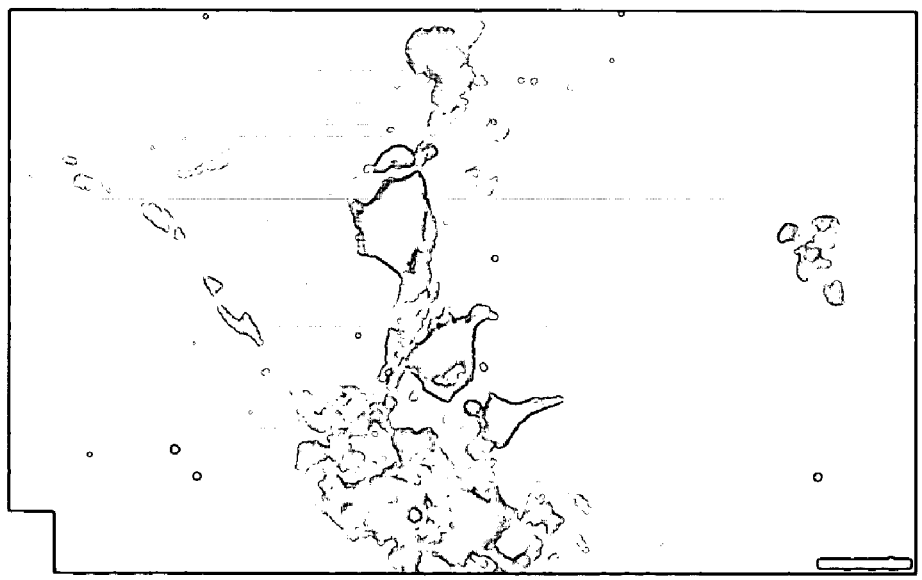

FIG. 11a-11c: Recombinant Nogo A expression in transfected COS cells. (a) Western blot showing immunoreactivity of AS Bruna to recombinant Nogo A (lane 2) and endogenous Nogo A from primary cultured rat oligodendrocytes (lane 3). The mobilities of these two proteins are virtually identical at about 200 kD on a 5% denaturing SDS gel. A control LacZ construct transfected sample (lane 1) showed no immunoreactivity with AS Bruna. The same blot was also probed with anti-myc antibody, 9E10, as indicated. The band that reacted with AS Bruna also reacted with the anti-myc tag antibody, 9E10 (lane 5), while the endogenous Nogo A did not (lane 6). The LacZ control transfection sample showed the expected band at about 118 kD (lane 4). COS cells transiently transfected with a Nogo A construct were double stained with AS Bruna (b) and IN-1 (c). Cells positively stained with AS Bruna were also positive with IN-1.

FIG. 12A to 12D: The nucleotide sequence (SEQ ID NO:28) of the bovine Nogo cDNA.

FIG. 13A-13B: The amino acid sequence of rat Nogo A (SEQ ID NO:2) aligned with the theoretical amino acid sequence of human Nogo (SEQ ID NO:29). The human Nogo amino acid sequence was derived from aligning expressed sequence tags (EST) to the rat Nogo sequence and translating the aligned human ESTs using the rat Nogo as a guiding template.

FIG. 14A-14C: Rat Nogo C nucleic acid (SEQ ID NO:31) sequence and its corresponding amino acid sequence (SEQ ID NO:32).

FIG. 15a-15e: Nogo A is present on the oligodendrocyte plasma membrane, as demonstrated by immunocytochemistry and cell surface biotinylation of oligodendrocytes in culture.

Immunocytochemistry (a-d): Oligodendrocytes from optic nerves of P10 rats were dissociated and cultured for 2 days. Staining of live cells with mAb IN-1 (a) or AS 472 (c) showed immunoreactivity on oligodendrocyte cell bodies and processes. In the presence of the competing peptide P472, AS 472 showed only background labeling (all cell types) (d). Similar non-specific staining was seen when primary antibodies were omitted (b). Evaluation: Number-coded dishes were randomly mixed and classified by 3 independent observers. 8/10 dishes were correctly classified AS 472-positive, mAb IN-1-positive or controls by all three observers.

Biotinylation (e): Rat P4 whole brain cultures enriched in oligodendrocytes were cell surface biotinylated with a membrane impermeable reagent after seven days in culture. Subsequently, cell homogenates were treated with streptavidin-Dynabeads. Precipitate (Ppt) and supernatant (sup) were blotted with AS472; they showed a distinct protein pattern: Cell surface Nogo A found in the precipitate showed a higher apparent molecular weight than intracellular Nogo A. This shift is probably due to glycosylation. The luminal ER protein BiP and the large majority of β-tubulin could only be found in the intracellular fraction.

FIG. 16a-16j: Functional assays show the presence of Nogo A on the cell membrane of oligodendrocytes. Pre-incubation of optic nerve cultures with AS 472 (a, b) allowed the NIH 3T3 fibroblasts to spread over the highly branched oligodendrocytes which are outlined by immunofluorescent staining for GalC (O1 antibody) (a). Arrows in the corresponding phase contrast image (b) indicate the NIH 3T3 fibroblasts spreading on top of the oligodendrocytes. (c, d): When AS 472 was added together with P472, the NIH 3T3 fibroblasts strictly avoided the territories of the GalC-positive oligodendrocytes (arrowheads) (Caroni and Schwab, 1988 Neuron 1:85-96). (e, f): In the presence of AS 472, P0 rat dissociated DRG neurons were able to extend neurites over the territory of highly branched oligodendrocytes (arrows in f). (g, h): The peptide P472 efficiently competed the neutralizing activity of AS 472: the neurites completely avoided the oligodendrocytes. AS 472 used in these experiments was generated against the rat 472 peptide sequence. (i, j): Quantification of these results (as described in methods) demonstrated the strong neutralizing activity of AS 472 in both types of assays. Scale bar: 40 μm.

FIG. 17a-17e: Recombinant Nogo A is an inhibitory substrate and its inhibitory activity is neutralized by mAb IN-1. RecNogo A enriched extracts from a stable CHO-Nogo A cell line, or β-galactosidase, isolated in parallel from the stable CHO-LacZ cell line, were coated for the NIH 3T3 fibroblast spreading and DRG neurite outgrowth assays. (a) Silver gel of myc-his-tagged recLacZ (lane 1) and recNogo A (lane 2) shows the Nogo A band at 180 kD. The identity of the Nogo A band was confirmed by Western blot incubated with AS Bruna (lane 3) and an anti-myc antibody 9E10 (lane 4). (b) RecNogo A coated dishes were clearly inhibitory to the NIH 3T3 spreading. Pre-incubation with mAb IN-1 or AS Bruna resulted in a highly significant (p<0.01) neutralization of inhibitory activity. The control 1 gM mAb O1 and pre-immune serum were ineffective. CHO-LacZ extract had a partial inhibitory effect on the NIH 3T3 cells, probably due to endogenous CHO proteins. This inhibitory activity was not influenced by pre-incubation with antibodies.

(c) For DRG neurite outgrowth assays, the same protein material as in (b) was mixed with laminin and coated. RecNogo A had a very potent inhibitory effect on neurite outgrowth of dissociated DRG in a dose-dependent manner. The activity was neutralized by mAb IN-1 (p<0.001), but not by control mAb O1. Protein material isolated from CHO-LacZ cells was not inhibitory at any of the concentrations used, nor did incubation with antibodies have any effect on neurite outgrowth. Examples for scoring are shown in (d): 1 μg recNogo A, no or short neurites (arrows) score: 2, and in (e): 1 μg CHO-LacZ, long, branched neurites (arrowheads) score: 5-6. Statistical analysis was performed with two-tailed Student's t test. Scale bar: 280 μm.

Figure 18:
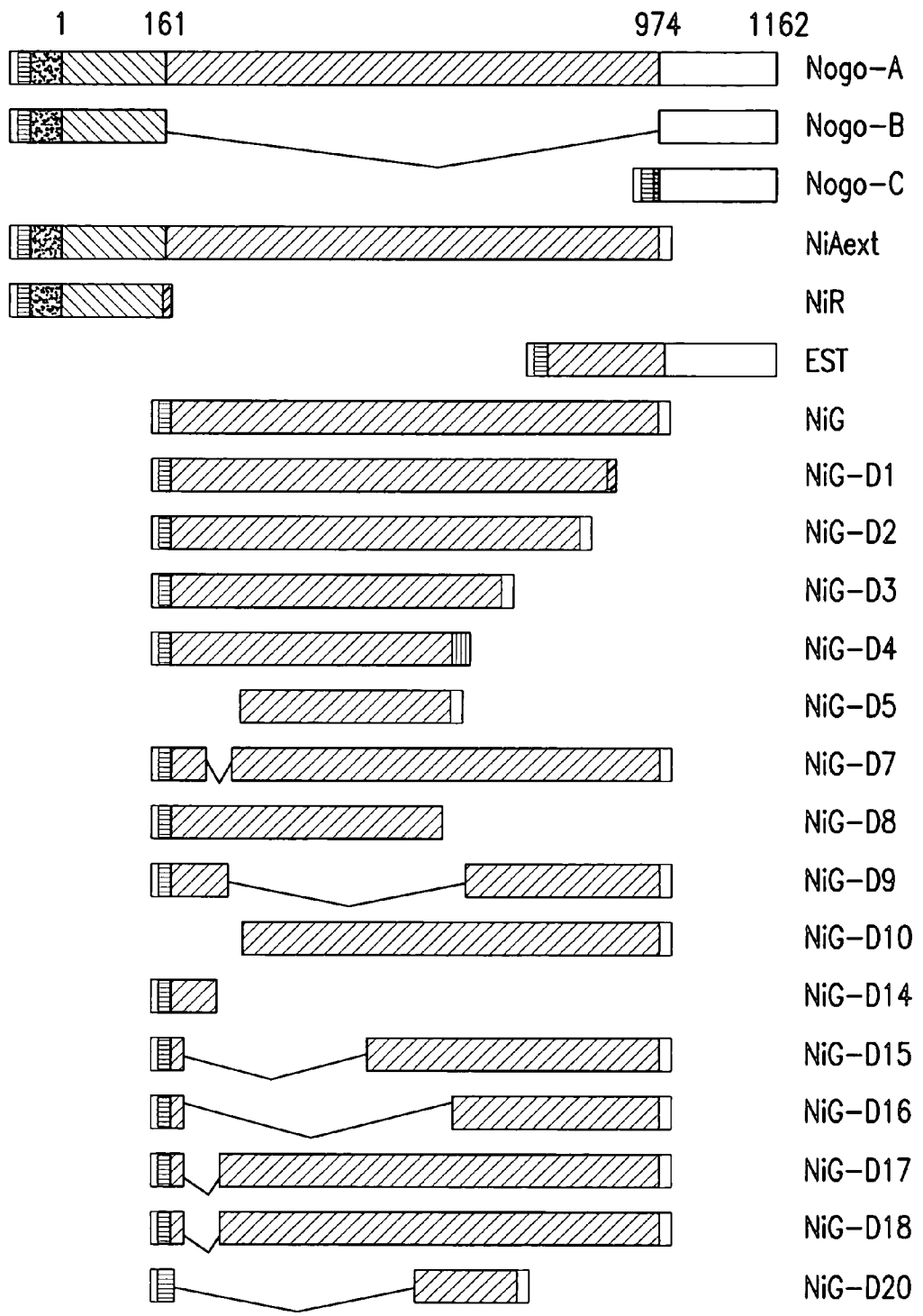

FIG. 18: Functional Analysis of Nogo Deletion Mutants. The following deletion constructs encoding fusion proteins containing fragments of Nogo or truncated portions of Nogo (as listed below) were generated as described in Section 6.2.7 hereinbelow.

Nogo-A: His-tag/T7-tag/vector/Nogo-A seq. aa1-1162.
Nogo-B: His-tag/T7-tag/vector/Nogo-A seq. aa1-171+975-1162
Nogo-C: His-tag/T7-tag/Nogo-C N-terminus (11 aa)+ Nogo-A seq. aa 975-1162
NiAext: His-tag/T7-tag/vector/Nogo-A seq. aa1-974/T7-tag
NiR: His-tag/T7-tag/vector/Nogo-A seq. aa1-171/vector
NiG: His-tag/T7-tag/Nogo-A seq. aa 172-974/His-tag
EST: His-tag/T7-tag/Nogo-A seq. aa 760-1162
NiG-D1: His-tag/T7-tag/Nogo-A seq. aa172-908/vector
NiG-D2: His-tag/T7-tag/Nogo-A seq. aa 172-866/His-tag
NiG-D3: His-tag/T7-tag/Nogo-A seq. aa 172-723/His-tag
NiG-D4: His-tag/T7-tag/Nogo-A seq. aa 172-646/vector
NiG-D5: His-tag/T7-tag/Nogo-A seq. aa 291-646/His-tag
NiG-D7: His-tag/T7-tag/Nogo-A seq. aa 172-234+292-974/His-tag
NiG-D8: His-tag/T7-tag/Nogo-A seq. aa 172-628
NiG-D9: His-tag/T7-tag/Nogo-A seq. aa 172-259+646-974/His-tag
NiG-D10: His-tag/T7-tag/Nogo-A seq. aa 291-974/His-tag
NiG-D14: His-tag/T7-tag/Nogo-A seq. aa 172-259
NiG-D15: His-tag/T7-tag/Nogo-A seq. aa 172-189+491-974/His-tag
NiG-D16: His-tag/T7-tag/Nogo-A seq. aa 172-189+619-974/His-tag
NiG-D17: His-tag/T7-tag/Nogo-A seq. aa 172-189+257-974/His-tag
NiG-D18: His-tag/T7-tag/Nogo-A seq. aa 172-189+261-974/His-tag
NiG-D20: His-tag/T7-tag/Nogo-A seq. aa 542-722/His-tag The amino acid (aa) numbers are based on rat Nogo A amino acid sequence numbering (SEQ ID NO: 2) starting with the first methionine. The His-tag and T7-tag consist of 34 amino acids. The N- and C-terminal vector sequences are derived from the expression vector pET28.

5. DETAILED DESCRIPTION OF THE INVENTION

The present invention relates to nucleotide sequences of Nogo genes, and amino acid sequences of their encoded proteins. The invention further relates to fragments and other derivatives, and analogs, of Nogo proteins. Nucleic acids encoding such fragments or derivatives are also within the scope of the invention. The invention provides Nogo genes and their encoded proteins of many different species. The Nogo genes of the invention include human, rat and bovine Nogo and related genes (homologs) in other species. The bovine subsequences disclosed in Spillman et al., 1998, J. Biol. Chem. 273:19283-19293, are not claimed as part of the present invention. In specific embodiments, the Nogo genes and proteins are from vertebrates, or more particularly, mammals. In a preferred embodiment of the invention, the Nogo genes and proteins are of human origin. Production of the foregoing proteins and derivatives, e.g., by recombinant methods, is provided.

The Nogo gene as provided by the present invention, encompasses nucleic acid molecules encoding three isoforms of Nogo; namely Nogo A, Nogo B and Nogo C. Reference to the gene "Nogo" shall include nucleic acid molecules encoding all three isoforms unless otherwise specified. Likewise, reference to Nogo protein shall include all three isoforms of Nogo unless otherwise specified. Nogo proteins of the invention can prevent regeneration of neurons in the spinal cord or brain (i.e. non-permissive substrate properties), inhibit dorsal root ganglia neurite outgrowth, induce dorsal root ganglia growth cone collapse, block NIH 3T3 cell spreading, block PC12 neurite outgrowth, etc.

The Nogo proteins, fragments and derivatives thereof are free of all central nervous system myelin material; in particular, they are free of all central nervous system myelin material with which the Nogo protein is naturally associated. Such material may include other CNS myelin proteins, lipids, and carbohydrates. The Nogo proteins, fragments and derivatives thereof of the invention are also preferably free of the reagents used in purification from biological specimens, such as detergents.

In a specific embodiment, the invention provides recombinant Nogo proteins, fragments and derivatives thereof as prepared by methods known in the art, such as expressing the Nogo gene in a genetically engineered cell.

The invention also relates to Nogo derivatives and analogs of the invention which are functionally active, i.e., they are capable of displaying one or more known functional activities associated with a full-length (wild-type) Nogo protein. Such functional activities include but are not limited to the ability to interact (or compete for binding) with neural growth regulatory proteins, antigenicity [ability to bind (or compete with Nogo for binding) to an anti-Nogo antibody], immunogenicity (ability to generate antibody which binds to Nogo), preventing regeneration of neurons in the spinal cord or brain, conferring to a substrate the property of restricing growth, spreading, and migration of neural cells, and neoplastic cells, inhibiting dorsal root ganglia neurite outgrowth, inducing dorsal root ganglia growth cone collapse, blocking NIH 3T3 cell spreading in vitro, blocking PC12 neurite outgrowth, restricting neural plasticity, etc.

The invention further relates to fragments (and derivatives and analogs thereof) of Nogo which comprise one or more domains of the Nogo protein.

Antibodies to Nogo, its derivatives and analogs, are additionally provided.

The present invention also relates to therapeutic and diagnostic methods and compositions based on Nogo proteins and nucleic acids and anti-Nogo antibodies. The invention provides for treatment of disorders of growth regulated cells or organs by administering compounds that promote Nogo activity (e.g., Nogo proteins and functionally active analogs and derivatives (including fragments) thereof; nucleic acids encoding the Nogo proteins, analogs, or derivatives, agonists of Nogo).

The invention also provides methods of treatment of damage or disorder of the nervous system by administering compounds that antagonize, or inhibit, Nogo function (e.g., antibodies, Nogo antisense nucleic acids, Nogo antagonist derivatives).

Animal models, diagnostic methods and screening methods for predisposition to disorders are also provided by the invention.

For clarity of disclosure, and not by way of limitation, the detailed description of the invention is divided into the subsections which follow.

5.1 Isolation of Nogo Genes

The invention relates to the nucleotide sequences of Nogo genes or nucleic acids. In one embodiment, Nogo nucleic acids comprise the rat cDNA sequence of FIG. 2a (SEQ ID NO:1) identified as Nogo A as depicted in FIG. 1b, or the coding regions thereof, or nucleotide sequences encoding a Nogo protein of 1163 amino acids in length or any functional fragment or derivative thereof (e.g., a protein having the sequence of SEQ ID NO:2, as shown in FIG. 2a).

In another embodiment, Nogo nucleic acids comprise the nucleotide sequence encoding Nogo B, whereas the Nogo B protein is equivalent to the amino terminal 172 amino acids fused to the carboxy terminal 188 amino acids of Nogo A, resulting in a truncated 360 amino acid protein. The transcripts for Nogo B arise as a result of alternative splicing which removes the intervening nucleotide coding sequence.

In yet another embodiment of the present invention, Nogo nucleic acids comprise the nucleotide sequences encoding Nogo C, whereas the Nogo C protein contains 11 amino acids at its amino terminus which are not present in Nogo A, and the carboxy terminal 188 amino acids of Nogo A and B. The Nogo C protein has 199 amino acids. The transcript encoding Nogo C is the result of transcription from an alternative Nogo promoter.

In yet another specific embodiment, the present invention provides bovine Nogo nucleic acid sequences (SEQ ID NO:28).

In yet another specific embodiment, the instant invention provides the nucleotide sequences encoding human Nogo, and fragments of human Nogo proteins, including the human equivalents to rat Nogo A, Nogo B and Nogo C. The human Nogo nucleic acid sequence is elucidated using the rat Nogo A transcript as a template and splicing together human expressed sequence tags (EST) to reveal a continuous nucleotide sequence. The rat and bovine amino acid sequences of Nogo also provided information on the proper translational reading frame such that an amino acid sequence of human Nogo is deduced. The instant invention also provides amino acid sequences of fragments of the human Nogo gene.

The invention also provides purified nucleic acids consisting of at least 8 nucleotides (i.e., a hybridizable portion) of a Nogo sequence; in other embodiments, the nucleic acids consist of at least 25 (continuous) nucleotides, 50 nucleotides, 100 nucleotides, 150 nucleotides, 20 nucleotides, 500 nucleotides, 700 nucleotides, or 800 nucleotides of a Nogo sequence, or a full-length Nogo coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of a Nogo gene.

In a specific embodiment, a nucleic acid which is hybridizable to a Nogo nucleic acid (e.g., having sequence SEQ ID NO:2; FIG. 2a), or to a nucleic acid encoding a Nogo derivative, under conditions of low stringency is provided. By way of example and not limitation, procedures using such conditions of low stringency are as follows (see also Shilo and Weinberg, 1981, Proc. Natl. Acad. Sci. USA 78:6789-6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20× $10^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations as demonstrated in the example in Section 6.1.1).

In another specific embodiment, a nucleic acid which is hybridizable to a Nogo nucleic acid under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid, which is hybridizable to a Nogo nucleic acid under conditions of moderate stringency is provided. For example, but not limited to, procedures using such conditions of moderate stringency are as follows: Filters containing DNA are pretreated for 6 h at 55° C. in a solution containing 6×SSC, 5× Denhart's solution, 0.5% SDS and 100 µg/ml denatured salmon sperm DNA. Hybridizations are carried out in the same solution and 5-20× 10$^6$ cpm $^{32}$P-labeled probe is used. Filters are incubated in hybridization mixture for 18-20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS. Such stringency conditions are suitable for isolating nucleic acid molecules comprising Nogo gene sequences in another species, e.g., using the rat or bovine Nogo cDNA clones as probe to isolate the human Nogo cDNA.

A number of human expressed sequence tags (ESTs) reported in published nucleic acid sequence databases display a high degree of sequence identity when compared to segments of the Nogo gene sequences of the invention. The following preliminary list of human ESTs were identified and are listed by their Genbank accession numbers: AA158636 (SEQ ID NO:35), AA333267 (SEQ ID NO:36), AA081783 (SEQ ID NO:37), AA167765 (SEQ ID NO:38), AA322918 (SEQ ID NO:39), AA092565 (SEQ ID NO:40), AA081525 (SEQ ID NO:41), and AA081840 (SEQ ID NO:42) using ENTREZ Nucleotide Query. Prior to the present invention, none of the above-identified ESTs had been characterized with respect to the amino acid sequences these ESTs may encode in vivo. Nothing was known about the function of the proteins comprising the predicted amino acid sequences of the human ESTs. Furthermore, an EST, such as AA158636, aligning with the 5' end of rat Nogo cDNA and another EST, such as AA081840, aligning with the 3' end of rat cDNA, are not overlapping and would not be perceived to be part of the same human cDNA sequence.

Based on the Nogo gene sequences of the present invention, it is believed that these human ESTs represent portions of the human Nogo gene that are expressed in the tissue from which the ESTs were obtained. Accordingly, the present invention encompasses nucleic acid molecules comprising two or more of the above-identified human ESTs. The ESTs may be expressed in the same human tissue, or in different human tissues. Preferably, the nucleic acid molecules of the invention comprise the nucleotide sequences of at least two human ESTs which are not overlapping with respect to each other, or which do not overlap a third or more human EST.

Since the above-identified human ESTs are now identified as fragments of the human Nogo gene due to the cloning of bovine and rat Nogo nucleic acids, it is contemplated that the human ESTs have similar functions relative to the other Nogo nucleic acid molecules in various methods of the invention, such as but not limited to, for example, the expression of human Nogo polypeptides, hybridization assays, and inhibition of Nogo expression as antisense nucleic acid molecules, etc.

Moreover, the present invention provides and includes the predicted amino acid sequence of the human Nogo protein, and fragments thereof. As shown in FIG. 13, the amino acid sequence of rat Nogo protein (FIG. 2a; SEQ ID NO:2) is aligned with the predicted amino acid sequence of human Nogo protein (FIG. 13; SEQ ID NO:29). Accordingly, the present invention encompasses human Nogo proteins comprising the predicted amino acid sequence of human Nogo, FIG. 13 and SEQ ID NO:29, or a subsequence of the predicted amino acid sequence of human Nogo, consisting of at least 6 amino acid residues, or one or more of the following predicted amino acid sequences of human Nogo fragments: MEDLDQSPLVSSS (Human Nogo, corresponding to amino acids 1-13 with SEQ ID NO:43), KIMDLKEQPGNTISAG (Human Nogo, corresponding to amino acids 187-203 with SEQ ID NO:44), KEDEVVSSEKAKDSFNEKR (Human Nogo, corresponding to amino acids 340-358 with SEQ ID NO:45), QESLYPAAQLCPSFEESEATPSPVLPDIVMEAPLNSAVPSAGASVIQPSS (Human Nogo, corresponding to amino acids 570-619 with SEQ ID NO:46). Naturally occurring human Nogo and recombinant human Nogo, and fragments thereof having an amino acid sequence substantially similar to the above-described amino acid sequences and able to be bound by an antibody directed against a Nogo protein are within the scope of the invention.

The present invention further provides nucleic acid molecules that encodes a human Nogo protein having an amino acid sequence substantially similar to the amino acid sequence as shown in FIG. 13 (FIG. 13; SEQ ID NO:29). In specific embodiments, nucleic acid molecules encoding fragments of human Nogo protein having an amino acid sequence substantially similar to the amino acid sequence as shown in FIG. 13 (SEQ ID NO:29) are also contemplated with the proviso that such nucleic acid molecules do not comprise the nucleotide sequence of the above-identified human ESTs.

An amino acid sequence is deemed to be substantially similar to the predicted amino acid sequence of human Nogo protein when more than 50%, 55%, 60%, 65%, 70%, 75%, 80%, 85%, 90%, 95%, or 97% of the amino acid residues in the two molecules are identical when a computer algorithm is used in which the alignment is done by a computer homology program known in the art, for example a BLAST computer searching (Altschul et al., 1994, Nature Genet. 6:119-129) is used.

By way of example and not limitation, useful computer homology programs include the following: Basic Local Alignment Search Tool (BLAST) (home page of the National Center for Biotechnology Information) (Altschul et al., 1990, J. of Molec. Biol., 215:403-410, "The BLAST Algorithm; Altschul et al., 1997, Nuc. Acids Res. 25:3389-3402) a heuristic search algorithm tailored to searching for sequence similarity which ascribes significance using the statistical methods of Karlin and Altschul 1990, Proc. Nat'l Acad. Sci. USA, 87:2264-68; 1993, Proc. Nat'l Acad. Sci. USA 90:5873-77. Five specific BLAST programs perform the following tasks:

1) The BLASTP program compares an amino acid query sequence against a protein sequence database.

2) The BLASTN program compares a nucleotide query sequence against a nucleotide sequence database.

3) The BLASTX program compares the six-frame conceptual translation products of a nucleotide query sequence (both strands) against a protein sequence database.

4) The TBLASTN program compares a protein query sequence against a nucleotide sequence database translated in all six reading frames (both strands).

5) The TBLASTX program compares the six-frame translations of a nucleotide query sequence against the six-frame translations of a nucleotide sequence database.

As will be understood by those skilled in the art, the TBLASTN program is particularly useful to identify nucleic acids with a desired percent identity and the BLASTP program is particularly useful to identify amino acid sequences with a desired percent identity.

Smith-Waterman (database: European Bioinformatics Institute (Smith-Waterman, 1981, J. of Molec. Biol., 147: 195-197) is a mathematically rigorous algorithm for sequence alignments.

FASTA (see Pearson et al., 1988, Proc. Nat'l Acad. Sci. USA, 85:2444-2448) is a heuristic approximation to the Smith-Waterman algorithm. For a general discussion of the procedure and benefits of the BLAST, Smith-Waterman and FASTA algorithms, see Nicholas et al., 1998, "A Tutorial on Searching Sequence Databases and Sequence Scoring Methods" (home page of the Pittsburgh Supercomputing Center) and references cited therein.

The uses of the predicted amino acid sequences of human Nogo, or the nucleotide sequences of human ESTs, including degenerate sequences encoding the predicted amino acid sequence of human Nogo, for isolating or identifying the human Nogo gene, fragments, naturally occurring mutants and variants thereof, is within the scope of the invention. Such uses which will be known to one of skill in the art include but are not limited to using the information to prepare nucleic acid probes for DNA library screening, DNA amplification, genetic screening of the human population, and to prepare synthetic peptides for making antibodies. Detailed description of some of such uses are provided herein in later sections.

Nucleic acids encoding derivatives and analogs of Nogo proteins, and Nogo antisense nucleic acids are additionally provided. As is readily apparent, as used herein, a "nucleic acid encoding a fragment or portion of a Nogo protein" shall be construed as referring to a nucleic acid encoding only the recited fragment or portion of the Nogo protein and not the other contiguous portions of the Nogo protein as a continuous sequence. In this context, a portion means one or more amino acids.

Fragments of Nogo nucleic acids comprising regions conserved between (with homology to) other Nogo nucleic acids, of the same or different species, are also provided. Nucleic acids encoding one or more Nogo domains are provided in FIG. 2a, for example, the conserved carboxy terminal domain of rat Nogo, which has about 180 amino acids, and is encoded by the last 540 nucleotides of the coding sequence prior to the stop codon. The nucleotide and amino acid sequences of two hydrophobic domains within the conserved carboxy terminus domain, i.e., from amino acids 988 to 1023, and from amino acids 1090 to 1125, in rat Nogo A, are also provided. The nucleotide and amino acid sequences of the amino terminal acidic domain of rat Nogo A, from residues 31 to 58, are also provided.

To perform functional analysis of various regions of Nogo, a series of deletions in the Nogo gene has been generated and cloned into an expression vector by recombinant DNA techniques and expressed as a fusion protein. Nucleic acids that encode a fragment of a Nogo protein are provided, e.g., nucleic acids that encode amino acid residues 1-171, 172-974, 259-542, 542-722, 172-259, 722-974, or 975-1162 of SEQ ID NO: 2, or combinations thereof; and nucleic acids that encode amino acid residues 1-131, 132-939, 206-501, 501-680, 132-206, 680-939, and 940-1127 of SEQ ID NO:29, or combinations thereof. Some of the deletion constructs comprises truncated portions of Nogo and additional nucleotide sequences encoding a hexahistidine tag and/or a T7-tag. Nucleic acids encoding truncated Nogo proteins that lacks amino acid residues 172-259, amino acid residues 974-1162, or amino acid residues 172-259 and 974-1162, of SEQ ID NO:2 but otherwise comprises the remainder of SEQ ID NO: 2; or amino acid residues 132-206, amino acid residues 939-1127, or amino acid residues 132-206 and 939-1127, of SEQ ID NO:29 but otherwise comprises the remainder of SEQ ID NO:29, are provided. The structure of exemplary deletion constructs are shown in FIG. 18. The deletion constructs produce fragments or truncated portion(s) of Nogo when introduced into a cell. The biological activities of these mutants were tested in various functional assays as described in Table 2 in Section 6.2.7.

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed Nogo product. In one embodiment, anti-Nogo antibodies can be used for selection.

In another embodiment, polymerase chain reaction (PCR) is used to amplify the desired sequence in a genomic or cDNA library, prior to selection. Oligonucleotide primers representing known Nogo sequences can be used as primers in PCR. In a preferred aspect, the oligonucleotide primers represent at least part of the Nogo conserved segments of strong homology between Nogo of different species. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known Nogo nucleotide sequence and the nucleic acid homolog being isolated. For cross species hybridization, low stringency conditions are preferred. For same species hybridization, moderately stringent conditions are preferred.

After successful amplification of a segment of a Nogo homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Nogo proteins and Nogo analogs may be identified.

The above-methods are not meant to limit the following general description of methods by which clones of Nogo may be obtained.

Any eukaryotic cell potentially can serve as the nucleic acid source for the molecular cloning of the Nogo gene. The nucleic acid sequences encoding Nogo can be isolated from vertebrate, mammalian, human, porcine, murine, bovine, feline, avian, equine, canine, as well as additional primate sources, insects, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Nogo (of any species) gene or its specific RNA, or a fragment thereof (see Section 6.1.1), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, post-translational modifications, acidic or basic properties or antigenic properties as known for Nogo. Antibodies to Nogo are available, such as IN-1 and IN-2 (U.S. Pat. No. 5,684,133), AS Bruna and AS 472. Preparation of AS Bruna and AS 472 are described in Section 6.1.7. The Nogo protein may be identified by binding of labeled antibody to the putatively Nogo synthesizing clones, in an ELISA (enzyme-linked immunosorbent assay)-type procedure or by western blotting of purified or whole cell extracts.

The Nogo gene can also be identified by mRNA selection by nucleic acid hybridization followed by in vitro translation. In this procedure, fragments are used to isolate complementary mRNAs by hybridization. Such DNA fragments may represent available, purified Nogo DNA of another species (e.g., mouse, human). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Nogo protein. A radiolabeled Nogo cDNA can be synthesized using the selected mRNA (from the adsorbed polysomes) as a template. The radiolabeled mRNA or cDNA may then be used as a probe to identify the Nogo DNA fragments from among other genomic DNA fragments.

Alternatives to isolating the Nogo genomic DNA include, but are not limited to, chemically synthesizing the gene sequence itself from a known sequence or making cDNA to the mRNA which encodes the Nogo protein. For example, RNA for cDNA cloning of the Nogo gene can be isolated from cells which express Nogo. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). In a specific example, Nogo is cloned into pcDNA3 with epitope tags for simplified protein expression analysis (Section 6.1.10).

The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Nogo gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Nogo gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Nogo sequences provided by the instant invention include those nucleotide sequences encoding substantially the same amino acid sequences as found in native Nogo proteins, and those encoded amino acid sequences with functionally equivalent amino acids, as well as those encoding other Nogo derivatives or analogs, as described in Sections 6.2.1 and 6.2.2 infra for Nogo derivatives and analogs.

5.2 Expression of the Nogo Genes

The nucleotide sequence coding for a Nogo protein or a functionally active analog or fragment or other derivative thereof (see FIGS. 1b and 2a; Sections 6.2.1 and 6.2.2), can be inserted into an appropriate expression vector, i.e., a vector which contains the necessary elements for the transcription and translation of the inserted protein-coding sequence. The necessary transcriptional and translational signals can also be supplied by the native Nogo gene and/or its flanking regions. The coding sequence can also be tagged with a sequence that codes for a well described antigen or biological molecule that has known binding properties to a binding partner (e.g. myc epitope tag, histidine tag, T7 epitope tag etc., see Section 6.2.6 and FIG. 11a-11c). This additional sequence can then be exploited to purify the Nogo protein, protein fragment, or derivative using the interaction of the binding group with its corresponding partner, which is attached to a solid matrix.

A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the human Nogo gene is expressed, or a sequence encoding a functionally active portion of human Nogo, as a specific example, either Nogo A, Nogo B or Nogo C is expressed (FIG. 1b). In yet another embodiment, a fragment of Nogo comprising a domain of the Nogo protein is expressed.

As used herein, a cell is "transformed" with a nucleic acid, when such cell contains a nucleic acid not natively present in the cell, after introduction of the nucleic acid into the cell or its ancestor, e.g., by transfection, electroporation, transduction, etc.

Nucleotide sequences encoding fragments of human Nogo A comprising an amino acid sequence selected from the group consisting of amino acid residues 1-131, 132-939, 206-501, 501-680, 132-206, 680-939, and 940-1127 of SEQ ID NO:29 are also provided. Nucleotide sequences that encodes truncated portions of human Nogo A are also provided; the truncated proteins lack amino acid residues 132-206, amino acid residues 939-1127, or amino acid residues 132-206 and 939-1127, of SEQ ID NO:29 but otherwise comprises the remainder of SEQ ID NO:29.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Nogo protein or peptide fragment may be regulated by a second nucleic acid sequence so that the Nogo protein or peptide is expressed in a host transformed with the recombinant DNA molecule. For example, expression of a Nogo protein may be controlled by any promoter/enhancer element known in the art. An exemplary embodiment is to use one of Nogo's natural promoters, either P1 or P2, discussed in Section 6.2.1. A non-native promoter may also be used. Promoters which may be used to control Nogo expression include, but are not limited to, the SV40 early promoter region (Bernoist and Chambon, 1981, Nature 290: 304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a Nogo-encoding nucleic acid, one or more origins of replication, and, optionally, one or more selectable markers (e.g., an antibiotic resistance gene).

In a specific embodiment, an expression construct is made by subcloning a Nogo coding sequence into the EcoRI restriction site of each of the three pGEX vectors (Glutathione S-Transferase expression vectors; Smith and Johnson, 1988, Gene 7:31-40). This allows for the expression of the Nogo protein product from the subclone in the correct reading frame.

Expression vectors containing Nogo gene inserts can be identified by three general approaches: (a) nucleic acid hybridization, (b) presence or absence of "marker" gene functions, and (c) expression of inserted sequences. In the first approach, the presence of a Nogo gene inserted in an expression vector can be detected by nucleic acid hybridization using probes comprising sequences that are homologous to an inserted Nogo gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a Nogo gene in the vector. For example, if the Nogo gene is inserted within the marker gene sequence of the vector, recombinants containing the Nogo insert can be identified by the absence of the marker gene function. In the third approach, recombinant expression vectors can be identified by assaying the Nogo product expressed by the recombinant. Such assays can be based, for example, on the physical or functional properties of the Nogo protein in in vitro assay systems, e.g., binding with anti-Nogo antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Nogo protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the Nogo protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3 Identification and Purification of the Nogo Gene Products

In particular aspects, the invention provides amino acid sequences of Nogo, preferably human Nogo, and fragments and derivatives thereof which comprise an antigenic determinant (i.e., can be recognized by an antibody) or which are otherwise functionally active, as well as nucleic acid sequences encoding the foregoing. "Functionally active" Nogo material as used herein refers to that material displaying one or more known functional activities associated with a full-length (wild-type) Nogo A protein, e.g., non-permissive substrate properties, dorsal root ganglia growth cone collapse, NIH 3T3 spreading inhibition, neurite outgrowth inhibition, binding to a Nogo substrate or Nogo binding partner, antigenicity (binding to an anti-Nogo antibody), immunogenicity, etc.

In specific embodiments, the invention provides fragments of a Nogo protein consisting of at least 6 amino acids, 10 amino acids, 17 amino acids, 50 amino acids, 100 amino acids or of at least 220 amino acids. In other embodiments, the proteins comprise or consist essentially of the highly conserved Nogo carboxy terminal domain (carboxy terminal 188 amino acids of Nogo A). Fragments, or proteins comprising fragments, lacking the conserved carboxy terminal domain, or the hydrophobic carboxy terminal stretches, or the amino terminal acidic domain, or the amino terminal poly-proline region or any combination thereof, of a Nogo protein are also provided. Nucleic acids encoding the foregoing are provided.

Once a recombinant which expresses the Nogo gene sequence is identified, the gene product can be analyzed. This is achieved by assays based on the physical or functional properties of the product, including radioactive labeling of the product followed by analysis by gel electrophoresis, immunoassay, etc.

Once the Nogo protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay including dorsal root ganglia growth cone collapse, NIH 3T3 spreading inhibition, inhibition of neurite regeneration in optic nerves (see Sections 6.2.4-6.2.5).

Alternatively, once a Nogo protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105-111).

In another alternate embodiment, native Nogo C, can be purified from natural sources, by standard methods such as those described above (e.g. immunoaffinity purification).

In a specific embodiment of the present invention, such Nogo proteins, whether produced by recombinant DNA techniques or by chemical synthetic methods or by purification of native proteins, include but are not limited to those containing, as a primary amino acid sequence, all or part of the amino acid sequence substantially as depicted in FIG. 2a (SEQ ID NO:2), bovine in FIG. 12 (SEQ ID NO:28), or human in FIG. 13 (SEQ ID NO:29), as well as fragments and other derivatives (such as but not limited to those depicted in FIG. 18), and analogs thereof, including proteins homologous thereto. Preferably, the Nogo proteins of the invention are free of all CNS myelin material with which it is normally associated.

5.4 Structure of the Nogo Gene and Protein

The structure of the Nogo gene and protein can be analyzed by various methods known in the art and several of these methods are described in the following subsections.

5.4.1 Genetic Analysis

The cloned DNA or cDNA corresponding to the Nogo gene can be analyzed by methods including but not limited to Southern hybridization (Southern, E. M., 1975, J. Mol. Biol. 98:503-517), Northern hybridization (see e.g., Freeman et al., 1983, Proc. Natl. Acad. Sci. U.S.A. 80:4094-4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652-7656; Ochman et al., 1988, Genetics 120:621-623; Loh et al., 1989, Science 243:217-220) followed by Southern hybridization with a Nogo-specific probe can allow the detection of the Nogo gene in DNA from various cell types. Methods of amplification other than PCR are commonly known and can also be employed. In one embodiment, Southern hybridization can be used to determine the genetic linkage of Nogo. Northern hybridization analysis can be used to determine the expression of the Nogo gene. Various cell types, at various states of development or activity can be tested for Nogo expression. The stringency of the hybridization conditions for both Southern and Northern hybridization can be manipulated to ensure detection of nucleic acids with the desired degree of relatedness to the specific Nogo probe used. Modifications of these methods and other methods commonly known in the art can be used.

Restriction endonuclease mapping can be used to roughly determine the genetic structure of the Nogo gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499-560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2 Protein Analysis

The amino acid sequence of the Nogo protein can be derived by deduction from the DNA sequence, or alternatively, by direct sequencing of the protein, e.g., with an automated amino acid sequencer.

The Nogo protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Nogo protein and the corresponding regions of the gene sequence which encode such regions.

Secondary, structural analysis (Chou, P. and Fasman, G., 1974, Biochemistry 13:222) can also be done, to identify regions of Nogo that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, A., 1974, Biochem. Exp. Biol. 11:7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5 Generation of Antibodies to Nogo Proteins and Derivatives Thereof

According to the invention, the Nogo protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. Antibodies directed to a recombinant fragment of rat and bovine Nogo are produced (Section 6.1.7), these antibodies also cross react with other species epitopes. In another embodiment, fragments of a Nogo protein identified as hydrophilic are used as immunogens for antibody production.

Various procedures known in the art may be used for the production of polyclonal antibodies to a Nogo protein or derivative or analog. In a particular embodiment, rabbit polyclonal antibodies to an epitope of a Nogo protein encoded by a sequence of SEQ ID NO:2 in FIG. 2a, SEQ ID NO:28 in FIG. 12, SEQ ID NO:32 in FIG. 14, or SEQ ID NO:29 in FIG. 13, (rat Nogo A, bovine Nogo, rat Nogo C, or human Nogo respectively) or a subsequence thereof, can be obtained. For the production of antibody, various host animals can be immunized by injection with the native Nogo protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Nogo protein sequence or analog thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030). or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for Nogo together with genes from a human antibody molecule of appropriate biological activity can be used; such antibodies are within the scope of this invention.

According to the invention, techniques described for the production of single chain antibodies (U.S. Pat. No. 4,946,778) can be adapted to produce Nogo-specific single chain antibodies. Techniques described for the construction of Fab expression libraries can also be utilized (Huse et al., 1989, Science 246:1275-1281) to allow rapid and easy identification of monoclonal Fab fragments with the desired specificity for Nogo proteins, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a Nogo protein, one may assay generated hybridomas for a product which binds to a Nogo fragment containing such domain. For selection of an antibody that specifically binds a first Nogo homolog but which does not specifically bind a different Nogo homolog, one can select on the basis of positive binding to the first Nogo homolog and a lack of binding to the second Nogo homolog.

Antibodies specific to a domain of a Nogo protein are also provided.

The foregoing antibodies can be used in methods known in the art relating to the localization and activity of the Nogo protein sequences of the invention, e.g., for imaging these proteins, measuring levels thereof in appropriate physiological samples, in diagnostic methods, etc.

Anti-Nogo antibodies and fragments thereof containing the binding domain are Therapeutics.

5.6 Nogo Proteins, Derivatives and Analogs

The invention further relates to Nogo proteins, and derivatives (including but not limited to fragments) and analogs of Nogo proteins. Nucleic acids encoding Nogo protein derivatives and protein analogs are also provided. In one embodiment, the Nogo proteins are encoded by the Nogo nucleic acids described in Section 5.1 supra. In particular aspects, Nogo A, Nogo B, or Nogo C proteins and derivatives, or analogs are of animals, e.g., mouse, rat, pig, cow, dog, monkey, human, fly, or frogs are within the scope of the invention.

The production and use of derivatives and analogs related to Nogo are also within the scope of the present invention. In a specific embodiment, the derivative or analog is functionally active, i.e., capable of exhibiting one or more functional activities associated with a full-length, wild-type Nogo protein. As one example, such derivatives or analogs which have the desired immunogenicity or antigenicity can be used, for example, in immunoassays, for immunization, for inhibition of Nogo activity, etc. Derivatives or analogs that retain, or alternatively lack or inhibit, a desired Nogo property of interest (e.g., binding to a Nogo binding partner, can be used as inducers, or inhibitors, respectively, of such property and its physiological correlates. A specific embodiment relates to a Nogo fragment that can be bound by an anti-Nogo antibody. Derivatives or analogs of Nogo can be tested for the desired activity by procedures known in the art, including but not limited to the assays described in Sections 6.1.10 to 6.1.12.

In order to map the active region(s) of Nogo, a series of Nogo deletion mutants have been prepared by recombinant DNA techniques as described in Section 6.2.7. The portions of Nogo which are present in the deletion mutants are shown in FIG. 18. In a specific embodiment, the invention provides fragments of Nogo e.g., fragments comprising (or alternatively consisting of) Nogo A (SEQ ID NO: 2) amino acid numbers 1-171, 172-974, 259-542, 542-722, 722-974, 172-259, or 975-1162, or combinations of the foregoing. Truncated mutants of Nogo lacking amino acid numbers 172-259 and/or 975-1162 of SEQ ID NO:2 are also provided, as these regions appear to be non-essential and can be removed from Nogo without affecting biological activity. The corresponding fragments of human Nogo A comprising (or alternatively consisting of) amino acid numbers 1-131, 132-939, 206-501, 501-680, 132-206, 680-939, or 940-1127 of SEQ ID NO:29 are also provided. Truncated mutants of human Nogo A are also provided which lack amino acid numbers 132-206, amino acid residues 939-1127, or amino acid residues 132-206 and 939-1127, of SEQ ID NO:29.

In a specific embodiment, the fragments are free of all CNS myelin material and/or display inhibitory activity of Nogo. Fusion proteins comprising one or more of the above fragments fused to a non-Nogo sequence are also provided.

Nogo gene derivatives can be made by altering Nogo sequences by substitutions, additions or deletions that provide for functionally equivalent molecules. Due to the degeneracy of nucleotide coding sequences, other DNA sequences which encode substantially the same amino acid sequence as a Nogo gene may be used in the practice of the present invention. These include but are not limited to nucleotide sequences comprising all or portions of Nogo genes which are altered by the substitution of different codons that encode a functionally equivalent amino acid residue within the sequence, thus producing a silent change. Likewise, the Nogo derivatives of the invention include, but are not limited to, those containing, as a primary amino acid sequence, all or part of the amino acid sequence of a Nogo protein including altered sequences in which functionally equivalent amino acid residues are substituted for residues within the sequence resulting in a silent change. For example, one or more amino acid residues within the sequence can be conservatively substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a Nogo protein consisting of at least 10 (continuous) amino acids of the Nogo protein is provided. In other embodiments, the fragment consists of at least 17 or 50 amino acids of the Nogo protein. In specific embodiments, such fragments are not larger than 35, 100 or 200 amino acids. Derivatives or analogs of Nogo include but are not limited to those molecules comprising regions that are substantially homologous to Nogo or fragments thereof (e.g., in various embodiments, at least 60% or 70% or 80% or 90% or 95% identity over an amino acid sequence of identical size or when compared to an aligned sequence in which the alignment is done by a computer homology program known in the art, for example BLAST computer searching (Altschul et al., 1994, Nature Genet. 6:119-129)) or whose encoding nucleic acid is capable of hybridizing to a coding Nogo sequence, under stringent, moderately stringent, or nonstringent conditions.

Molecules comprising Nogo fragments are also provided, e.g., containing hydrocarbon linkages to other moieties including labels or bioactive moieties.

The Nogo derivatives and analogs of the invention can be produced by various methods known in the art. The manipulations which result in their production can occur at the gene or protein level. For example, the cloned Nogo gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Nogo, care should be taken to ensure that the modified gene remains within the same translational reading frame as Nogo, uninterrupted by translational stop signals, in the gene region where the desired Nogo activity is encoded.

Additionally, the Nogo-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the Nogo sequence may also be made at the protein level. Included within the scope of the invention are Nogo protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Nogo can be chemically synthesized. For example, a peptide corresponding to a portion of a Nogo protein which comprises the desired domain or which mediates the desired activity in vitro, can be synthesized by use of a peptide synthesizer. Furthermore, if desired, nonclassical amino acids or chemical amino acid analogs can be introduced as a substitution or addition into the Nogo sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the Nogo derivative is a chimeric, or fusion, protein comprising a Nogo protein or fragment thereof (preferably consisting of at least a domain or motif of the Nogo protein, or at least 10 amino acids of the Nogo protein) joined at its amino- or carboxy-terminus via a peptide bond to an amino acid sequence of a different protein. In one embodiment, such a chimeric protein is produced by recombinant expression of a nucleic acid encoding the protein (comprising a Nogo-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of Nogo fused to any heterologous protein-encoding sequences may be constructed. Such heterologous protein-encoding sequences include, for example, the hexahistidine tag, and the T7 tag. A specific embodiment relates to a chimeric protein comprising a fragment of Nogo of at least six amino acids.

In another specific embodiment, the Nogo derivative is a molecule comprising a region of homology with a Nogo protein.

In a preferred embodiment, the Nogo derivatives (e.g., fragments) are proteins that are non-naturally occurring.

Other specific embodiments of derivatives and analogs are described in the subsection below and examples sections infra.

5.6.1 Derivatives of Nogo Containing One or More Domains of the Protein

In a specific embodiment, the invention relates to Nogo derivatives and analogs, in particular Nogo fragments and derivatives of such fragments, that comprise, or alternatively consist of, one or more domains of a Nogo protein, including but not limited to the conserved carboxy terminal and hydrophobic domains or the amino terminal acidic or poly proline rich domains, functional (e.g., binding) fragments of any of the foregoing, or any combination of the foregoing.

A specific embodiment relates to molecules comprising specific fragments of Nogo that are those fragments in the respective Nogo protein most homologous to specific fragments of a rat or bovine Nogo protein. A fragment comprising a domain of a Nogo homolog can be identified by protein analysis methods as described in Sections 6.1.2, 6.1.8, 6.1.9, 6.1.10, 6.1.11, or 6.1.12.

In another specific embodiment, a molecule is provided that comprises one or more domains (or functional portion thereof) of a Nogo protein but that also lacks one or more domains (or functional portion thereof) of a Nogo protein. In another embodiment, a molecule is provided that comprises one or more domains (or functional portion thereof) of a Nogo protein, and that has one or more mutant (e.g., due to deletion or point mutation(s)) domains of a Nogo protein (e.g., such that the mutant domain has decreased function).

5.7 Assays of Nogo Proteins, Derivatives and Analogs

The functional activity of Nogo proteins, derivatives and analogs can be assayed by various methods. The description of functional assays in the following sections are not meant to be limiting, and may include other assays known to one skilled in the art.

5.7.1 Assays of Nogo In Vitro Neurite Growth Inhibition

In a specific embodiment, Nogo proteins, derivatives and analogs can be assayed for inhibition of NIH 3T3 spreading or inhibition of PC12 neurite outgrowth using in vitro tissue culture (Section 6.1.10).

In an alternative embodiment, Nogo proteins, derivatives and analogs can be used to assay for explanted chick dorsal root ganglia growth cone collapse induced by the presence of Nogo. Similarly, Nogo function can be assayed for inhibition of neurite outgrowth of explanted chick dorsal root ganglia (Spillman et al., 1998 J. Biol. Chem. 273:19283-19293).

5.7.2 Assays of Nogo In Vivo Functional Properties

In one example, antagonists of Nogo proteins, derivatives and analogs can be used for in vivo assays of function using an animal model for corticospinal tract (CST) regeneration over long distances and behavior recovery.

In a preferred embodiment, a rodent corticospinal tract is damaged by surgical resection or spinal cord contusion, and antagonists of Nogo are administered to the animal. Neural plasticity, regeneration and functional recovery, as compared to untreated control animals or control antibody treated animals, are monitored for structural plasticity or regeneration by anatomical techniques, mainly by labeling of defined neural tracts. Functional recovery is measured by locomotion and by electrophysiology skill tests executed by the rodent (e.g. sticky paper test, food pellet reaching task, etc.) (Thallmair et al., 1998 Nat. Neuroscience 1(2):124-131).

5.7.3 Nogo Ligand Binding Inhibition and Assays Thereof

In one embodiment, where one is assaying for the ability to bind or compete with wild-type Nogo for binding to anti-Nogo antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a Nogo-binding protein is identified, the binding can be assayed, e.g., by means well-known in the art. In another embodiment, physiological correlates of Nogo binding to its substrates can be assayed.

Other methods will be known to the skilled artisan and are within the scope of the invention.

5.8 Therapeutic Uses

The invention provides for treatment or prevention of various diseases and disorders by administration of a therapeutic compound (termed herein "Therapeutic"). Such "Therapeutics" include but are not limited to: Nogo proteins and analogs and derivatives (including fragments) thereof (e.g., as described hereinabove); antibodies thereto (as described hereinabove); nucleic acids encoding the Nogo proteins, analogs, or derivatives (e.g., as described hereinabove); Nogo antisense nucleic acids, and Nogo agonists and antagonists. Disorders involving deregulated cellular growth, e.g. CNS tumors, are treated or prevented by administration of a Therapeutic that promotes Nogo function. Disorders in which neurite growth, regeneration, or maintenance are deficient or desired are treated by administration of a Therapeutic that antagonizes (inhibits) Nogo function. The above is described in detail in the subsections below.

Generally, administration of products of a species origin or species reactivity (in the case of antibodies) that is the same species as that of the patient is preferred. Thus, in a preferred embodiment, a human Nogo protein, derivative, or analog, or nucleic acid, or an antibody to a human Nogo protein, is therapeutically or prophylactically administered to a human patient.

5.8.1 Treatment and Prevention of Disorders Involving Deregulated Cellular Growth Diseases and disorders involving deregulated cellular growth are treated or prevented by administration of a Therapeutic that promotes (i.e., increases or supplies) Nogo function. Examples of such a Therapeutic include but are not limited to Nogo proteins, derivatives, or fragments that are functionally active, particularly that are active in inhibition of neurite extension or cellular growth inhibition (e.g., as demonstrated in in vitro assays or in animal models), and nucleic acids encoding a Nogo protein or functionally active derivative or fragment thereof (e.g., for use in gene therapy). Preferably, the Nogo proteins, derivatives or fragments thereof are free of all CNS myelin material with which it is naturally associated. Other Therapeutics that can be used, e.g., Nogo agonists, can be identified using in vitro assays or animal models, examples of which are described infra.

In specific embodiments, Therapeutics that promote Nogo function are administered therapeutically (including prophylactically): (1) in diseases or disorders involving an absence or decreased (relative to normal or desired) level of Nogo protein or function, for example, in patients where Nogo protein is lacking, genetically defective, biologically inactive or underactive, or underexpressed; or (2) in diseases or disorders wherein in vitro (or in vivo) assays (see infra) indicate the utility of Nogo agonist administration. The absence or decreased level in Nogo protein or function can be readily detected, e.g., by obtaining a patient tissue sample (e.g., from biopsy tissue) and assaying it in vitro for RNA or protein levels, structure and/or activity of the expressed Nogo RNA or protein. Many methods standard in the art can be thus employed, including but not limited to kinase assays, immunoassays to detect and/or visualize Nogo protein (e.g., Western blot, immunoprecipitation followed by sodium dodecyl sulfate polyacrylamide gel electrophoresis, immunocytochemistry, etc.) and/or hybridization assays to detect Nogo expression by detecting and/or visualizing Nogo mRNA (e.g., Northern assays, dot blots, in situ hybridization, etc.), etc.

Diseases and disorders involving deregulated cellular growth that can be treated or prevented include but are not limited to proliferative disorders, malignant tumors, nervous system tumors, etc. Examples of these are detailed below.

5.8.1.1 Neoplastic Growth

Neoplastic growth and related disorders that can be treated or prevented by administration of a Therapeutic that promotes Nogo function include but are not limited to those listed in Table 1 (for a review of such disorders, see Fishman et al., 1985, *Medicine*, 2d Ed., J.B. Lippincott Co., Philadelphia):

TABLE 1

| NEOPLASTIC GROWTH AND RELATED DISORDERS |
|---|
| Solid tumors |
| sarcomas and carcinomas |
| glioma, glioblastoma |
| astrocytoma |
| medulloblastoma |
| craniopharyngioma |
| ependymoma |

TABLE 1-continued

NEOPLASTIC GROWTH AND RELATED DISORDERS pinealoma
hemangioblastoma
acoustic neuroma
oligodendroglioma
menangioma
neuroblastoma
retinoblastoma In specific embodiments, malignancy or dysproliferative changes (such as metaplasias and dysplasias), or hyperproliferative disorders, are treated or prevented in the central nervous system, spinal cord or any neural tissues.

5.8.1.2 Premalignant Conditions

The Therapeutics of the invention that promote Nogo activity can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79.) Hyperplasia is a form of controlled cell proliferation involving an increase in cell number in a tissue or organ, without significant alteration in structure or function. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic that promotes Nogo function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In other embodiments, a patient which exhibits one or more of the following predisposing factors for malignancy is treated by administration of an effective amount of a Therapeutic: neurofibromatosis of Von Recklinghausen or retinoblastoma; see Robbins and Angell, 1976, *Basic Pathology*, 2d Ed., W.B. Saunders Co., Philadelphia, pp. 112-113) etc.)

In another specific embodiment, a Therapeutic of the invention is administered to a human patient to prevent progression to kidney, cartilage (of the breast bone), skin, skeletal muscle, lung, or spleen of cancer, melanoma, or sarcoma.

5.8.1.3 Hyperproliferative and Dysproliferative Disorders

In another embodiment of the invention, a Therapeutic that promotes Nogo activity is used to treat or prevent hyperproliferative or benign dysproliferative disorders. Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.8.1.4 Gene Therapy

In a specific embodiment, nucleic acids comprising a sequence encoding a Nogo protein or functional derivative thereof, are administered to promote Nogo function, by way of gene therapy. Gene therapy refers to therapy performed by the administration of a nucleic acid to a subject. In this embodiment of the invention, the nucleic acid produces its encoded protein that mediates a therapeutic effect by promoting Nogo function.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11 (5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the Therapeutic comprises a Nogo nucleic acid that is part of an expression vector that expresses a Nogo protein or fragment or chimeric protein thereof in a suitable host. In particular, such a nucleic acid has a promoter operably linked to the Nogo coding region, said promoter being inducible or constitutive, and, optionally, tissue-specific. In another particular embodiment, a nucleic acid molecule is used in which the Nogo coding sequences and any other desired sequences are flanked by regions that promote homologous recombination at a desired site in the genome, thus providing for intrachromosomal expression of the Nogo nucleic acid (Koller and Smithies, 1989, Proc. Natl. Acad. Sci. USA 86:8932-8935; Zijlstra et al., 1989, Nature 342: 435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429-4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, a viral vector that contains the Nogo nucleic acid is used. For example, a retroviral vector can be used (see Miller et al., 1993, Meth. Enzymol. 217:581-599). These retroviral vectors have been modified to delete retroviral sequences that are not necessary for packaging of the viral genome and integration into host cell DNA. The Nogo nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to the central nervous system. Adenoviruses naturally infect respiratory epithelia where they cause a mild disease. Other targets for adenovirus-based delivery systems are liver, the respiratory epithelia, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234.

In addition to Adenoviruses, Adeno-associated virus (AAV) has also been proposed for use in gene therapy (Walsh et al., 1993, Proc. Soc. Exp. Biol. Med. 204:289-300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a Nogo nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to neural stem cells (Stemple and Anderson, 1992, Cell 71:973-985).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a Nogo protein or functional derivative.

5.8.2 Treatment and Prevention of Disorders in which Nogo Blocks Regeneration Diseases and disorders in which neurite extension, growth or regeneration are desired are treated by administration of a Therapeutic that antagonizes (inhibits) Nogo function. The diseases, disorders or damage which ultimately result in damage of the nervous system include, but are not limited to, central nervous system (CNS) trauma, (e.g. spinal cord or brain injuries), infarction, infection, malignancy, exposure to toxic agents, nutritional deficiency, paraneoplastic syndromes, and degenerative nerve diseases (including but not limited to Alzheimer's disease, Parkinson's disease, Huntington's Chorea, multiple sclerosis, amyotrophic lateral sclerosis, and progressive supra-nuclear palsy); by administering compounds that interfere with Nogo activity (e.g., a dominant negative Nogo derivative; antibodies to Nogo; anti-sense nucleic acids that encode Nogo; Nogo ribozymes or chemical groups that bind an active site of Nogo).

Therapeutics that can be used include but are not limited to Nogo antisense nucleic acids, and Nogo nucleic acids that are dysfunctional (e.g., due to a heterologous (non-Nogo sequence) insertion within the Nogo coding sequence) that are used to "knockout" endogenous Nogo function by homologous recombination (see, e.g., Capecchi, 1989, Science 244:1288-1292). Anti-Nogo antibodies (and fragments and derivatives thereof containing the binding region thereof) can be used as an antagonist of Nogo. In a specific embodiment of the invention, a nucleic acid containing a portion of a Nogo gene in which Nogo sequences flank (are both 5' and 3' to) a different gene sequence, is used, as a Nogo antagonist, to promote Nogo inactivation by homologous recombination (see also Koller and Smithies, 1989, Proc. Natl. Acad. Sci. USA 86:8932-8935; Zijlstra et al., 1989, Nature 342:435-438). Other Therapeutics that inhibit Nogo function can be identified by use of known convenient in vitro assays, e.g., based on their ability to inhibit binding of Nogo to another protein, or inhibit any known Nogo function, as preferably assayed in vitro or in cell culture, although genetic assays may also be employed. Preferably, suitable in vitro or in vivo assays, are utilized to determine the effect of a specific Therapeutic and whether its administration is indicated for treatment of the affected tissue.

In specific embodiments, Therapeutics that inhibit Nogo function are administered therapeutically (including prophylactically): (1) in diseases or disorders involving an increased (relative to normal or desired) level of Nogo protein or function, for example, in patients where Nogo protein is overactive or overexpressed; or (2) in diseases or disorders wherein in vitro (or in vivo) assays (see infra) indicate the utility of Nogo antagonist administration. The increased levels in Nogo protein or function can be readily detected, e.g., by quantifying protein and/or RNA, by obtaining a patient tissue sample (e.g., from biopsy tissue) and assaying it in vitro for RNA or protein levels, structure and/or activity of the expressed Nogo RNA or protein. Many methods standard in the art can be thus employed, including but not limited to kinase assays, immunoassays to detect and/or visualize Nogo protein (e.g., Western blot, immunoprecipitation followed by sodium dodecyl sulfate polyacrylamide gel electrophoresis, immunocytochemistry, etc.) and/or hybridization assays to detect Nogo expression by detecting and/or visualizing respectively Nogo mRNA (e.g., Northern assays, dot blots, in situ hybridization, etc.), etc.

5.8.2.1 Antisense Regulation of Nogo Expression

In a specific embodiment, Nogo function is inhibited by use of Nogo antisense nucleic acids. The present invention provides the therapeutic or prophylactic use of nucleic acids of at least six nucleotides that are antisense to a gene or cDNA encoding Nogo or a portion thereof. A Nogo "antisense" nucleic acid as used herein refers to a nucleic acid capable of hybridizing to a portion of a Nogo RNA (preferably mRNA) by virtue of some sequence complementarity. The antisense nucleic acid may be complementary to a coding and/or non-coding region of a Nogo mRNA. Such antisense nucleic acids have utility as Therapeutics that inhibit Nogo function, and can be used in the treatment or prevention of disorders as described supra.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Nogo antisense nucleic acids provided by the instant invention can be used to promote regeneration of neurons of the central nervous system in particular, including regeneration of the corticospinal tract, plasticity during recovery, regrowth of neurons and healing of damage associated with traumatic injuries, strokes, and neurodegenerative diseases.

The invention further provides pharmaceutical compositions comprising an effective amount of the Nogo antisense nucleic acids of the invention in a pharmaceutically acceptable carrier, as described infra.

In another embodiment, the invention is directed to methods for inhibiting the expression of a Nogo nucleic acid sequence in a prokaryotic or eukaryotic cell comprising providing the cell with an effective amount of a composition comprising an Nogo antisense nucleic acid of the invention.

Nogo antisense nucleic acids and their uses are described in detail below.

5.8.2.1.1 Nogo Antisense Nucleic Acids

The Nogo antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549).

In a preferred aspect of the invention, a Nogo antisense oligonucleotide is provided, preferably of single-stranded DNA. In a most preferred aspect, such an oligonucleotide comprises a sequence antisense to the sequence near one of the two promoter sequences of the Nogo gene, or a sequence encoding carboxy-terminal portion of the Nogo gene. It may be desirable to selectively inhibit the expression one of the Nogo isoforms. The oligonucleotide may be modified at any position on its structure with substituents generally known in the art.

The Nogo antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

In a specific embodiment, the Nogo antisense oligonucleotide comprises catalytic RNA, or a ribozyme (see, e.g., PCT International Publication WO 90/11364, published Oct. 4, 1990; Sarver et al., 1990, Science 247:1222-1225). In another embodiment, the oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

In an alternative embodiment, the Nogo antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Nogo antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the Nogo antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc.

The antisense nucleic acids of the invention comprise a sequence complementary to at least a portion of an RNA transcript of a Nogo gene, preferably a human Nogo gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Nogo antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Nogo RNA it may contain and still form a stable duplex (or triplex, as the case may be). One skilled in the art can ascertain a tolerable degree of mismatch by use of standard procedures to determine the melting point of the hybridized complex.

5.8.2.1.2 Therapeutic Use of Nogo Antisense Nucleic Acids

The Nogo antisense nucleic acids can be used to treat (or prevent) disorders of a cell type that expresses, or preferably overexpresses, Nogo. In a specific embodiment, such a disorder is a growth proliferative disorder. In a preferred embodiment, a single-stranded DNA antisense Nogo oligonucleotide is used.

Cell types which express or overexpress Nogo RNA can be identified by various methods known in the art. Such methods include but are not limited to hybridization with a Nogo-specific nucleic acid (e.g. by Northern hybridization, dot blot hybridization, in situ hybridization), observing the ability of RNA from the cell type to be translated in vitro into Nogo, immunoassay, etc. In a preferred aspect, primary tissue from a patient can be assayed for Nogo expression prior to treatment, e.g., by immunocytochemistry or in situ hybridization.

Pharmaceutical compositions of the invention, comprising an effective amount of a Nogo antisense nucleic acid in a pharmaceutically acceptable carrier, can be administered to a patient having a disease or disorder which is of a type that expresses or overexpresses Nogo RNA or protein.

The amount of Nogo antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Nogo antisense nucleic acids are administered via liposomes, microparticles, or microcapsules. In various embodiments of the invention, it may be useful to use such compositions to achieve sustained release of the Nogo antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448-2451; Renneisen et al., 1990, J. Biol. Chem. 265:16337-16342).

5.9 Demonstration of Therapeutic or Prophylactic Utility

The Therapeutics of the invention are preferably tested in vitro, and then in vivo for the desired therapeutic or prophylactic activity, prior to use in humans. For example, in vitro assays which can be used to determine whether administration of a specific Therapeutic is indicated, include in vitro cell culture assays in which a patient tissue sample is grown in culture, and exposed to or otherwise administered a Therapeutic, and the effect of such Therapeutic upon the tissue sample is observed. For example, a Therapeutic that is an inhibitor of Nogo function can be assayed by measuring neurite regrowth or functional recovery of motor control in the patient.

In various specific embodiments, in vitro assays can be carried out with representative cells of cell types involved in a patient's disorder, to determine if a Therapeutic has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.10 Therapeutic/Prophylactic Administration and Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429-4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.11 Diagnosis and Screening

Nogo proteins, analogues, derivatives, and subsequences thereof, Nogo nucleic acids (and sequences complementary thereto), anti-Nogo antibodies, have uses in diagnostics. Such molecules can be used in assays, such as immunoassays, to detect, prognose, diagnose, or monitor various conditions, diseases, and disorders affecting Nogo expression, or monitor the treatment thereof. In particular, such an immunoassay is carried out by a method comprising contacting a sample derived from a patient with an anti-Nogo antibody under conditions such that immunospecific binding can occur, and detecting or measuring the amount of any immunospecific binding by the antibody. In a specific aspect, such binding of antibody, in tissue sections, can be used to detect aberrant Nogo localization or aberrant (e.g., low or absent) levels of Nogo. In a specific embodiment, antibody to Nogo can be used to assay in a patient tissue or serum sample for the presence of Nogo where an aberrant level of Nogo is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as immunohistochemistry, pathology, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunohistochemistry assays, protein A immunoassays, to name but a few.

Nogo genes and related nucleic acid sequences and subsequences, including complementary sequences, can also be used in hybridization assays. Nogo nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Nogo expression and/or activity as described supra. In particular, such a hybridization assay is carried out by a method comprising contacting a sample containing nucleic acid with a nucleic acid probe capable of hybridizing to Nogo DNA or RNA, under conditions such that hybridization can occur, and detecting or measuring any resulting hybridization.

In specific embodiments, diseases and disorders involving cellular growth and development disorders can be diagnosed, or their suspected presence can be screened for, or a predisposition to develop such disorders can be detected, by detecting decreased levels of Nogo protein, Nogo RNA, or Nogo functional activity as demonstrated growth inhibition, or by detecting mutations in Nogo RNA, DNA or protein (e.g., translocations in Nogo nucleic acids, truncations in the Nogo gene or protein, changes in nucleotide or amino acid sequence relative to wild-type Nogo) that cause decreased expression or activity of Nogo. Such diseases and disorders include but are not limited to those described in Section 3 and Section 5.8.1.1. By way of example, levels of Nogo protein can be detected by immunoassay, levels of Nogo RNA can be detected by hybridization assays (e.g., Northern blots, dot blots), Nogo binding to cellular growth inhibitor protein receptors can be done by binding assays commonly known in the art, translocations and point mutations in Nogo nucleic acids can be detected by Southern blotting, RFLP analysis, PCR using primers that preferably generate a fragment spanning at least most of the Nogo gene, sequencing of the Nogo genomic DNA or cDNA obtained from the patient, etc.

Kits for diagnostic use are also provided, that comprise in one or more containers an anti-Nogo antibody, and, optionally, a labeled binding partner to the antibody. Alternatively, the anti-Nogo antibody can be labeled (with a detectable marker, e.g., a chemiluminescent, enzymatic, fluorescent, or radioactive moiety). A kit is also provided that comprises in one or more containers a nucleic acid probe capable of hybridizing to Nogo RNA. In a specific embodiment, a kit can comprise in one or more containers a pair of primers (e.g., each in the size range of 6-30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320, 308) use of Qβ replicase, cyclic probe reaction, or other methods known in the art] under appropriate reaction conditions of at least a portion of a Nogo nucleic acid. A kit can optionally further comprise in a container a predetermined amount of a purified Nogo protein or nucleic acid, e.g., for use as a standard or control.

5.12 Screening for Nogo Agonists and Antagonists

Nogo nucleic acids, proteins, and derivatives also have uses in screening assays to detect molecules that specifically bind to Nogo nucleic acids, proteins, or derivatives and thus have potential use as agonists or antagonists of Nogo, in particular, molecules that thus affect cellular growth regulation. In a preferred embodiment, such assays are performed to screen for molecules with potential utility as neural growth promoters for drug development. The invention thus provides assays to detect molecules that specifically bind to Nogo nucleic acids, proteins, or derivatives. For example, recombinant cells expressing Nogo nucleic acids can be used to recombinantly produce Nogo proteins in these assays, to screen for molecules that bind to a Nogo protein. Molecules (e.g., putative binding partners of Nogo) are contacted with the Nogo protein (or fragment thereof) under conditions conducive to binding, and then molecules that specifically bind to the Nogo protein are identified. Similar methods can be used to screen for molecules that bind to Nogo derivatives or nucleic acids. Methods that can be used to carry out the foregoing are commonly known in the art.

By way of example, diversity libraries, such as random or combinatorial peptide or nonpeptide libraries can be screened for molecules that specifically bind to Nogo. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152:149-157; Kay et al., 1993, Gene 128:59-65; and PCT Publication No. WO 94/18318 dated Aug. 18, 1994.

in vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. Nos. 5,096,815, 5,223,409, and 5,198,346, all to Ladner et al.; Rebar and Pabo, 1993, Science 263:671-673; and PCT Publication No. WO 94/18318.

In a specific embodiment, screening can be carried out by contacting the library members with a Nogo protein (or nucleic acid or derivative) immobilized on a solid phase and harvesting those library members that bind to the protein (or nucleic acid or derivative).

Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited hereinabove.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to a Nogo protein or derivative.

5.13 Animal Models

The invention also provides animal models, including but not limited to models in mice, hamsters, sheep, pigs, cattle, and preferably non-human mammals.

In one embodiment, animal models for diseases and disorders involving neurite extension, growth and regeneration are provided. Such an animal can be initially produced by promoting homologous recombination between a Nogo gene in its chromosome and an exogenous Nogo gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated Nogo gene, such that homologous recombination occurs, followed by injecting the ES cells into a blastocyst, and implanting the blastocyst into a foster mother, followed by the birth of the chimeric animal ("knockout animal") in which a Nogo gene has been inactivated (see Capecchi, 1989, Science 244:1288-1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving the central nervous system and thus can have use as animal models of such diseases and disorders, e.g., to screen for or test molecules (e.g., potential nervous system disorder therapeutics) for the ability to inhibit tumors of nerve tissue and thus treat or prevent such diseases or disorders.

The present invention is not to be limited in scope by the microorganism deposited or the specific embodiments described herein. Indeed, various modifications of the invention in addition to those described herein will become apparent to those skilled in the art from the foregoing description and accompanying Figures. Such modifications are intended to fall within the scope of the appended claims.

Various references are cited herein, the disclosures of which are incorporated by reference in their entireties.

6. EXAMPLE

Characterization of the Nucleotide and Protein Product of the Nogo Gene

The examples described herein demonstrate that the cloned gene, Nogo, encodes a protein that is a potent neural cell growth inhibitor and is also recognized by the monoclonal antibodies described in Schwab et al., U.S. Pat. No. 5,684,133.

6.1 Materials and Methods

The following sections describe materials and methods used in the present invention. One of ordinary skill in the art will recognize that these materials and methods are merely illustrative of the presently claimed invention and modifications are envisioned by the present inventors. Such modifications are intended to fall within the scope of the appended claims.

6.1.1 Purification of Bovine Nogo from Myelin

All purification steps were carried out at 4° C. and inhibitory substrate activity of the obtained fractions was routinely determined by the NIH 3T3 spreading and PC12 neurite outgrowth assays (Section 6.1.10). Bovine spinal cord tissue was carefully cleaned by stripping off the meninges and cut into small pieces. The myelin was then extracted in extraction buffer (60 mM CHAPS, 100 mM Tris-Cl, pH 8.0, 10 mM EDTA buffer, pH 8.0, 2.5 mM iodacetamide, 1 mM phenylmethylsulfonyl fluoride, 0.1 µg/ml aprotinin, 1 µg/ml leupeptin, 1 µg/ml peptstatin A).

To obtain spinal cord extract, the tissue was homogenized directly in CHAPS extraction buffer in a ratio of (1:1; w:v). The homogenate was centrifuged twice at 100,000×g (Kontron type: K50.13, fixed angle) for 1 hour at 4° C. The clear supernatant (extract) was immediately applied to a Q-Sepharose column (2.6×11.5 cm), equlibrated in buffer A (20 mM Tris-Cl, pH 8.0, 0.5% (w/v) CHAPS). Bound proteins were eluted with a five-bed volume linear gradient from 0 to 1 M NaCl in buffer A (100 ml gradient in 50 minutes). Active fractions containing bovine NI220 eluted around 0.4 M NaCl and were pooled (q-pool 1) for subsequent applications on Superdex 200 (2.6×60 cm) column, equilibrated in buffer B (150 mM NaCl, 20 mM Tris-Cl, pH 8.0, 0.5% (w/v) CHAPS).

Active fractions, after gel filtration (s-pool 1), were separated by 6% SDS-PAGE under reducing conditions and low constant power (2 watts/gel) for a total of 2500 Volt-hours. Bands and gel regions were identified after Coomoassie Blue staining (0.1% w/v R250 in 50% methanol and 10% acetic acid), cut out, and extracted in 800 µl of gel elution buffer (0.5% (w/v) CHAPS, 20 mM Tris-Cl, pH 8.0, 10 mM EDTA, pH 8.0, 2.5 mM iodacetamide, 1 mM phenylmethylsulfonyl fluoride, 0.1 µg/ml aprotinin, 1 µg/ml leupeptin, 1 µg/ml peptstatin A) for at least 48 hours at 4° C.

6.1.2 Microsequencing of Purified Nogo

The IN-1 neutralizable active gel-eluted material of several gels was re-run on a 10% SDS-polyacrylamide gel under reducing conditions, and stained with 0.1% (w/v) Coomassie Blue R250 in 50% methanol and 10% acetic acid. The 220 KDa band was cut out, and endoproteinase Lys-C digestion (1:50 molar ratio) was performed directly in the gel. The sample was acidified and applied to a reverse phase high performance liquid chromatography column, peptides were separated with a linear gradient (0-100%) of 0.04% trifluoroacetic acid and 80% acetonitrile, and fractions containing single peptide species were subjected to automated Edman degradation.

6.1.3 Electrophoresis of Purified Nogo

High resolution SDS-PAGE was carried out using 6% (w/v) SDS-polyacrylamide gels (10×24×0.01 cm) under reducing conditions (100 mM dithiothreitol). Transfer onto Immobilon-P membranes (Millipore) was performed in 20 mM Tris base, 192 mM glycine, pH 8.3, 0.037% (w/v) SDS, 20% methanol with a semi-dry transfer apparatus (Bio-Rad, Trans Blot SD). Transfer time was 2 h at 0.8 mA/cm². Blocking reagent (1 hour at room temperature) was 3% gelatin in PBS (phosphate-buffered saline, pH 7.2, 8 g NaCl, 0.2 g of $kH_2PO_4$, 2.8 g of $NaHPO_4.12H_2O$, and 0.2 g of KCl, dissolved in 1 liter of water) and the washing solution contained 20 mM Tris-Cl, pH 7.5, 150 mM NaCl, and 0.4% Tween (3×10 minutes at room temperature). Incubation time for the first antibody (for dilution with 1% gelatin in PBS) was usually overnight at 4° C. Horseradish peroxidase-conjugated anti-mouse IgG secondary antibody (1:2000) was incubated for 1 hour at room temperature. The ECL chemiluminescence system was used for detection (Amersham Pharmacia Biotech).

6.1.4 cDNA Library Probing

White matter was freshly dissected from bovine spinal cord, and poly(A)⁺ RNA was extracted using the FastTrack kit (Invitrogen). Construction of cDNA libraries was performed using the Uni-ZAP kit (Stratagene) following the manufacture's. instructions. The complexity of the libraries was greater than 4×10⁶ plaque forming units in total, and the average size of the inserts was approximately 1.8 kilobases.

Degenerate oligonucleotides MSC5-8 (MSC5: TCIGTIGGYAAIACIGCIGGYAARTC (SEQ ID NO:47); MSC6: TCIGTIGGIAGIACIGCIGGYAAYTC (SEQ ID NO:48); MSC7: TCIGTIGGYAAIACIGCIGGIAGRTC (SEQ ID NO:49); MSC8: TCIGTIGGIAGIACIGCIGGIAGRTC (SEQ ID NO:50)) were designed from the bNI220 peptide 1 sequence, and MSC9 (GARATHGCIGAIATHCARGAYGGIGA (SEQ ID NO:51)) was designed from bNI220 peptide 2 sequence. Oligonucleotides were synthesized by MWG Biotech (Munchenstein, Switzerland) and labeled with the DIG DNA 3'-end labeling kit. Riboprobes were synthesized using the DIG RNA labeling kit (Boehringer Mannheim).

Probe hybridization and washing conditions were as described by the manufacturer (MSC5-8 and MSC9 were used at a hybridization and washing temperature of 57° C.). Probe detection was performed using the CDP-star system (Boehringer Mannheim). CDNA library handling and screening was done according to the protocols for lambda ZAP CDNA libraries (Stratagene). Genescreen (DuPont) nylon membranes were used for plaque lifts.

6.1.5 DNA Sequencing

Both strands of CWP1-3, Oli18, Oli3, and R1-3U21 were sequenced with the Perkin Elmer AB1377 system by Microsynth (Balgach, Switzerland). DNA sequences were analyzed by the DNASIS program (Hitachi). Database searches were performed with the BLAST program (NCBI).

6.1.6 RNA Analysis

Total RNA and poly(A)⁺ RNA were extracted from tissues using the RNAgent (Promega) or FastTrack kit (Invitrogen), respectively. RNAs were separated by electrophoresis on 1% formaldehyde gels and transferred to Genescreen membranes. Blots were hybridized with antisense riboprobes, which were generated with the DIG RNA labeling kit (Boehringer Mannheim), from the relevant plasmids. Blot hybridization, washing, and CDP star-detection conditions were as described by the manufacturer. The 'common' probe, EST111410 (TIGR, ATCC, Rockville, Md., USA) contains transcript A sequence between nucleotides 2535-4678, the exon 1 specific probe contains transcript A sequence between nucleotides 65-769, and the exon 2 specific-probe contains transcript A sequence between nucleotides 815-3183.

6.1.7 Antisera Production

Antiserum 472 (AS 472) was generated by Research Genetics, Inc. (Huntsville Ala.; USA) against the synthetic peptide P472, SYDSIKLEPENPPPYEEA (bovine sequence; SEQ ID NO:33), which corresponds to rat Nogo amino acid sequence at 623 to 640 of SEQ ID NO:2, with three mismatches.

Antiserum Bruna (AS Bruna) was generated against a fragment of recombinant Nogo protein, expressed in *E. coli* as a fusion protein. Specifically, the carboxy-terminus of the rat Nogo A nucleotide sequence encoding amino acids 762 to 1,163 of SEQ ID NO:2 (expressed in *E. coli* using the Novagen pET system) was used to generate AS Bruna anti-Nogo antisera.

6.1.8 Electrophoresis and Western Blotting

SDS-PAGE and Western blotting was performed by standard methods well known to those skilled in the art. Antibodies were diluted as follows: AS Bruna 1: 7,500; AS 472 1:2,000; anti-myc (9E10) 1:5,000 (Invitrogen); anti-BiP 2 µg/ml (Stressgen); mAb IN-1 hybridoma supernatant was used undiluted. Secondary antibodies were: HRP conjugated anti-rabbit (Pierce; 1:20,000); anti-mouse I gM (1:50,000); and alkaline phosphatase conjugated anti-mouse (Milan Analytica AG, La Roche, Switzerland; 1:5,000).

6.1.9 Immunohistochemistry

Adult rat spinal cord or cerebellum was rapidly dissected, embedded in OTC compound and frozen at −40° C. Twenty post mortem sections were cut and fixed in ethanol/acetic acid at 40° C. Immunostaining was performed as described by Rubin et al., 1994, J. Neurocytol. 23:209-217, except that the quenching step was omitted. Alternatively, tissue sections were fixed by methanol (2 minutes at −20° C.), and immunostaining was carried out as per Rubin et al., supra. Primary antibodies used were (Antibody: (dilution)): Hybridoma supernatant of IN-1: (undiluted); AS Bruna: (1:5000); or affinity purified AS 472: (1:50).

6.1.10 NIH 3T3 Fibroblast Spreading Assay

NIH 3T3 fibroblasts were plated onto culture dishes pre-coated with 5 µg/well (=1 cm²) q-pool. Q-pool is the pooled active fractions of bovine spinal cord extract separated on a Q sepharose column. IN-1 was used as undiluted culture supernatant (1-10 µg/ml), AS Bruna and pre-immune serum were diluted 1:1000 in PBS, and AS 472 and pre-immune serum were diluted 1:500 in PBS. To compensate for activity variations in different q-pool preparations the number of inhibited, round cells plated on the q-pool was normalized to 100% and to 0% plated on buffer control (Spillman et al., 1998, J. Biol. Chem. 273:19283-93).

6.1.11 DRG Neurite Outgrowth Assay

Dorsal root ganglia (DRG)s were dissected from E16 embryonic chicken in Hank's balanced salt solution (HBSS), divided into two parts and plated on dishes pre-coated with q-pool in 100 µl F12 medium with 10% (FCS) and 1% methocel. Neurite outgrowth from individual DRGs was scored after 24 hours incubation at 37° C. in a semi-quantitative way using a scale of 0 (no outgrowth) to 4 (maximum outgrowth).

6.1.12 DRG/Optic Nerve Co-culture Assay

Optic nerves were dissected from adult rats, irradiated with 5500 Grays and injected either with AS 472 or the corresponding pre-immune serum (1:10 dilution). Pairs of nerves were cultured in 3-chamber cultures such that one end of each nerve reached through a silicon grease/teflon ring barrier into the middle chamber, where dissociated cultured primary DRGs neurons from P0 rats were placed. After two weeks in culture, the nerves were fixed by standard techniques known in the art and embedded for electron microscopy (EM), and ultrathin sections were taken at a distance of about 3.5 mm from the DRG-exposed stump. Sections were systematically analyzed for the presence of regrowing axons using a Zeiss EM 902.

6.1.13 Nogo a Expression in COS Cells

The Nogo A open reading frame was subcloned into the pcDNA3.1mychis vector (Invitrogen) using standard cloning techniques known in the art. The resulting plasmid (Nogo-myc19) gave rise to a recombinant protein containing the Nogo A sequence fused to the myc-his tag (21 amino acids). Nogo-myc19 (2 µg DNA per 35 mm dish) or control plasmid (pcDNAmychisLacZ) were transfected into COS cells using superfect (Qiagen) according to the manufacturer's protocol. Transfected cells were harvested 36-48 hours after transfection. Based on immunofluorescent staining with anti-myc antibody and enzymatic β-galactosidase color reaction, the average transfection rate was estimated to be about 20%. Transfected COS cells were fixed with 95% ethanol/5% acetic acid (4° C., 25 minutes), blocked in PBS/10% FCS, and incubated with AS Bruna (1:200) or IN-1 (1:2) for 2 hours in PBS/1% FCS at room temperature. Cells were washed with PBS and reacted with fluorescent secondary antibodies (goat anti-rabbit-FITC for AS Bruna and goat anti-mouse-TRITC for IN-1 detection, Jackson Immuno Research Lab. Inc., West Grove, Pa.).

6.1.14 Oligodendrocyte Cultures

Oligodendrocytes isolated from new-born rat brain were plated on 75 cm$^2$ poly-lysine flasks (Sigma, St. Louis, Mo.) and cultured for 10-12 days in DMEM supplemented with 5% FCS. Enriched, mixed populations of oligodendrocytes and their progenitors were released from the astrocyte monolayer by shaking overnight at 210 rpm in an orbital shaker. The cells were plated at a density of 1-2×10$^6$ cells on poly-lysine coated 35 cm$^2$ dishes. Progenitors were allowed to differentiate in chemically defined medium (CDM) for 3-4 days.

6.1.15 Cell Surface Biotinylation

P4 rat whole brain cultures were prepared as described in van der Haar, et al. (1998, J. Neurosci. Res. 51:371-81). At day 7 in vitro they were biotinylated with the cell-impermeable EZ-LINK-Sulfo-NHS-LC-Biotin (Pierce) as described except that all steps were carried out at 15° C. and cells lysed in 1 ml of lysis buffer (0.05M NaH$_2$PO$_4$ pH8.0, 0.15M NaCl, 0.5% CHAPS (Sigma), 2.5 mM iodacetamide, 1 mM phenylmethylsulfonyl fluoride, 0.1 µg/ml aprotinin, 1 µg/ml leupeptin, 1 µg/ml pepstatin A). Biotinylated proteins were immunoprecipitated with Dynabeads M-280 Streptavidin (Dynal) subjected to SDS-PAGE and transferred to nitrocellulose membranes that were probed with AS472, α-BiP and α-β-tubulin. The membranes were stripped with Re-Blot Western Blot Recycling Kit (Chemicon).

6.1.16 Immunocytochemistry

Optic nerve oligodendrocytes were prepared as described in Schwab and Caroni (1988, J. Neurosci. 8:2381-2393). Two day-old cultures were incubated with AS 472 (1:200) or mAb IN-1 (1:3) in medium for 25 minutes at room temperature (rt). Cultures were washed, fixed with 4% paraformaldehyde/5% sucrose in PBS, and blocked in 0.1M maleic acid/2% blocking reagent (Boehringer Mannheim) for 1 hour. Secondary alkaline phosphatatase conjugated antibodies (Milan Analytica) were used at 1:7,500 in 0.1M maleic acid/1% blocking reagent (1 hour, rt). Transfected COS cells were fixed with 95% ethanol/5% acetic acid (4° C., 25 minutes), blocked, and incubated with AS Bruna (1:200) or mAb IN-1 for 2 hours at rt. Cells were reacted with goat anti-rabbit-FITC, and goat anti-mouse TRITC (Jackson Immuno Research Lab).

6.1.17 Optic Nerve Chamber

Pairs of optic nerve were cultured in a 3-chamber culture system as described in Schwab et al. (1988, J. Neurosci. 8:2381-2393), injected with and exposed to either AS 472 or the corresponding pre-immune serum (1:10). Optic nerves were embedded for electron microscopy (EM), and ultra-thin sections were taken at a distance of about 3.5 mm from the DRG-exposed stump. Sections were systematically analysed for the presence of regrowing axons using a Zeiss EM 902 microscope.

6.2 Experimental Results

The following section discloses the experimental results obtained from the methods sections set forth in 6.1 and subsections.

6.2.1 Isolation of Nogo CDNA

The bovine homologue of rat NI-250 was purified, bNI220, and peptides of the purified protein were generated by protease digestion. Multiple digoxygenin-labeled degenerate oligonucleotides were designed according to six different bNI220 peptide sequences. Several cDNA clones were isolated from the screening of a bovine white matter library using these oligonucleotides. The insert of the longest clone (CWP1-3, FIG. 1a) was used to synthesize probes for subsequent screening of rat cDNA libraries. Selected clones from such screenings are shown in FIG. 1a. DNA sequence analysis of these cDNA clones suggested that three different transcripts originate from one gene, and this gene was designated Nogo. The different transcripts likely result from both alternative promoter usage and alternative splicing (Nogo A, Nogo B and Nogo C; FIG. 1b). DNA sequences were compiled from the clones shown in FIG. 1A to create the transcript A, the DNA sequence of which is shown in FIG. 2a.

Conceptual translation of the three transcripts gives rise to protein products designated Nogo A (1163 amino acids), Nogo B (360 amino acids) and Nogo C (199 amino acids). Since Nogo A contains all six peptide sequences obtained from purified bNI220 (FIG. 2b), it is likely equivalent to the purified protein, rat NI-250. Nogo A, B, and C have a common carboxy terminus of 188 amino acids (the common domain), and Nogo A and B share an amino terminus of 172 amino acids. Nogo A is longer than Nogo B by 803 amino acids due to alternative splicing.

None of the Nogo isoforms possess a hydrophobic stretch of amino acids at the N-terminus, which could be used as a conventional signal peptide. However, proteins have been described which lack a conventional signal peptide but are still transferred through membranes, for example fibroblast growth factor (Florkiewicz et al., 1995, J. Cell. Physiology 162:388-399), ciliary neurotrophic factor (Sendtner et al., 1994, J. Neurobiology 25:1436-1353) and interleukin-1 (Rubartelli et al., 1990, EMBO J. 9:1503-1510). Membrane proteins such as commissureless (Tear et al., 1996, Neuron 16:501-514) also lack a conventional signal peptide yet are inserted into the membrane.

Although there is no in-frame stop codon in the putative 5'-untranslated region which would unequivocally define the start codon, the following evidence suggests that the methionine indicated in FIG. 2a is the start codon for Nogo A and Nogo B: (1) The sequence around this presumed start codon conforms well with the consensus sequence for translation start sites (GCCGCC A/G CC<u>ATG</u>G; SEQ ID NO:39); (2) Extensive efforts were made to search for more upstream sequences by both library screening and 5'-RACE. None of these searches have resulted in the identification of more upstream sequences; and (3) Eukaryotic recombinant Nogo A expressed from the above mentioned methionine has an apparent molecular weight of about 200 kD, as estimated by SDS-PAGE, which is indistinguishable from endogenous Nogo A from rat oligodendrocytes (FIG. 11a).

6.2.2 Nogo Sequence Analysis

Nogo A contains seven potential N-glycosylation sites, however biochemical evidence indicates Nogo A does not have a major polysaccharide component. Nogo A also has nineteen recognition sites for PKC, and seven recognition sites for casein kinase II (FIG. 2a). All three Nogos have two common carboxy terminal hydrophobic domains of 35 and 36 amino acids, respectively. Either or both of them may be used as trans- or intra-membrane domains, which is consistent with the characterization of bNI220 as an integral membrane protein. Nogo A (as well as Nogo B and C) does not contain any motifs of known cell adhesion molecules, extracellular matrix proteins, or other guidance molecules.

Nogo sequences were used to search different databases for homologous genes, the carboxy terminals common domain of the three Nogo products is similar (62.5%) to an identified human gene, nsp (cl13 and s-rex in rat, and chs-rex in chicken) (FIG. 3). An EST from C. elegans and a Drosophila melanogaster EST also have significant similarity (16.6% and 13.6%, respectively) to both Nogo and nsp at this same region. The 180 amino acid carboxy terminal domains of both Nogos and Nsps are highly conserved across mammalian species (98.3% and 97.3%, respectively), which suggests that they may perform similar and essential functions. Outside of this region, the similarity for a given protein among species is also high (73% between rat and bovine Nogo A; 76.2% between NSP-A and S-rexb; 50% between Chs-rexb and NSP-A or S-rexb). The similarity between NSPs and Nogos are, however, limited to their carboxy terminal, hydrophobic, common domain (FIG. 3a), and to the acidic nature of the proteins outside of this conserved region. The NSPs (NSP-A, -B and -C) have been previously described as neuro-endocrine specific products with unknown functions. In situ hybridization and immunohistology showed a neuronal localization of NSPs in the nervous system. Another human gene, nsp-like-1, which also has a carboxy terminal hydrophobic region with 50% similarity to both Nsp and Nogo was recently identified.

6.2.3 Nogo Tissue Expression

The Nogo expression pattern was examined by Northern blotting and in situ hybridization. When a "common" probe (Section 6.1.6) was used, three major Nogo transcripts (Designated: A, 4.6 kb; B, 2.6 kb; and C, 1.7 kb) were detected in the optic nerve, the spinal cord, and the cerebral cortex (FIG. 4a). In dorsal root ganglia, only the two larger transcripts were detected. A 2.6 kb, major transcript was detected in PC12 cell, whereas a 4.6 kb band can be detected only after long exposures (FIG. 4a). In sciatic nerve, lower levels of transcripts were detected with the 2.6 kb band being the major transcript. When spinal cord and PC 12 cell poly (A)$^+$ RNA were hybridized to an exon 1 specific probe, only the 4.6 kb and the 2.6 kb transcripts were detected; when the hindbrain and skeletal muscle poly(A)$^+$ RNAs were hybridized to an exon 2-specific probe, only the 4.6 kb transcript in hindbrain was detected (FIG. 4b). These results verify the transcript map shown in FIG. 1B. Northern blotting results, however, also demonstrated that Nogo expression is not restricted to the nervous system (FIG. 4c); Nogo transcripts were also detected in skeletal muscle (1.7 kb), kidney (2.6 kb and 1.7 kb), cartilage (from the breastbone, 1.7 kb), skin (1.7 kb), lung (2.6 kb), and spleen (2.6 kb). Except for the skeletal muscle, which expresses Nogo C transcripts at a high level, the level of Nogo transcripts outside of the nervous system is lower than that of the nervous system. So far, the 4.6 kb Nogo A transcripts seem to be uniquely transcribed in the nervous system.

Figure 5C:
Figure 5F:
Figure 5B:
Figure 5E:
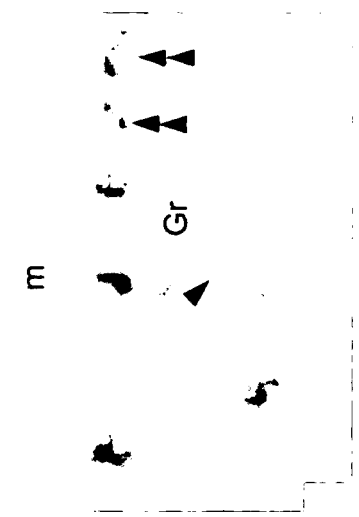
Figure 5A:
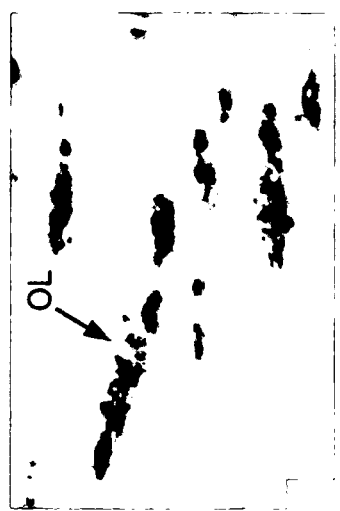
Figure 5D:
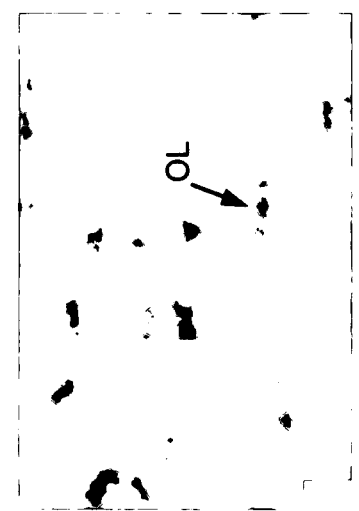

In situ hybridizations on adult rat CNS tissue sections using the common probe showed moderate labeling of rows of cell bodies in the white matter of various parts of the brain and the spinal cord. This arrangement is typical of interfascicular oligodendrocytes (FIG. 5a, d). In addition to oligodendrocytes, several types of neurons also express Nogo transcripts at high levels (FIG. 5c, e). In cerebellum, double staining of sections with an anti-GFAP antibody and in situ hybridization clearly showed a strong labeling of the Purkinje cells by the Nogo probe, whereas astrocytes were not labeled (FIG. 5e, f). In developing optic nerves, Nogo transcripts were detected as early as postnatal day 0 (P0), i.e., several days before the mRNAs of the major myelin proteins proteolipid protein (PLP) and myelin basic protein (MBP) can be detected (FIG. 6). This timing is consistent with the appearance of the first galactocerebroside-positive oligodendrocytes and the expression of a neurite growth inhibitory activity, which can be neutralized by IN-1.

Antisera were generated against a synthetic peptide based on a bovine Nogo A specific sequence (AS 472), and against a 45 kD recombinant, partial rat Nogo A (AS Bruna) (Section 6.1.7). AS 472 and AS Bruna each, recognized a protein of about 200 kD in bovine myelin, and AS Bruna further recognized a 200 kD rat myelin protein on Western blots (FIG. 7). Sections of adult rat spinal cord and cerebellum were stained with AS 472, AS Bruna, and IN-1. When the sections were fixed with ethanol/acetic acid (a procedure shown earlier to be required for preservation and accessibility of IN-1 antigens) strong staining of white matter/myelin was seen with all three antibodies (FIG. 8). Staining of oligodendrocyte cell bodies was particularly distinct with AS Bruna. Treatment of the fresh frozen sections with methanol instead of ethanol/acetic acid abolished the myelin stain except for oligodendrocyte cell bodies.

AS Bruna and AS 472 also stained some types of neurons including motor neurons in spinal cord, and granular and molecular layers in the cerebellum. Purkinje cells stained strongly with AS 472 and AS Bruna, but there was no detectable staining with IN-1.

6.2.4 Nogo Antibodies Inhibit Nogo Induced Growth Inhibition in Vitro

Semi-purified bovine spinal cord NI-220 preparations (q-pool) can prevent NIH 3T3 fibroblast spreading and neurite outgrowth. In the presence of Nogo antisera, either AS Bruna, AS 472, or IN-1, the q-pool inhibitory activity was reduced, i.e., NIH 3T3 fibroblasts underwent spreading and embryonic chicken dorsal root ganglia (DRG) extend neurites on dishes coated with q-pool (FIG. 9). Specificity was demonstrated by addition of peptide P472, which was the peptide used to raise AS 472 (Section 6.1.7). P472 successfully blocked the inhibitory effect of AS 472, whereas, a control peptide had no effect on the inhibition.

Figure 15A:
Figure 15B:
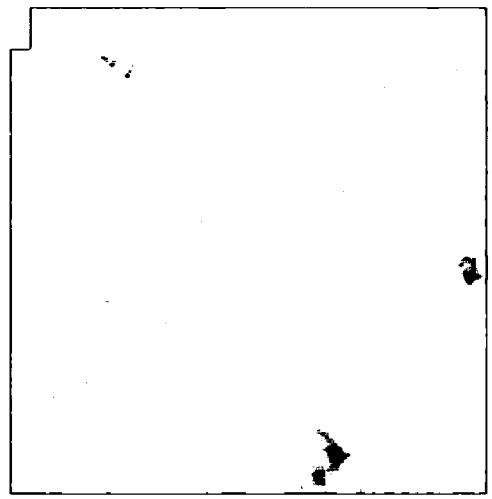
Figure 15C:
Figure 15D:
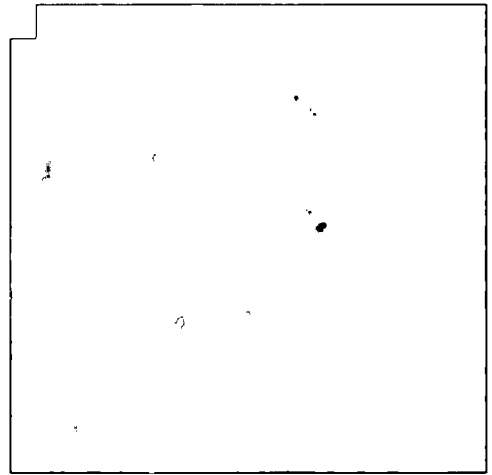
Figure 15E:
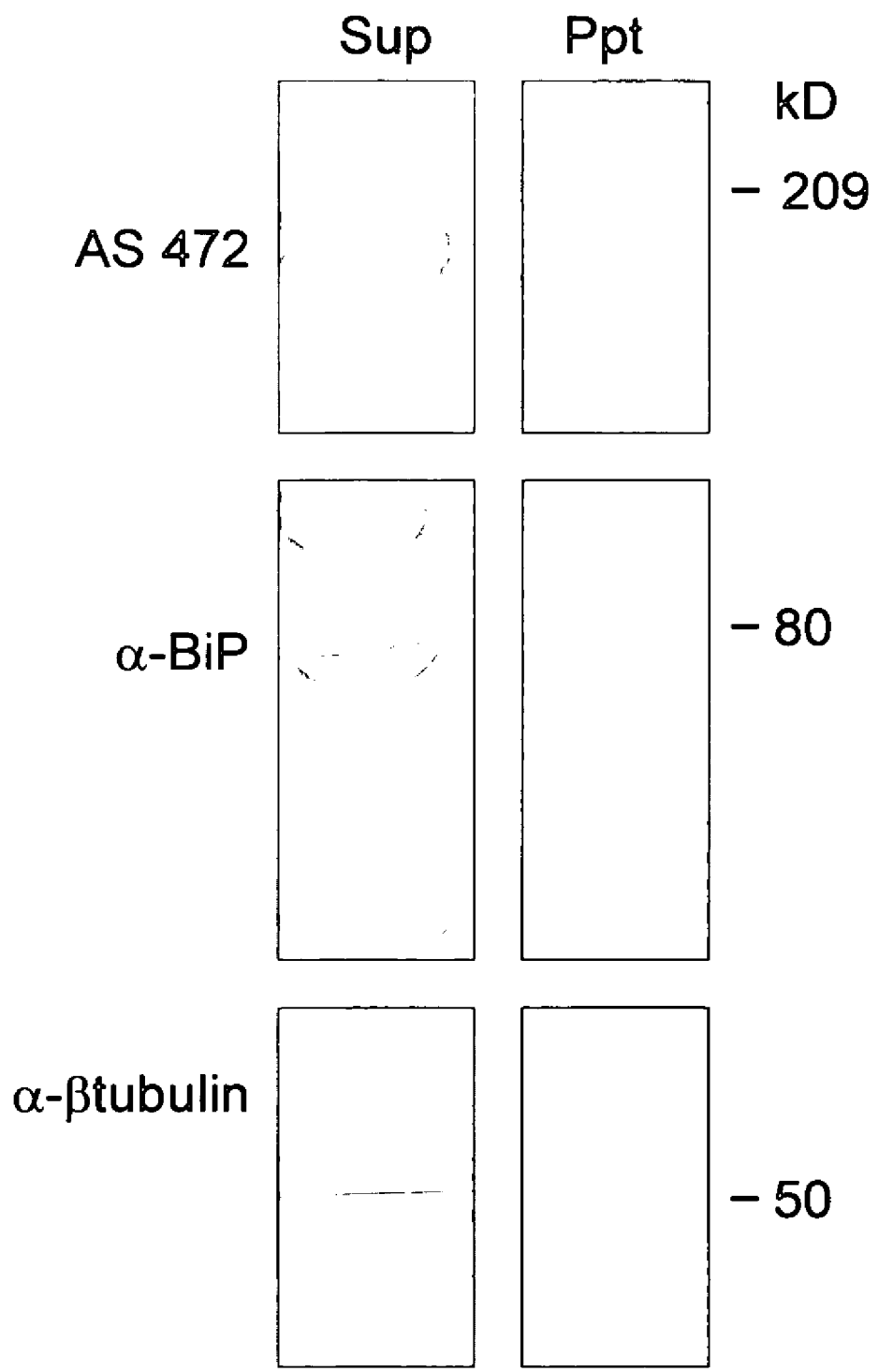

Furthermore, the presence of Nogo A on the cell surface of oligodendrocytes was demonstrated immunocytochemically, functionally and biochemically using AS 472. When live, primary cultured oligodendrocytes were stained with either mAb IN-1 or AS 472 a relatively weak (as compared to immunocytochemistry for galactocerebroside) but clear surface staining was observed on differentiated oligodendrocytes (FIG. 5a, c). Addition of the competing peptide (P472) for AS 472 or omitting the primary antibody abolished the specific staining (FIG. 15b, d). Cell surface biotinylation and subsequent precipitation with streptavidin further proved the presence of Nogo A on the plasma membrane of oligodendrocytes. In the precipitate, AS 472 detected a band running about 40 kD above the intracellular, probably non-processed and non-glycosylated AS 472 immuno-positive band. The ER protein BiP could not be detected in the biotinylated fraction (FIG. 15e).

Figure 16A:
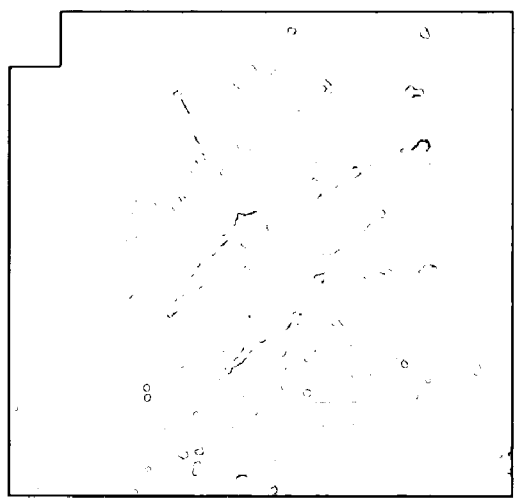
Figure 16B:
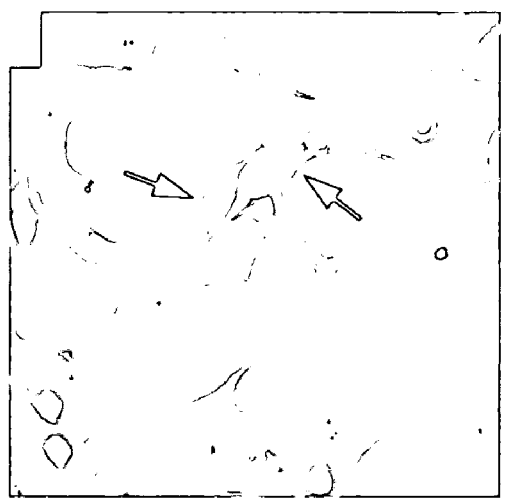
Figure 16C:
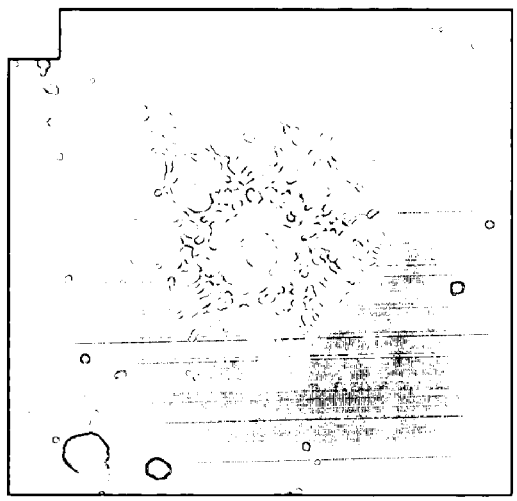
Figure 16D:
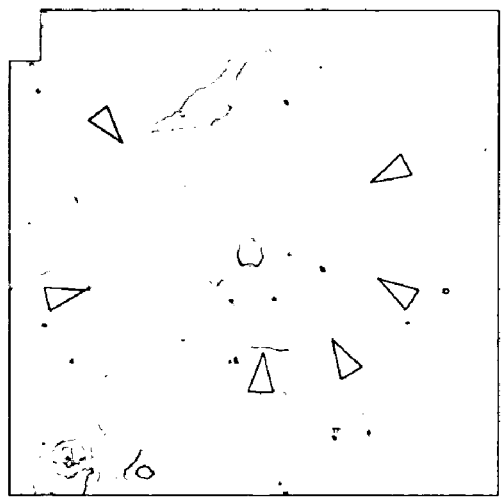
Figure 16E:
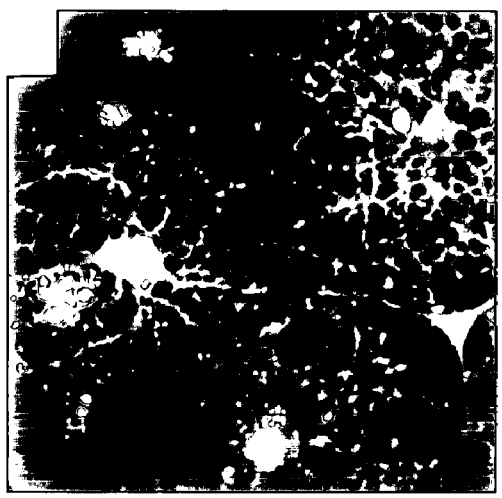
Figure 16F:
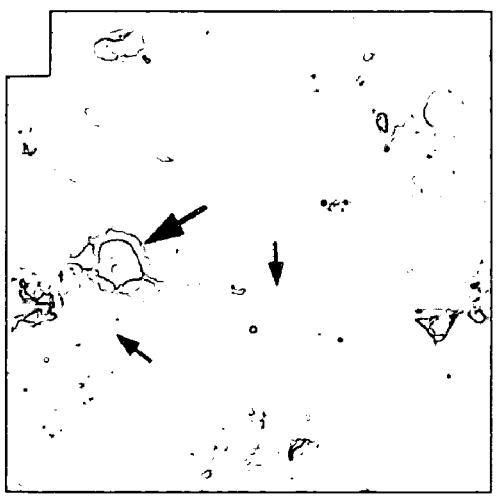
Figure 16G:
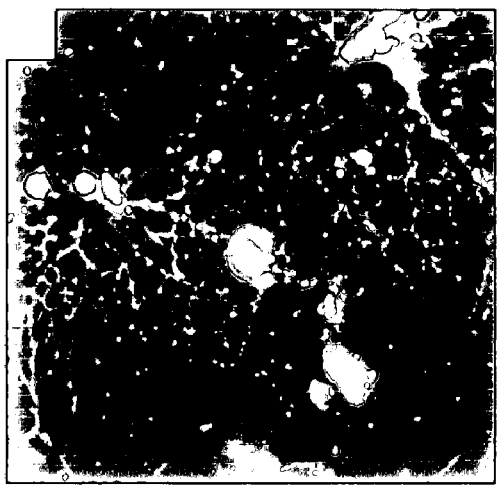
Figure 16H:
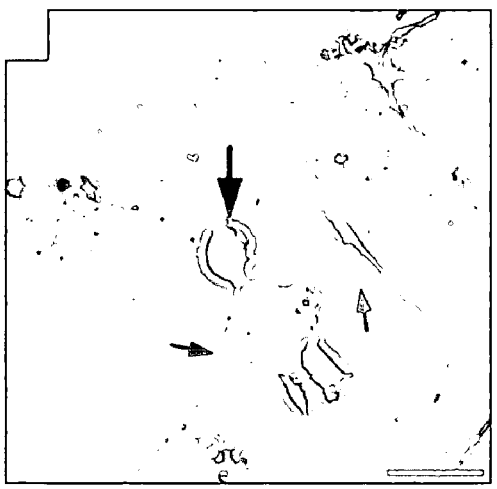
Figure 16I:
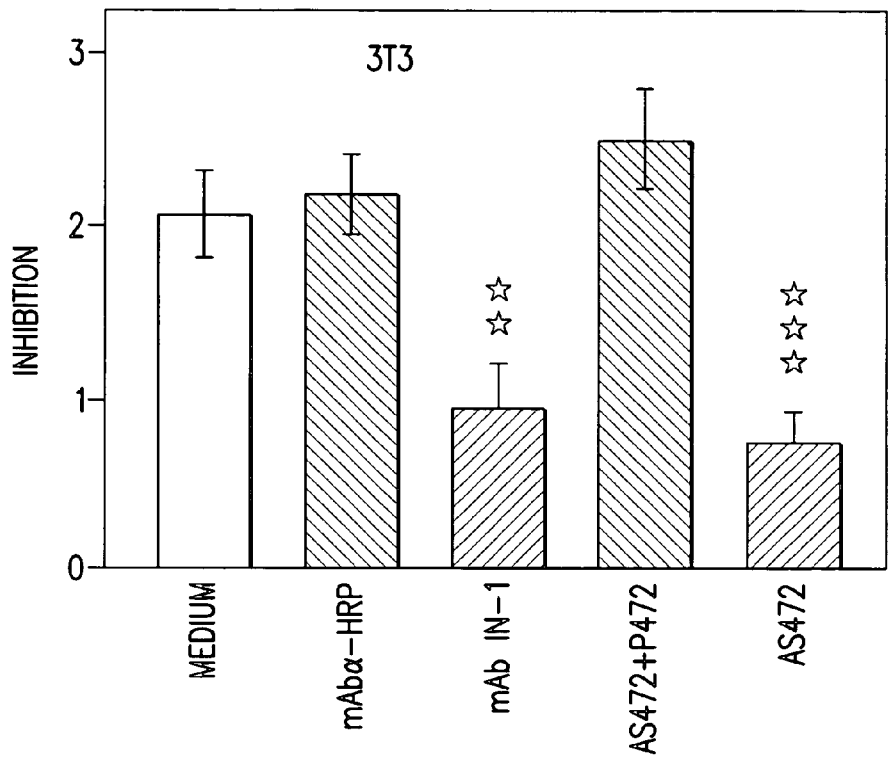
Figure 16J:
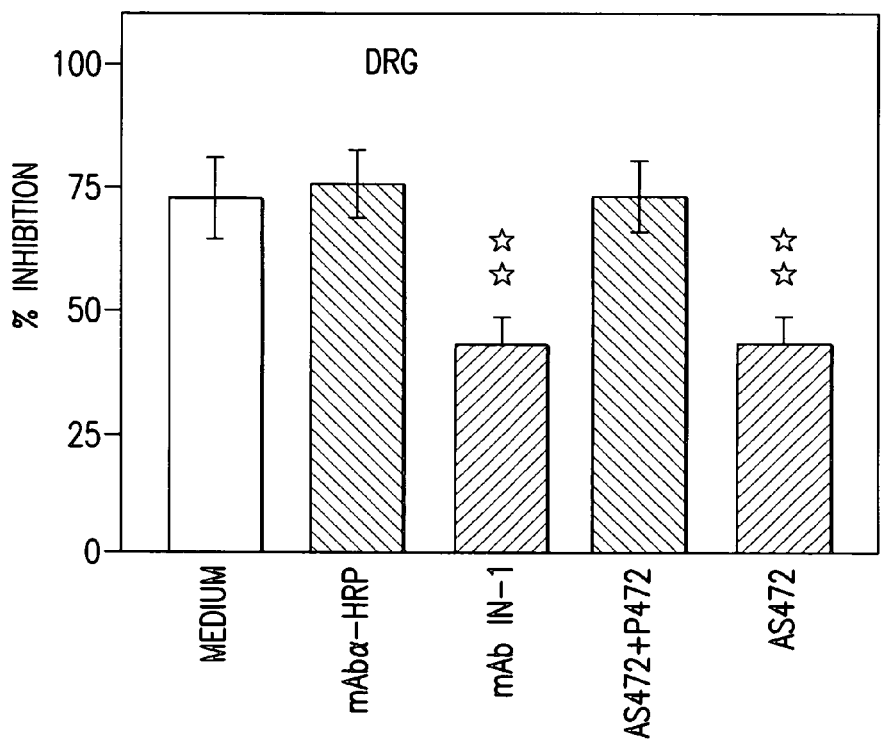

Nogo A as an oligodendrocyte cell surface molecule was also analyzed functionally. Co-culturing of oligodendrocytes and NIH 3T3 fibroblasts or oligodendrocytes and DRG neurons showed clearly the inhibitory properties of mature oligodendrocytes. These assays demonstrate that NIH 3T3 fibroblasts and DRG neurites strongly avoided the territory of the oligodendrocytes, an effect that was neutralized by mAb IN-1. In the presence of AS 472, this inhibition was equally reduced (FIGS. 16a, b and e, f), while preincubation of AS 472 with P472 restored the oligodendrocyte-mediated inhibition (FIGS. 16c, d and g, h). Quantification revealed the highly significant neutralizing capacity of mAb IN-1 and AS 472 in both types of assays (FIGS. 16i and j).

Figure 9A:
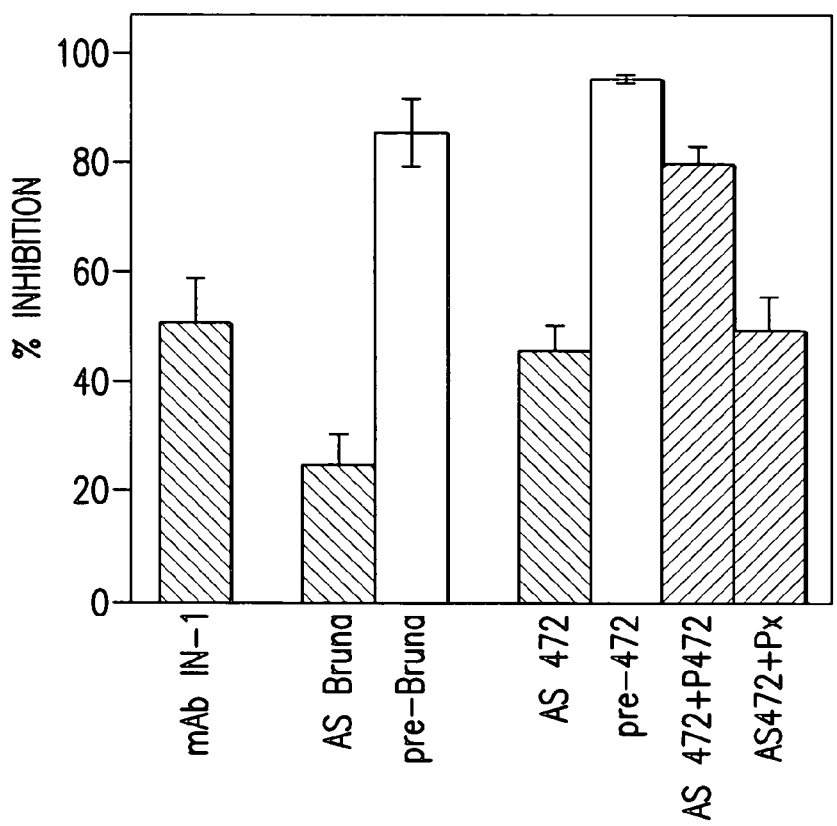
Figure 9B:
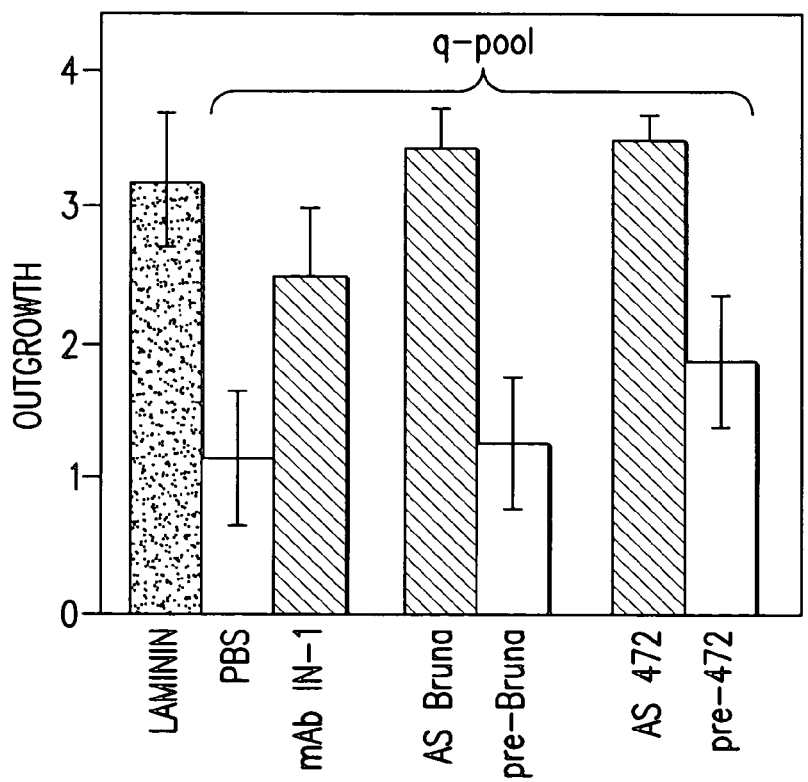
Figure 9D:
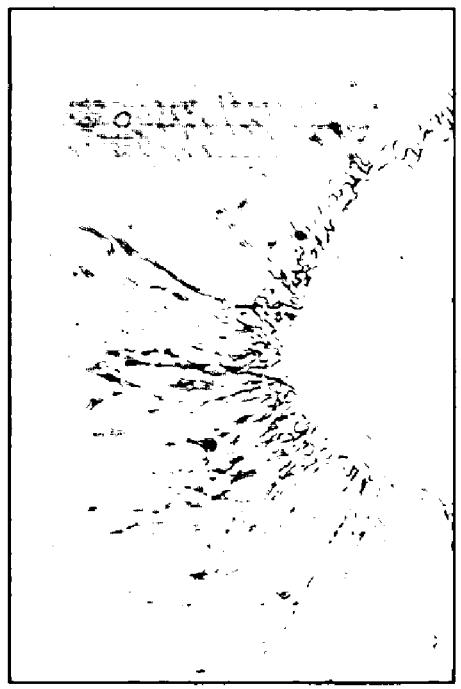
Figure 9C:
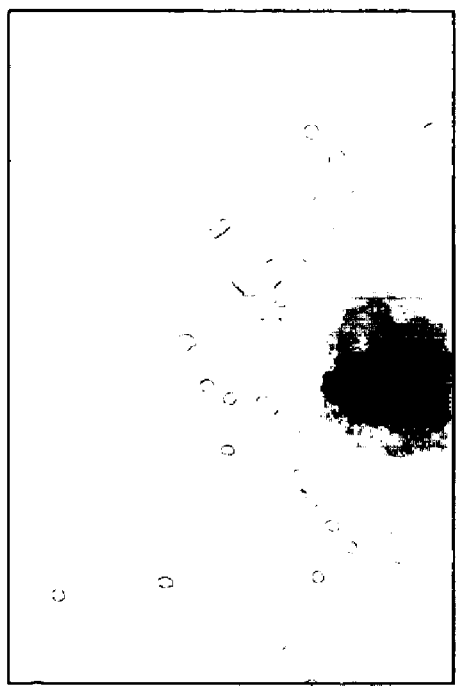
Figure 17A:
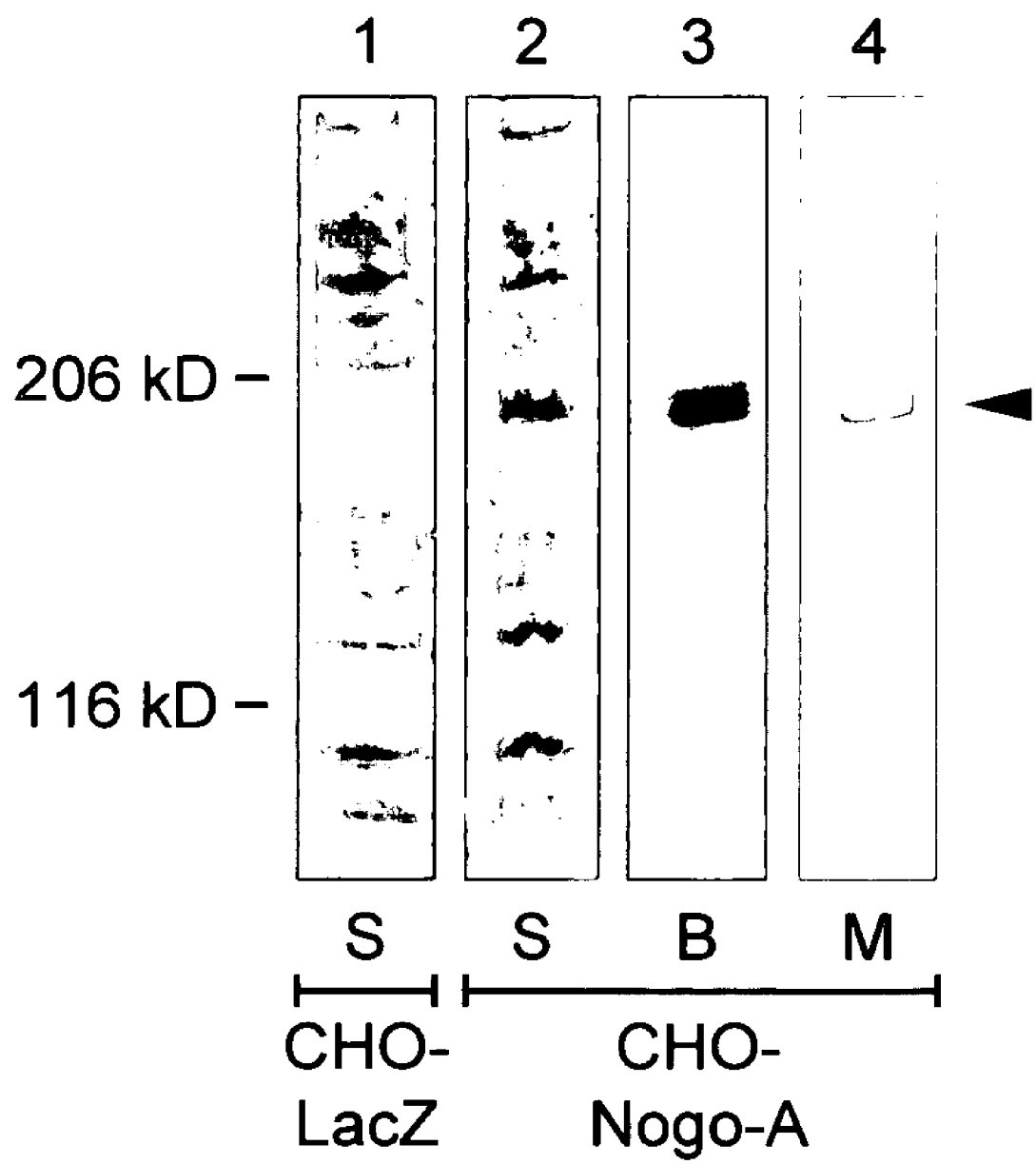
Figure 17B:
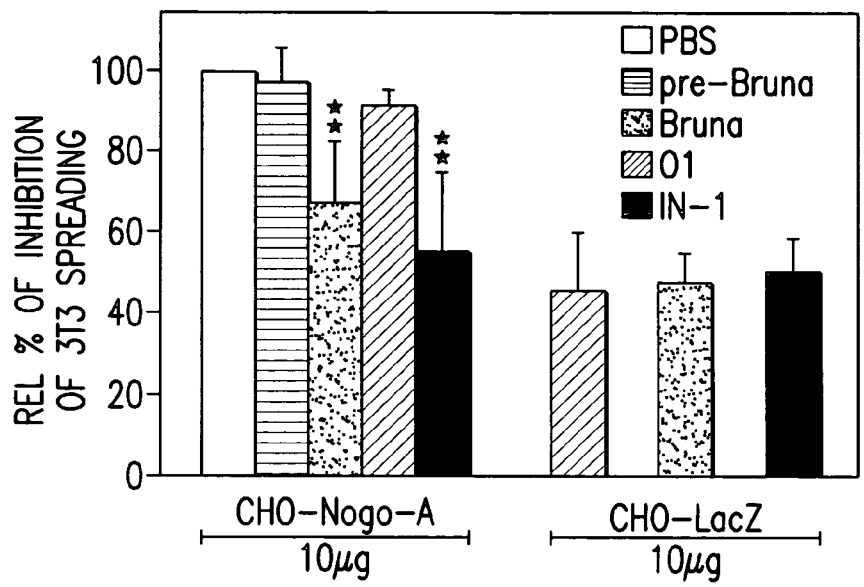

RecNogo-A (FIG. 17a) produced by a stably transfected CHO cell line was tested for its activity on NIH 3T3 fibroblast spreading and DRG neurite outgrowth. Recombinantly produced β-galactosidase isolated from a stable CHO cell line (CHO-LacZ) was enriched in parallel with recNogo-A and was used as a control for inhibitory activity of endogenous CHO proteins in both assays. In the NIH 3T3 fibroblast spreading assay, recNogo-A-containing CHO extract (Nogo-A: about 1-5% of total protein; FIG. 9a) exhibited clear inhibitory effects on cell spreading at 10 μg/cm² (FIG. 17b). This effect was dose-dependent: at 20 μg/cm² the inhibitory activity was higher, whereas 5 μg/cm² was not inhibitory (data not shown). The inhibitory activity could be neutralized to background levels by preincubation of the coated protein with mAb IN-1 or AS Bruna, whereas a control antibody against galactocerebroside (mAb O1) or AS Bruna preimmune serum had no effect (FIG. 17b).

Figure 17C:
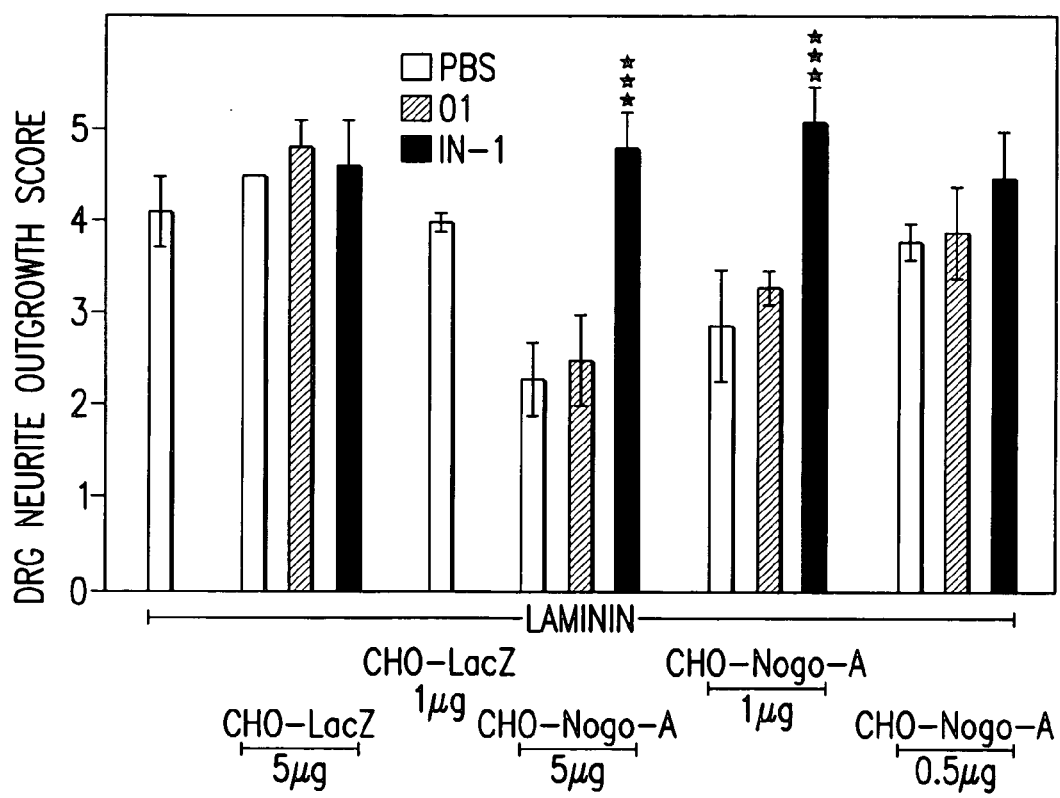
Figure 17E:
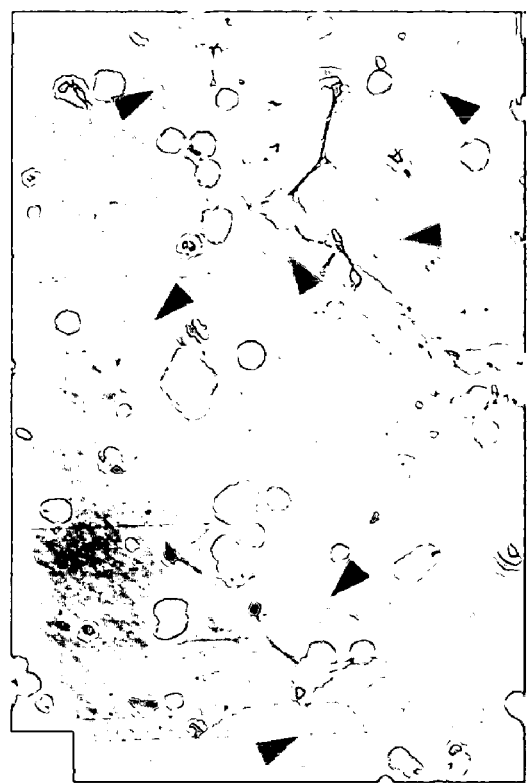
Figure 17D:

In addition to its strong effect on the NIH 3T3 fibroblast spreading, recNogo-A-containing CHO extract, but not CHO-LacZ extract had a potent inhibitory effect on neurite outgrowth from primary cultured neurons: Dissociated DRG neurons were inhibited by recNogo-A in a dose-dependent manner (FIG. 17c). This inhibitory activity could be neutralized by mAb IN-1, but not by the control mAb O1 (FIG. 17c-e). Recombinant protein isolated from CHO-LacZ was not inhibitory at 1 and 5 μg, and addition of mAbs O1 or IN-1 had no effect on neurite outgrowth.

6.2.5 Neurite Regrowth In Vitro

Figures 10A, 10B:
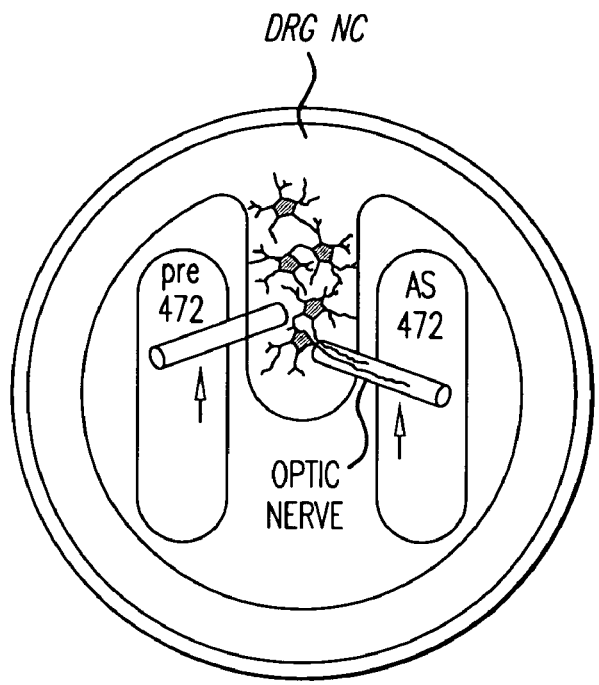
Figure 10C:
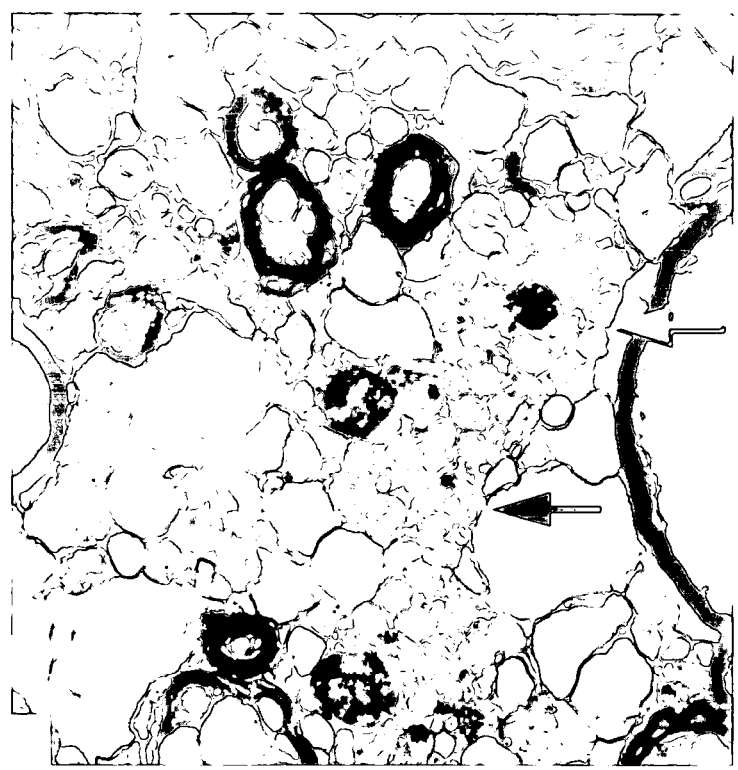
Figure 10D:

The ability of new-born rat DRG neurites to regenerate and grow through adult CNS tissue was investigated. Pairs of optic nerves were dissected from adult rats and cultured in a special chamber culture system such that DRG neurites had access to one end of each nerve (FIG. 10a). In each culture, one of the two nerves was injected with and exposed to pre-immune rabbit serum, the second nerve was injected with AS 472, which was also present in the side chamber around the nerve. Following two weeks in vitro in the presence of NGF, the cultures were fixed, disassembled, and embedded for electron microscopy (EM). EM sections were taken about 3.5 mm from the end of the nerve in contact with DRG neurons. Pre-immune serum injected nerves contained no or only a few axons (FIG. 10b). The latter were exclusively found associated with basement membranes and astrocytes at the surface of the nerves. In contrast, the majority of the optic nerves injected with AS 472 contained considerable numbers of axons, often up to several hundred. Contact with myelin could frequently be seen (FIGS. 10c, d).

6.2.6 Recombinant Nogo a Recognition by IN-1

When Nogo A was expressed as a carboxy terminal myc-his-tagged recombinant protein in transfected-COS cells, western blotting using both anti-myc antibody and AS Bruna demonstrated that the recombinant Nogo A has an apparent molecular weight of about 200 kD on denaturing SDS gels (FIG. 11a). On the same blot, a band of similar mobility was detected by AS Bruna in rat primary culture oligodendrocytes, suggesting that recombinant Nogo A has a nearly identical molecular weight as the endogenous Nogo A from oligodendrocytes (FIG. 1a). When transfected COS cells were stained by immunofluorescence with IN-1 and AS Bruna, IN-1 and AS Bruna recognized the same, transfected cells (FIGS. 11b, c). The majority of the immunoreactivity was localized intracellularly and was accessible only after permeabilization.

6.2.7 Mapping the Nogo Active Region(s)

A series of deletion mutants of Nogo was generated in order to map the inhibitory domain(s) or region(s) of Nogo. The deletion constructs of the Nogo gene were generated by using internal restriction sites, exonuclease III-mung bean digestions and polymerase chain reactions. A description of the mutants is provided in FIG. 18 and its Brief Description. The majority of constructs have an N-terminal T7-tag for identification with anti-T7 monoclonal antibodies; and an N- or C-terminal hexahistidine tag ("His-tag") for purification using immobilised-Co(II)-affinity chromatography. The Nogo deletion mutants, named NiG-D1, NiG-D2, up to NiG-D20, were all tested using the NIH 3T3 fibroblast-spreading assay to determine inhibitory activity. Some mutants were tested in PC12 neurite outgrowth, dissociated rat DRG neurite outgrowth or retinal ganglion stripe assays. The results are shown in Table 2 below.

TABLE 2

Functional Activities of Nogo Deletion Mutants

|        | 3T3 | PC12 | DRG | RGC |
|--------|-----|------|-----|-----|
| Nogo-A | ++  |      | +   | +   |
| Nogo-B | +   |      |     |     |
| Nogo-C | −   |      |     | −   |
| NiAext | ++  | +    |     | +   |
| EST    | +/− |      |     |     |
| NiR    | +   |      |     |     |
| NiG    | ++  |      |     | +   |
| NiG-D1 | +   |      |     |     |
| NiG-D2 | +   |      |     |     |
| NiG-D3 | ++  |      |     |     |

TABLE 2-continued

Functional Activities of Nogo Deletion Mutants

| | 3T3 | PC12 | DRG | RGC |
|---|---|---|---|---|
| NiG-D4 | + | | | |
| NiG-D5 | − | | | |
| NiG-D7 | + | | | |
| NiG-D8 | + | | | |
| NiG-D9 | + | | | |
| NiG-D10 | +/− | | | |
| NiG-D14 | − | | | |
| NiG-D15 | + | | | |
| NiG-D16 | + | | | |
| NiG-D17 | + | | | |
| NiG-D18 | + | | | |
| NiG-D20 | ++ | | | |

A positive result in the NIH 3T3 fibroblast assay (3T3) or PC12 assay is scored when fibroblasts or PC12 cells are inhibited from spreading on a plate coated with a preparation of Nogo obtained from a deletion mutant. A positive result in the embryonic chicken dorsal root ganglion neurite outgrowth assay (DRG) or ganglion growth cone collapse assay (RGC) indicates that neurite outgrowth is inhibited or that the growth cone is caused to collapse in the presence of a preparation of Nogo obtained from a deletion mutant.

The data indicate that a major inhibitory domain was identified in the Nogo-A specific region from amino acid numbers 172-974, particularly amino acid numbers 542-722. In addition, the N-terminal sequence of Nogo-A and Nogo-B (amino acid numbers 1-171) was also inhibitory for 3T3 spreading. Based on the results, regions of Nogo from amino acid numbers 172-259, and from numbers 975-1162 appear to be nonessential and can be removed without loss of inhibitory activity.

7. EXAMPLE

Human Nogo Nucleic Acids and Proteins, Derivatives and Fragments

The instant invention provides the nucleotide sequences encoding human Nogo protein, and fragments of human Nogo proteins, including the human equivalents to rat Nogo A, Nogo B and part of Nogo C. The human Nogo amino acid sequence is depicted in FIG. 13 and has been assigned SEQ ID NO:29.

The instant invention also provides nucleotide sequences of fragments of the human Nogo gene. The human Nogo nucleotide sequence can be determined using the rat Nogo A transcript as an aid to align and splice together human expressed sequence tags (EST) that are homologous to the rat or bovine cDNA sequence.

For example, the ESTs AA081783 and AA333267 (Section 5.1) overlap with each other and correspond to rat Nogo A (FIG. 2a; SEQ ID NO:1) nucleic acid positions 765 to 1272. The ESTs AA322592, AA092565, and AA081525 (Section 5.1) also overlap with each other and the overlapping sequences correspond to rat Nogo nucleic acids 1642 to 2131. These two independent sets of overlapping ESTs cannot be aligned to give the human sequence without direct computer comparison to the rat or bovine Nogo nucleotide sequence of the present invention. For the initial computer alignment, ENTREZ Nucleotide QUERY is preferable. Other computer alignment programs are listed in Section 5.1, as alternative examples and are not meant to limit the scope of computer programs that can be used.

8. Discussion

8.1 Cloning of the Neurite Growth Inhibitor Nogo

Nogo A has many properties that support it being the previously described rat NI-250, a major neurite outgrowth inhibitory protein of CNS myelin and the antigen of the IN-1. At the molecular level, Nogo A contains all six peptides originally obtained by sequencing of bNI-220, the most inhibitory component of bovine spinal cord myelin. At the expression level, oligodendrocytes are the major cell type in adult CNS for Nogo A expression, and the timing of Nogo expression in the optic nerve matches the previous description of a IN-1 neutralized myelin inhibitory activity for neurite growth. Moreover, Western blotting revealed the presence of Nogo A in active q-pool fractions, and white matter from various CNS regions was stained with AS Bruna as well as AS 472 (specific for Nogo A) in a pattern identical to that of IN-1. Both of these facts agree with the interpretation that Nogo A is NI-250.

Two antisera raised against Nogo A sequences, AS Bruna and AS 472, greatly decreased the inhibitory activity of a partially purified bovine spinal cord preparation (q-pool). AS 472 also allowed ingrowth of large numbers of dorsal root ganglia axons over several millimeters into adult optic nerve explants, very similar to IN-1.

Although the calculated molecular weight of Nogo A is about 140 kD, it has an apparent molecular weight of about 200 kD on denaturing SDS gels, which is in the range of the previous estimation of about 250 kD. The aberrant mobility of Nogo A in SDS gels is likely caused by its acidic nature rather than post-translational modifications. Aberrant mobility of proteins on SDS-PAGE has been postulated for other highly acidic proteins such as the Growth-Associated Protein GAP-43, as well as NSP-A. Furthermore, bacterially expressed recombinant Nogo A has the same apparent molecular weight as that of the endogenous Nogo A expressed by rat oligodendrocytes. This argues against major modifications of Nogo A by mechanism such as glycosylation.

8.2 Nogo Prevents Regeneration and Restricts Plasticity of the Adult CNS

The expression of Nogo in rat optic nerve oligodendrocytes from P0 on agrees well with the earlier findings of a IN-1 neutralizable neurite growth inhibitory activity. Interestingly, this expression precedes that of the main myelin proteins, and compact myelin formation by several days. The appearance of Nogo, possibly in response to axonal signals, could prevent further axon growth in the corresponding fiber tracts (axon numbers peak at E20 in rat optic nerves). Nogo could also inhibit collateral formation and thereby stabilize the general structure of the differentiated CNS. In grey matter of different CNS regions, the content of myelin and IN-1 immunoreactivity correlates inversely with the level of GAP-43 and the plastic potential of the given regions. Indeed, IN-1 antibodies applied to the adult CNS allow sprouting and plasticity to occur in the brainstem and the spinal cord to an extent known previously only of the new-born CNS. The large functional recovery that parallels this plasticity indicates that sprouting axons are able to form functionally appropriate connections.

It has been demonstrated previously that the response of neurons to inhibitory Nogos differs between neurons of different ages. Presumably, this is due to a differential expression of receptors, which will hopefully soon be characterized. Like for the Netrins and many growth factors the existence of different Nogo receptors, which trigger different responses, remains a possibility. The fact that Nogos are also expressed in some types of neurons points to possible interactions between the same and/or different Nogo isoforms.

8.3 Nogo Belongs to a New Family of Neurite Regulatory Molecules

Sequence analysis of Nogo reveals no known motifs of cell surface or matrix proteins involved in axonal guidance (repulsive or attractive); i.e. no Immunoglobulin, fibronectin type III, or EGF-domains could be identified. Neither was there homology to described neural growth inhibitors, the Semaphorins, the Netrins, or the Ephrins.

Nogos form a novel family with a group of recently described proteins, the NSP/s-rex and the NSP-like 1 proteins, based on the similarity of their carboxy terminal 180 amino acids. Like in the case of Nogo, both alternative promoter usage (both Nsp and Nsp-like 1 gene) and alternative splicing (Nsp only) are responsible for the production of alternative protein products with common carboxy termini containing two stretches of hydrophobic amino acids. As indicated by the name, the NSPs (neuroendocrine-specific proteins) are predominantly expressed in neurons and several endocrine cell types. They localize mainly intracellularly in association with the endoplasmic reticulum. The NSP-like 1 gene is expressed predominantly in brain and muscle. The functions of neither the NSP nor the Nsp-like 1 families are known. The fact that potential orthologs exist in both *C. elegans* and *Drosophila melanogaster* suggests that Nogo, with its nerve regeneration and sprouting inhibitory activity, may be a newly evolved and heretofore undescribed member of the NSP family.

8.4 Nogo in Non-neuronal Tissues

The Nogo C transcript is expressed in skeletal muscle at a level comparable to that of the nervous system. One conceivable function of muscle Nogo C is to repel motor axons and to restrict them to the motor endplate region. Low levels of Nogo expression can also be detected in other non-nervous tissues. The observed inhibition of fibroblast and astrocyte spreading by myelin extract and NI-250 alludes to the presence of receptors and response mechanisms for Nogo proteins in these cells. This suggests a possible general function of Nogos in contact inhibition of cell movement.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A method of immunizing a non-human animal in order to generate antibodies against a Nogo protein, said method comprising administering to said animal an immunogenic amount of a protein consisting of:
   (i) the carboxy terminal 188 amino acids of SEQ ID NO:29;
   (ii) an amino acid sequence consisting of amino acids 988-1023 of SEQ ID NO:2;
   (iii) an amino acid sequence consisting of amino acids 975-1162 of SEQ ID NO:2;
   (iv) an amino acid sequence consisting of amino acids 172 to 974 of SEQ ID NO:2;
   (v) an amino acid sequence consisting of amino acids 172 to 723 of SEQ ID NO:2;
   (vi) an amino acid sequence consisting of amino acids 542 to 722 of SEQ ID NO:2;
   (vii) an amino acid sequence consisting of amino acids 1-171 of SEQ ID NO:2;
   (viii) an amino acid sequence consisting of amino acids 1-974 of SEQ ID NO:2;
   (ix) an amino acid sequence consisting of amino acids 1-131 of SEQ ID NO:2;
   (x) an amino acid sequence consisting of amino acids 680-939 of SEQ ID NO:29;
   (xi) an amino acid sequence consisting of amino acids 940-1127 of SEQ ID NO:29;
   (xii) an amino acid sequence consisting of amino acids 259-542 of SEQ ID NO:2;
   (xiii) an amino acid sequence consisting of amino acids 172-259 of SEQ ID NO:2;
   (xiv) an amino acid sequence consisting of amino acids 722-974 of SEQ ID NO:2.

2. A method of immunizing a non-human animal, said method comprising administering to said animal an immunogenic amount of a protein consisting of:
   (i) a first amino acid sequence in which more than 95% of the amino acid residues in said first sequence are identical to the amino acid residues of a second amino acid sequence in an alignment, said second amino acid sequence consisting of the amino acid sequence of amino acids 1-131 of SEQ ID NO:29,
   (ii) a first amino acid sequence in which more than 95% of the amino acid residues in said first sequence are identical to the amino acid residues of a second amino acid sequence in an alignment, said second amino acid sequence consisting of the amino acid sequence of amino acids 132-939 of SEQ ID NO:29,
   (iii) a first amino acid sequence in which more than 95% of the amino acid residues in said first sequence are identical to the amino acid residues of a second amino acid sequence in an alignment, said second amino acid sequence consisting of the amino acid sequence of amino acids 206-501 of SEQ ID NO:29,
   (iv) a first amino acid sequence in which more than 95% of the amino acid residues in said first sequence are identical to the amino acid residues of a second amino acid sequence in an alignment, said second amino acid sequence consisting of the amino acid sequence of amino acids 501-680 of SEQ ID NO:29,
   (v) a first amino acid sequence in which more than 95% of the amino acid residues in said first sequence are identical to the amino acid residues of a second amino acid sequence in an alignment, said second amino acid sequence consisting of the amino acid sequence of amino acids 132-206 of SEQ ID NO:29,
   (vi) a first amino acid sequence in which more than 95% of the amino acid residues in said first sequence are identical to the amino acid residues of a second amino acid sequence in an alignment, said second amino acid sequence consisting of the amino acid sequence of amino acids 680-939 of SEQ ID NO:29, or
   (vii) a first amino acid sequence in which more than 95% of the amino acid residues in said first sequence are identical to the amino acid residues of a second amino acid sequence in an alignment, said second amino acid sequence consisting of the amino acid sequence of amino acids 940-1127 of SEQ ID NO:29, and wherein said protein is free of all central nervous system myelin material, wherein said protein has one or more Nogo functional activities selected from the group consisting of:
   (i) ability to prevent regeneration of neurons in the spinal cord or brain;
   (ii) ability to confer to a substrate the property of restricting growth, spreading, and migration of neural cells;
   (iii) ability to inhibit dorsal root ganglia neurite outgrowth;
   (iv) ability to block NIH 3T3 cell spreading in vitro; and
   (v) ability to block PC12 neurite outgrowth.

3. A method of obtaining polyclonal antibodies to a protein, wherein said protein consists of:
  (i) a first amino acid sequence in which more than 95% of the amino acid residues in said first amino acid sequence are identical to the amino acid residues of a second amino acid sequence in an alignment, said second amino acid sequence consisting of the amino acid sequence of amino acids 1-131 of SEQ ID NO:29,
  (ii) a first amino acid sequence in which more than 95% of the amino acid residues in said first amino acid sequence are identical to the amino acid residues of a second amino acid sequence in an alignment, said second amino acid sequence consisting of the amino acid sequence of amino acids 132-939 of SEQ ID NO:29,
  (iii) a first amino acid sequence in which more than 95% of the amino acid residues in said first amino acid sequence are identical to the amino acid residues of a second amino acid sequence in an alignment, said second amino acid sequence consisting of the amino acid sequence of amino acids 206-501 of SEQ ID NO:29,
  (iv) a first amino acid sequence in which more than 95% of the amino acid residues in said first amino acid sequence are identical to the amino acid residues of a second amino acid sequence in an alignment, said second amino acid sequence consisting of the amino acid sequence of amino acids 501-680 of SEQ ID NO:29,
  (v) a first amino acid sequence in which more than 95% of the amino acid residues in said first amino acid sequence are identical to the amino acid residues of a second amino acid sequence in an alignment, said second amino acid sequence consisting of the amino acid sequence of amino acids 132-206 of SEQ ID NO:29,
  (vi) a first amino acid sequence in which more than 95% of the amino acid residues in said first amino acid sequence are identical to the amino acid residues of a second amino acid sequence in an alignment, said second amino acid sequence consisting of the amino acid sequence of amino acids 680-939 of SEQ ID NO:29, or
  (vii) a first amino acid sequence in which more than 95% of the amino acid residues in said first amino acid sequence are identical to the amino acid residues of a second amino acid sequence in an alignment, said second amino acid sequence consisting of the amino acid sequence of amino acids 940-1127 of SEQ ID NO:29,
  and wherein the protein has one or more Nogo functional activities selected from the group consisting of:
  (i) ability to prevent regeneration of neurons in the spinal cord or brain;
  (ii) ability to confer to a substrate the property of restricting growth, spreading, and migration of neural cells;
  (iii) ability to inhibit dorsal root ganglia neurite outgrowth;
  (iv) ability to block NIH 3T3 cell spreading in vitro; and
  (v) ability to block PC12 neurite outgrowth;
  and wherein said method comprises:
    (a) immunizing an animal with said protein that is free of all central nervous system myelin material; and,
    (b) recovering polyclonal antibodies from the animal.

4. The method of any one of claims 1, 2 and 3, wherein the animal is a mouse.

5. The method of any one of claims 1, 2 and 3, wherein said protein is recombinant.

6. The method of any one of claims 1, 2 and 3, wherein said protein is mammalian.

7. The method of any one of claims 1, 2 and 3, wherein said protein is human.

* * * * *

```
                        SEQUENCE LISTING

<160> NUMBER OF SEQ ID NOS: 51

<210> SEQ ID NO 1
<211> LENGTH: 3741
<212> TYPE: DNA
<213> ORGANISM: Rattus sp.
<220> FEATURE:
<221> NAME/KEY: CDS
<222> LOCATION: (253)...(3741)

<400> SEQUENCE: 1
attgctcgtc tgggcggcgg cggcggctgc agcctgggac agggcgggtg gcacatctcg      60
atcgcgaagg cagcagaagc agtctcattg ttccgggagc cgtcgcctct gcaggttctt     120
cggctcggct cggcacgact cggcctgcct ggcccctgcc agtcttgccc aaccccaca      180 accgcccgcg actctgagga gaagcggccc tgcggcggct gtagctgcag catcgtcggc     240
gacccgccag cc atg gaa gac ata gac cag tcg tcg ctg gtc tcc tcg tcc     291
              Met Glu Asp Ile Asp Gln Ser Ser Leu Val Ser Ser Ser
                1               5                   10 acg gac agc ccg ccc cgg cct ccg ccc gcc ttc aag tac cag ttc gtg      339
Thr Asp Ser Pro Pro Arg Pro Pro Pro Ala Phe Lys Tyr Gln Phe Val
         15                  20                  25 acg gag ccc gag gac gag gag gac gag gag gag gag gag gac gag gag      387
Thr Glu Pro Glu Asp Glu Glu Asp Glu Glu Glu Glu Glu Asp Glu Glu
    30                  35                  40                  45 gag gac gac gag gac cta gag gaa ctg gag gtg ctg gag agg aag ccc      435
Glu Asp Asp Glu Asp Leu Glu Glu Leu Glu Val Leu Glu Arg Lys Pro
                 50                  55                  60 gca gcc ggg ctg tcc gca gct gcg gtg ccg ccc gcc gcc gcg ccg          483
Ala Ala Gly Leu Ser Ala Ala Ala Val Pro Pro Ala Ala Ala Ala Pro
             65                  70                  75
```

```
ctg ctg gac ttc agc agc gac tcg gtg ccc ccc gcg ccc cgc ggg ccg    531
Leu Leu Asp Phe Ser Ser Asp Ser Val Pro Pro Ala Pro Arg Gly Pro
        80                  85                  90 ctg ccg gcc gcg ccc cct gcc gct cct gag agg cag cca tcc tgg gaa    579
Leu Pro Ala Ala Pro Pro Ala Ala Pro Glu Arg Gln Pro Ser Trp Glu
    95                 100                 105 cgc agc ccc gcg gcg ccc gcg cca tcc ctg ccg ccc gct gcc gca gtc    627
Arg Ser Pro Ala Ala Pro Ala Pro Ser Leu Pro Pro Ala Ala Ala Val
110                 115                 120                 125 ctg ccc tcc aag ctc cca gag gac gac gag cct ccg gcg agg ccc ccg    675
Leu Pro Ser Lys Leu Pro Glu Asp Asp Glu Pro Pro Ala Arg Pro Pro
                130                 135                 140 cct ccg ccg cca gcc ggc gcg agc ccc ctg gcg gag ccc gcc gcg ccc    723
Pro Pro Pro Pro Ala Gly Ala Ser Pro Leu Ala Glu Pro Ala Ala Pro
            145                 150                 155 cct tcc acg ccg gcc gcg ccc aag cgc agg ggc tcc ggc tca gtg gat    771
Pro Ser Thr Pro Ala Ala Pro Lys Arg Arg Gly Ser Gly Ser Val Asp
        160                 165                 170 gag acc ctt ttt gct ctt cct gct gca tct gag cct gtg ata ccc tcc    819
Glu Thr Leu Phe Ala Leu Pro Ala Ala Ser Glu Pro Val Ile Pro Ser
    175                 180                 185 tct gca gaa aaa att atg gat ttg atg gag cag cca ggt aac act gtt    867
Ser Ala Glu Lys Ile Met Asp Leu Met Glu Gln Pro Gly Asn Thr Val
190                 195                 200                 205 tcg tct ggt caa gag gat ttc cca tct gtc ctg ctt gaa act gct gcc    915
Ser Ser Gly Gln Glu Asp Phe Pro Ser Val Leu Leu Glu Thr Ala Ala
                210                 215                 220 tct ctt cct tct cta tct cct ctc tca act gtt tct ttt aaa gaa cat    963
Ser Leu Pro Ser Leu Ser Pro Leu Ser Thr Val Ser Phe Lys Glu His
            225                 230                 235 gga tac ctt ggt aac tta tca gca gtg tca tcc tca gaa gga aca att   1011
Gly Tyr Leu Gly Asn Leu Ser Ala Val Ser Ser Ser Glu Gly Thr Ile
        240                 245                 250 gaa gaa act tta aat gaa gct tct aaa gag ttg cca gag agg gca aca   1059
Glu Glu Thr Leu Asn Glu Ala Ser Lys Glu Leu Pro Glu Arg Ala Thr
    255                 260                 265 aat cca ttt gta aat aga gat tta gca gaa ttt tca gaa tta gaa tat   1107
Asn Pro Phe Val Asn Arg Asp Leu Ala Glu Phe Ser Glu Leu Glu Tyr
270                 275                 280                 285 tca gaa atg gga tca tct ttt aaa ggc tcc cca aaa gga gag tca gcc   1155
Ser Glu Met Gly Ser Ser Phe Lys Gly Ser Pro Lys Gly Glu Ser Ala
                290                 295                 300 ata tta gta gaa aac act aag gaa gaa gta att gtg agg agt aaa gac   1203
Ile Leu Val Glu Asn Thr Lys Glu Glu Val Ile Val Arg Ser Lys Asp
            305                 310                 315 aaa gag gat tta gtt tgt agt gca gcc ctt cac agt cca caa gaa tca   1251
Lys Glu Asp Leu Val Cys Ser Ala Ala Leu His Ser Pro Gln Glu Ser
        320                 325                 330 cct gtg ggt aaa gaa gac aga gtt gtg tct cca gaa aag aca atg gac   1299
Pro Val Gly Lys Glu Asp Arg Val Val Ser Pro Glu Lys Thr Met Asp
    335                 340                 345 att ttt aat gaa atg cag atg tca gta gta gca cct gtg agg gaa gag   1347
Ile Phe Asn Glu Met Gln Met Ser Val Val Ala Pro Val Arg Glu Glu
350                 355                 360                 365 tat gca gac ttt aag cca ttt gaa caa gca tgg gaa gtg aaa gat act   1395
Tyr Ala Asp Phe Lys Pro Phe Glu Gln Ala Trp Glu Val Lys Asp Thr
                370                 375                 380 tat gag gga agt agg gat gtg ctg gct gct aga gct aat gtg gaa agt   1443
Tyr Glu Gly Ser Arg Asp Val Leu Ala Ala Arg Ala Asn Val Glu Ser
            385                 390                 395
```

-continued

| | | |
|---|---|---|
| aaa gtg gac aga aaa tgc ttg gaa gat agc ctg gag caa aaa agt ctt | 1491 | |
| Lys Val Asp Arg Lys Cys Leu Glu Asp Ser Leu Glu Gln Lys Ser Leu | | |
| 400 405 410 | | |
| ggg aag gat agt gaa ggc aga aat gag gat gct tct ttc ccc agt acc | 1539 | |
| Gly Lys Asp Ser Glu Gly Arg Asn Glu Asp Ala Ser Phe Pro Ser Thr | | |
| 415 420 425 | | |
| cca gaa cct gtg aag gac agc tcc aga gca tat att acc tgt gct tcc | 1587 | |
| Pro Glu Pro Val Lys Asp Ser Ser Arg Ala Tyr Ile Thr Cys Ala Ser | | |
| 430 435 440 445 | | |
| ttt acc tca gca acc gaa agc acc aca gca aac act ttc cct ttg tta | 1635 | |
| Phe Thr Ser Ala Thr Glu Ser Thr Thr Ala Asn Thr Phe Pro Leu Leu | | |
| 450 455 460 | | |
| gaa gat cat act tca gaa aat aaa aca gat gaa aaa aaa ata gaa gaa | 1683 | |
| Glu Asp His Thr Ser Glu Asn Lys Thr Asp Glu Lys Lys Ile Glu Glu | | |
| 465 470 475 | | |
| agg aag gcc caa att ata aca gag aag act agc ccc aaa acg tca aat | 1731 | |
| Arg Lys Ala Gln Ile Ile Thr Glu Lys Thr Ser Pro Lys Thr Ser Asn | | |
| 480 485 490 | | |
| cct ttc ctt gta gca gta cag gat tct gag gca gat tat gtt aca aca | 1779 | |
| Pro Phe Leu Val Ala Val Gln Asp Ser Glu Ala Asp Tyr Val Thr Thr | | |
| 495 500 505 | | |
| gat acc tta tca aag gtg act gag gca gca gtg tca aac atg cct gaa | 1827 | |
| Asp Thr Leu Ser Lys Val Thr Glu Ala Ala Val Ser Asn Met Pro Glu | | |
| 510 515 520 525 | | |
| ggt ctg acg cca gat tta gtt cag gaa gca tgt gaa agt gaa ctg aat | 1875 | |
| Gly Leu Thr Pro Asp Leu Val Gln Glu Ala Cys Glu Ser Glu Leu Asn | | |
| 530 535 540 | | |
| gaa gcc aca ggt aca aag att gct tat gaa aca aag gtg gac ttg gtc | 1923 | |
| Glu Ala Thr Gly Thr Lys Ile Ala Tyr Glu Thr Lys Val Asp Leu Val | | |
| 545 550 555 | | |
| caa aca tca gaa gct ata caa gaa tca ctt tac ccc aca gca cag ctt | 1971 | |
| Gln Thr Ser Glu Ala Ile Gln Glu Ser Leu Tyr Pro Thr Ala Gln Leu | | |
| 560 565 570 | | |
| tgc cca tca ttt gag gaa gct gaa gca act ccg tca cca gtt ttg cct | 2019 | |
| Cys Pro Ser Phe Glu Glu Ala Glu Ala Thr Pro Ser Pro Val Leu Pro | | |
| 575 580 585 | | |
| gat att gtt atg gaa gca cca tta aat tct ctc ctt cca agc gct ggt | 2067 | |
| Asp Ile Val Met Glu Ala Pro Leu Asn Ser Leu Leu Pro Ser Ala Gly | | |
| 590 595 600 605 | | |
| gct tct gta gtg cag ccc agt gta tcc cca ctg gaa gca cct cct cca | 2115 | |
| Ala Ser Val Val Gln Pro Ser Val Ser Pro Leu Glu Ala Pro Pro Pro | | |
| 610 615 620 | | |
| gtt agt tat gac agt ata aag ctt gag cct gaa aac ccc cca cca tat | 2163 | |
| Val Ser Tyr Asp Ser Ile Lys Leu Glu Pro Glu Asn Pro Pro Pro Tyr | | |
| 625 630 635 | | |
| gaa gaa gcc atg aat gta gca cta aaa gct ttg gga aca aag gaa gga | 2211 | |
| Glu Glu Ala Met Asn Val Ala Leu Lys Ala Leu Gly Thr Lys Glu Gly | | |
| 640 645 650 | | |
| ata aaa gag cct gaa agt ttt aat gca gct gtt cag gaa aca gaa gct | 2259 | |
| Ile Lys Glu Pro Glu Ser Phe Asn Ala Ala Val Gln Glu Thr Glu Ala | | |
| 655 660 665 | | |
| cct tat ata tcc att gcg tgt gat tta att aaa gaa aca aag ctc tcc | 2307 | |
| Pro Tyr Ile Ser Ile Ala Cys Asp Leu Ile Lys Glu Thr Lys Leu Ser | | |
| 670 675 680 685 | | |
| act gag cca gtc cca gat ttc tct aat tat tca gaa ata gca aaa ttc | 2355 | |
| Thr Glu Pro Ser Pro Asp Phe Ser Asn Tyr Ser Glu Ile Ala Lys Phe | | |
| 690 695 700 | | |
| gag aag tcg gtg ccc gaa cac gct gag cta gtg gag gat tcc tca cct | 2403 | |
| Glu Lys Ser Val Pro Glu His Ala Glu Leu Val Glu Asp Ser Ser Pro | | |
| 705 710 715 | | |

```
gaa tct gaa cca gtt gac tta ttt agt gat gat tcg att cct gaa gtc    2451
Glu Ser Glu Pro Val Asp Leu Phe Ser Asp Asp Ser Ile Pro Glu Val
        720                 725                 730 cca caa aca caa gag gag gct gtg atg ctc atg aag gag agt ctc act    2499
Pro Gln Thr Gln Glu Glu Ala Val Met Leu Met Lys Glu Ser Leu Thr
735                 740                 745 gaa gtg tct gag aca gta gcc cag cac aaa gag gag aga ctt agt gcc    2547
Glu Val Ser Glu Thr Val Ala Gln His Lys Glu Glu Arg Leu Ser Ala
750                 755                 760                 765 tca cct cag gag cta gga aag cca tat tta gag tct ttt cag ccc aat    2595
Ser Pro Gln Glu Leu Gly Lys Pro Tyr Leu Glu Ser Phe Gln Pro Asn
        770                 775                 780 tta cat agt aca aaa gat gct gca tct aat gac att cca aca ttg acc    2643
Leu His Ser Thr Lys Asp Ala Ala Ser Asn Asp Ile Pro Thr Leu Thr
    785                 790                 795 aaa aag gag aaa att tct ttg caa atg gaa gag ttt aat act gca att    2691
Lys Lys Glu Lys Ile Ser Leu Gln Met Glu Glu Phe Asn Thr Ala Ile
800                 805                 810 tat tca aat gat gac tta ctt tct tct aag gaa gac aaa ata aaa gaa    2739
Tyr Ser Asn Asp Asp Leu Leu Ser Ser Lys Glu Asp Lys Ile Lys Glu
        815                 820                 825 agt gaa aca ttt tca gat tca tct ccg att gag ata ata gat gaa ttt    2787
Ser Glu Thr Phe Ser Asp Ser Ser Pro Ile Glu Ile Ile Asp Glu Phe
830                 835                 840                 845 ccc acg ttt gtc agt gct aaa gat gat tct cct aaa tta gcc aag gag    2835
Pro Thr Phe Val Ser Ala Lys Asp Asp Ser Pro Lys Leu Ala Lys Glu
            850                 855                 860 tac act gat cta gaa gta tcc gac aaa agt gaa att gct aat atc caa    2883
Tyr Thr Asp Leu Glu Val Ser Asp Lys Ser Glu Ile Ala Asn Ile Gln
        865                 870                 875 agc ggg gca gat tca ttg cct tgc tta gaa ttg ccc tgt gac ctt tct    2931
Ser Gly Ala Asp Ser Leu Pro Cys Leu Glu Leu Pro Cys Asp Leu Ser
    880                 885                 890 ttc aag aat ata tat cct aaa gat gaa gta cat gtt tca gat gaa ttc    2979
Phe Lys Asn Ile Tyr Pro Lys Asp Glu Val His Val Ser Asp Glu Phe
895                 900                 905 tcc gaa aat agg tcc agt gta tct aag gca tcc ata tcg cct tca aat    3027
Ser Glu Asn Arg Ser Ser Val Ser Lys Ala Ser Ile Ser Pro Ser Asn
910                 915                 920                 925 gtc tct gct ttg gaa cct cag aca gaa atg ggc agc ata gtt aaa tcc    3075
Val Ser Ala Leu Glu Pro Gln Thr Glu Met Gly Ser Ile Val Lys Ser
            930                 935                 940 aaa tca ctt acg aaa gaa gca gag aaa aaa ctt cct tct gac aca gag    3123
Lys Ser Leu Thr Lys Glu Ala Glu Lys Lys Leu Pro Ser Asp Thr Glu
        945                 950                 955 aaa gag gac aga tcc ctg tca gct gta ttg tca gca gag ctg agt aaa    3171
Lys Glu Asp Arg Ser Leu Ser Ala Val Leu Ser Ala Glu Leu Ser Lys
    960                 965                 970 act tca gtt gtt gac ctc ctc tac tgg aga gac att aag aag act gga    3219
Thr Ser Val Val Asp Leu Leu Tyr Trp Arg Asp Ile Lys Lys Thr Gly
975                 980                 985 gtg gtg ttt ggt gcc agc tta ttc ctg ctg tct ctg aca gtg ttc        3267
Val Val Phe Gly Ala Ser Leu Phe Leu Leu Ser Leu Thr Val Phe
990                 995                 1000                1005 agc att gtc agt gta acg gcc tac att gcc ttg gcc ctg ctc tcg gtg    3315
Ser Ile Val Ser Val Thr Ala Tyr Ile Ala Leu Ala Leu Leu Ser Val
            1010                1015                1020 act atc agc ttt agg ata tat aag ggc gtg atc cag gct atc cag aaa    3363
Thr Ile Ser Phe Arg Ile Tyr Lys Gly Val Ile Gln Ala Ile Gln Lys
        1025                1030                1035
```

```
tca gat gaa ggc cac cca ttc agg gca tat tta gaa tct gaa gtt gct    3411
Ser Asp Glu Gly His Pro Phe Arg Ala Tyr Leu Glu Ser Glu Val Ala
        1040                1045                1050 ata tca gag gaa ttg gtt cag aaa tac agt aat tct gct ctt ggt cat    3459
Ile Ser Glu Glu Leu Val Gln Lys Tyr Ser Asn Ser Ala Leu Gly His
    1055                1060                1065 gtg aac agc aca ata aaa gaa ctg agg cgg ctt ttc tta gtt gat gat    3507
Val Asn Ser Thr Ile Lys Glu Leu Arg Arg Leu Phe Leu Val Asp Asp
1070                1075                1080                1085 tta gtt gat tcc ctg aag ttt gca gtg ttg atg tgg gtg ttt act tat    3555
Leu Val Asp Ser Leu Lys Phe Ala Val Leu Met Trp Val Phe Thr Tyr
                1090                1095                1100 gtt ggt gcc ttg ttc aat ggt ctg aca cta ctg att tta gct ctg atc    3603
Val Gly Ala Leu Phe Asn Gly Leu Thr Leu Leu Ile Leu Ala Leu Ile
            1105                1110                1115 tca ctc ttc agt att cct gtt att tat gaa cgg cat cag gtg cag ata    3651
Ser Leu Phe Ser Ile Pro Val Ile Tyr Glu Arg His Gln Val Gln Ile
        1120                1125                1130 gat cat tat cta gga ctt gca aac aag agt gtt aag gat gcc atg gcc    3699
Asp His Tyr Leu Gly Leu Ala Asn Lys Ser Val Lys Asp Ala Met Ala
    1135                1140                1145 aaa atc caa gca aaa atc cct gga ttg aag cgc aaa gca gat            3741
Lys Ile Gln Ala Lys Ile Pro Gly Leu Lys Arg Lys Ala Asp
1150                1155                1160

<210> SEQ ID NO 2
<211> LENGTH: 1163
<212> TYPE: PRT
<213> ORGANISM: Rattus sp.

<400> SEQUENCE: 2

Met Glu Asp Ile Asp Gln Ser Ser Leu Val Ser Ser Ser Thr Asp Ser
1               5                   10                  15

Pro Pro Arg Pro Pro Pro Ala Phe Lys Tyr Gln Phe Val Thr Glu Pro
            20                  25                  30

Glu Asp Glu Glu Asp Glu Glu Glu Glu Asp Glu Glu Glu Asp Asp
        35                  40                  45

Glu Asp Leu Glu Glu Leu Glu Val Leu Glu Arg Lys Pro Ala Ala Gly
    50                  55                  60

Leu Ser Ala Ala Ala Val Pro Pro Ala Ala Ala Pro Leu Leu Asp
65                  70                  75                  80

Phe Ser Ser Asp Ser Val Pro Ala Pro Arg Gly Pro Leu Pro Ala
                85                  90                  95

Ala Pro Pro Ala Ala Pro Glu Arg Gln Pro Ser Trp Glu Arg Ser Pro
            100                 105                 110

Ala Ala Pro Ala Pro Ser Leu Pro Ala Ala Val Leu Pro Ser
        115                 120                 125

Lys Leu Pro Glu Asp Asp Glu Pro Pro Ala Arg Pro Pro Pro Pro
    130                 135                 140

Pro Ala Gly Ala Ser Pro Leu Ala Glu Pro Ala Ala Pro Ser Thr
145                 150                 155                 160

Pro Ala Ala Pro Lys Arg Arg Gly Ser Gly Ser Val Asp Glu Thr Leu
                165                 170                 175

Phe Ala Leu Pro Ala Ala Ser Glu Pro Val Ile Pro Ser Ser Ala Glu
            180                 185                 190

Lys Ile Met Asp Leu Met Glu Gln Pro Gly Asn Thr Val Ser Ser Gly
        195                 200                 205
```

-continued

```
Gln Glu Asp Phe Pro Ser Val Leu Leu Glu Thr Ala Ala Ser Leu Pro
210                 215                 220

Ser Leu Ser Pro Leu Ser Thr Val Ser Phe Lys Glu His Gly Tyr Leu
225                 230                 235                 240

Gly Asn Leu Ser Ala Val Ser Ser Glu Gly Thr Ile Glu Glu Thr
                245                 250                 255

Leu Asn Glu Ala Ser Lys Glu Leu Pro Glu Arg Ala Thr Asn Pro Phe
                260                 265                 270

Val Asn Arg Asp Leu Ala Glu Phe Ser Glu Leu Glu Tyr Ser Glu Met
            275                 280                 285

Gly Ser Ser Phe Lys Gly Ser Pro Lys Gly Glu Ser Ala Ile Leu Val
290                 295                 300

Glu Asn Thr Lys Glu Glu Val Ile Val Arg Ser Lys Asp Lys Glu Asp
305                 310                 315                 320

Leu Val Cys Ser Ala Ala Leu His Ser Pro Gln Glu Ser Pro Val Gly
                325                 330                 335

Lys Glu Asp Arg Val Val Ser Pro Glu Lys Thr Met Asp Ile Phe Asn
                340                 345                 350

Glu Met Gln Met Ser Val Val Ala Pro Val Arg Glu Glu Tyr Ala Asp
                355                 360                 365

Phe Lys Pro Phe Glu Gln Ala Trp Glu Val Lys Asp Thr Tyr Glu Gly
370                 375                 380

Ser Arg Asp Val Leu Ala Ala Arg Ala Asn Val Glu Ser Lys Val Asp
385                 390                 395                 400

Arg Lys Cys Leu Glu Asp Ser Leu Glu Gln Lys Ser Leu Gly Lys Asp
                405                 410                 415

Ser Glu Gly Arg Asn Glu Asp Ala Ser Phe Pro Ser Thr Pro Glu Pro
                420                 425                 430

Val Lys Asp Ser Ser Arg Ala Tyr Ile Thr Cys Ala Ser Phe Thr Ser
                435                 440                 445

Ala Thr Glu Ser Thr Thr Ala Asn Thr Phe Pro Leu Leu Glu Asp His
                450                 455                 460

Thr Ser Glu Asn Lys Thr Asp Glu Lys Lys Ile Glu Glu Arg Lys Ala
465                 470                 475                 480

Gln Ile Ile Thr Glu Lys Thr Ser Pro Lys Thr Ser Asn Pro Phe Leu
                485                 490                 495

Val Ala Val Gln Asp Ser Glu Ala Asp Tyr Val Thr Thr Asp Thr Leu
                500                 505                 510

Ser Lys Val Thr Glu Ala Ala Val Ser Asn Met Pro Glu Gly Leu Thr
                515                 520                 525

Pro Asp Leu Val Gln Glu Ala Cys Glu Ser Glu Leu Asn Glu Ala Thr
                530                 535                 540

Gly Thr Lys Ile Ala Tyr Glu Thr Lys Val Asp Leu Val Gln Thr Ser
545                 550                 555                 560

Glu Ala Ile Gln Glu Ser Leu Tyr Pro Thr Ala Gln Leu Cys Pro Ser
                565                 570                 575

Phe Glu Glu Ala Glu Ala Thr Pro Ser Pro Val Leu Pro Asp Ile Val
                580                 585                 590

Met Glu Ala Pro Leu Asn Ser Leu Leu Pro Ser Ala Gly Ala Ser Val
                595                 600                 605

Val Gln Pro Ser Val Ser Pro Leu Glu Ala Pro Pro Val Ser Tyr
610                 615                 620
```

-continued

```
Asp Ser Ile Lys Leu Glu Pro Glu Asn Pro Pro Tyr Glu Glu Ala
625                 630                 635                 640

Met Asn Val Ala Leu Lys Ala Leu Gly Thr Lys Glu Gly Ile Lys Glu
            645                 650                 655

Pro Glu Ser Phe Asn Ala Ala Val Gln Glu Thr Glu Ala Pro Tyr Ile
                660                 665                 670

Ser Ile Ala Cys Asp Leu Ile Lys Glu Thr Lys Leu Ser Thr Glu Pro
            675                 680                 685

Ser Pro Asp Phe Ser Asn Tyr Ser Glu Ile Ala Lys Phe Glu Lys Ser
        690                 695                 700

Val Pro Glu His Ala Glu Leu Val Glu Asp Ser Ser Pro Glu Ser Glu
705                 710                 715                 720

Pro Val Asp Leu Phe Ser Asp Asp Ser Ile Pro Glu Val Pro Gln Thr
                725                 730                 735

Gln Glu Glu Ala Val Met Leu Met Lys Glu Ser Leu Thr Glu Val Ser
            740                 745                 750

Glu Thr Val Ala Gln His Lys Glu Glu Arg Leu Ser Ala Ser Pro Gln
        755                 760                 765

Glu Leu Gly Lys Pro Tyr Leu Glu Ser Phe Gln Pro Asn Leu His Ser
770                 775                 780

Thr Lys Asp Ala Ala Ser Asn Asp Ile Pro Thr Leu Thr Lys Lys Glu
785                 790                 795                 800

Lys Ile Ser Leu Gln Met Glu Glu Phe Asn Thr Ala Ile Tyr Ser Asn
                805                 810                 815

Asp Asp Leu Leu Ser Ser Lys Glu Asp Lys Ile Lys Glu Ser Glu Thr
            820                 825                 830

Phe Ser Asp Ser Ser Pro Ile Glu Ile Asp Glu Phe Pro Thr Phe
        835                 840                 845

Val Ser Ala Lys Asp Asp Ser Pro Lys Leu Ala Lys Glu Tyr Thr Asp
        850                 855                 860

Leu Glu Val Ser Asp Lys Ser Glu Ile Ala Asn Ile Gln Ser Gly Ala
865                 870                 875                 880

Asp Ser Leu Pro Cys Leu Glu Leu Pro Cys Asp Leu Ser Phe Lys Asn
                885                 890                 895

Ile Tyr Pro Lys Asp Glu Val His Val Ser Asp Glu Phe Ser Glu Asn
            900                 905                 910

Arg Ser Ser Val Ser Lys Ala Ser Ile Ser Pro Ser Asn Val Ser Ala
        915                 920                 925

Leu Glu Pro Gln Thr Glu Met Gly Ser Ile Val Lys Ser Lys Ser Leu
    930                 935                 940

Thr Lys Glu Ala Glu Lys Lys Leu Pro Ser Asp Thr Glu Lys Glu Asp
945                 950                 955                 960

Arg Ser Leu Ser Ala Val Leu Ser Ala Glu Leu Ser Lys Thr Ser Val
                965                 970                 975

Val Asp Leu Leu Tyr Trp Arg Asp Ile Lys Lys Thr Gly Val Val Phe
            980                 985                 990

Gly Ala Ser Leu Phe Leu Leu Leu Ser Leu Thr Val Phe Ser Ile Val
        995                 1000                1005

Ser Val Thr Ala Tyr Ile Ala Leu Ala Leu Leu Ser Val Thr Ile Ser
    1010                1015                1020

Phe Arg Ile Tyr Lys Gly Val Ile Gln Ala Ile Gln Lys Ser Asp Glu
1025                1030                1035                1040
```

```
Gly His Pro Phe Arg Ala Tyr Leu Glu Ser Glu Val Ala Ile Ser Glu
            1045                1050                1055

Glu Leu Val Gln Lys Tyr Ser Asn Ser Ala Leu Gly His Val Asn Ser
            1060                1065            1070

Thr Ile Lys Glu Leu Arg Arg Leu Phe Leu Val Asp Asp Leu Val Asp
        1075                1080                1085

Ser Leu Lys Phe Ala Val Leu Met Trp Val Phe Thr Tyr Val Gly Ala
        1090                1095                1100

Leu Phe Asn Gly Leu Thr Leu Ile Leu Ala Leu Ile Ser Leu Phe
1105                1110                1115                1120

Ser Ile Pro Val Ile Tyr Glu Arg His Gln Val Gln Ile Asp His Tyr
            1125                1130                1135

Leu Gly Leu Ala Asn Lys Ser Val Lys Asp Ala Met Ala Lys Ile Gln
            1140                1145                1150

Ala Lys Ile Pro Gly Leu Lys Arg Lys Ala Asp
        1155                1160

<210> SEQ ID NO 3
<211> LENGTH: 13
<212> TYPE: PRT
<213> ORGANISM: Bos sp.

<400> SEQUENCE: 3

Glu Tyr Leu Gly Asp Leu Pro Ala Val Leu Pro Thr Glu
1               5                   10

<210> SEQ ID NO 4
<211> LENGTH: 11
<212> TYPE: PRT
<213> ORGANISM: Bos sp.

<400> SEQUENCE: 4

Glu Ile Ala Glu Ile Gln Asp Gly Glu Ser Leu
1               5                   10

<210> SEQ ID NO 5
<211> LENGTH: 15
<212> TYPE: PRT
<213> ORGANISM: Bos sp.
<220> FEATURE:
<221> NAME/KEY: VARIANT
<222> LOCATION: (2)...(2)
<223> OTHER INFORMATION: Xaa = any amino acid

<400> SEQUENCE: 5

Lys Xaa Tyr Leu Glu Ser Ile Gln Pro Ser Leu Gly Ile Thr Lys
1               5                   10                  15

<210> SEQ ID NO 6
<211> LENGTH: 9
<212> TYPE: PRT
<213> ORGANISM: Bos sp.
<220> FEATURE:
<221> NAME/KEY: VARIANT
<222> LOCATION: 2,5
<223> OTHER INFORMATION: Xaa = any amino acid

<400> SEQUENCE: 6

Lys Xaa Phe Glu Xaa Val Trp Glu Val
1               5
```

```
<210> SEQ ID NO 7
<211> LENGTH: 11
<212> TYPE: PRT
<213> ORGANISM: Bos sp.

<400> SEQUENCE: 7

Val Val Asp Leu Leu Tyr Trp Arg Asp Ile Lys
 1               5                   10

<210> SEQ ID NO 8
<211> LENGTH: 16
<212> TYPE: PRT
<213> ORGANISM: Bos sp.

<400> SEQUENCE: 8

Lys Ala Val Ala Ala Glu Ala Ser Met Arg Glu Glu Tyr Ala Asp Phe
 1               5                   10                  15

<210> SEQ ID NO 9
<211> LENGTH: 13
<212> TYPE: PRT
<213> ORGANISM: Bos sp.

<400> SEQUENCE: 9

Glu Tyr Leu Gly Asp Leu Pro Ala Val Leu Pro Thr Glu
 1               5                   10

<210> SEQ ID NO 10
<211> LENGTH: 12
<212> TYPE: PRT
<213> ORGANISM: Bos sp.

<400> SEQUENCE: 10

Glu Ile Ala Asp Ile Gln Asp Gly Ala Gly Ser Leu
 1               5                   10

<210> SEQ ID NO 11
<211> LENGTH: 15
<212> TYPE: PRT
<213> ORGANISM: Bos sp.

<400> SEQUENCE: 11

Lys Pro Tyr Leu Glu Ser Phe Gln Pro Ser Leu Gly Ile Thr Lys
 1               5                   10                  15

<210> SEQ ID NO 12
<211> LENGTH: 9
<212> TYPE: PRT
<213> ORGANISM: Bos sp.

<400> SEQUENCE: 12

Lys Pro Phe Glu Arg Val Trp Glu Val
 1               5

<210> SEQ ID NO 13
<211> LENGTH: 11
<212> TYPE: PRT
<213> ORGANISM: Bos sp.

<400> SEQUENCE: 13

Val Val Asp Leu Leu Tyr Trp Arg Asp Ile Lys
 1               5                   10
```

```
<210> SEQ ID NO 14
<211> LENGTH: 16
<212> TYPE: PRT
<213> ORGANISM: Bos sp.

<400> SEQUENCE: 14

Lys Gly Val Ala Ala Glu Ala Ser Met Gly Glu Glu Tyr Ala Asp Phe
 1               5                  10                  15

<210> SEQ ID NO 15
<211> LENGTH: 13
<212> TYPE: PRT
<213> ORGANISM: Rattus sp.

<400> SEQUENCE: 15

Gly Tyr Leu Gly Asn Leu Ser Ala Val Ser Ser Ser Glu
 1               5                  10

<210> SEQ ID NO 16
<211> LENGTH: 12
<212> TYPE: PRT
<213> ORGANISM: Rattus sp.

<400> SEQUENCE: 16

Glu Ile Ala Asn Ile Gln Ser Gly Ala Asp Ser Leu
 1               5                  10

<210> SEQ ID NO 17
<211> LENGTH: 15
<212> TYPE: PRT
<213> ORGANISM: Rattus sp.

<400> SEQUENCE: 17

Lys Pro Tyr Leu Glu Ser Phe Gln Pro Asn Leu His Ser Thr Lys
 1               5                  10                  15

<210> SEQ ID NO 18
<211> LENGTH: 9
<212> TYPE: PRT
<213> ORGANISM: Rattus sp.

<400> SEQUENCE: 18

Lys Pro Phe Glu Gln Ala Trp Glu Val
 1               5

<210> SEQ ID NO 19
<211> LENGTH: 11
<212> TYPE: PRT
<213> ORGANISM: Rattus sp.

<400> SEQUENCE: 19

Val Val Asp Leu Leu Tyr Trp Arg Asp Ile Lys
 1               5                  10

<210> SEQ ID NO 20
<211> LENGTH: 16
<212> TYPE: PRT
<213> ORGANISM: Rattus sp.

<400> SEQUENCE: 20

Met Gln Met Ser Val Val Ala Pro Val Arg Glu Glu Tyr Ala Asp Phe
 1               5                  10                  15
```

<210> SEQ ID NO 21
<211> LENGTH: 186
<212> TYPE: PRT
<213> ORGANISM: Homo sapiens

<400> SEQUENCE: 21

Asp Leu Leu Tyr Trp Arg Asp Ile Lys Gln Thr Gly Ile Val Phe Gly
1               5                   10                  15

Ser Phe Leu Leu Leu Phe Ser Leu Thr Gln Phe Ser Val Val Ser
            20                  25                  30

Val Val Ala Tyr Leu Ala Leu Ala Ala Leu Ser Ala Thr Ile Ser Phe
        35                  40                  45

Arg Ile Tyr Lys Ser Val Leu Gln Ala Val Gln Lys Thr Asp Glu Gly
    50                  55                  60

His Pro Phe Lys Ala Tyr Leu Glu Leu Glu Ile Thr Leu Ser Gln Glu
65                  70                  75                  80

Gln Ile Gln Lys Tyr Thr Asp Cys Leu Gln Phe Tyr Val Asn Ser Thr
                85                  90                  95

Leu Lys Glu Leu Arg Arg Leu Phe Leu Val Gln Asp Leu Val Asp Ser
            100                 105                 110

Leu Lys Phe Ala Val Leu Met Trp Leu Leu Thr Tyr Val Gly Ala Leu
        115                 120                 125

Phe Asn Gly Leu Thr Leu Leu Met Ala Val Val Ser Met Phe Thr
    130                 135                 140

Leu Pro Val Val Tyr Val Lys His Gln Ala Gln Ile Asp Gln Tyr Leu
145                 150                 155                 160

Gly Leu Val Arg Thr His Ile Asn Ala Val Val Ala Lys Ile Gln Ala
                165                 170                 175

Lys Ile Pro Gly Ala Lys Arg His Ala Glu
            180                 185

<210> SEQ ID NO 22
<211> LENGTH: 186
<212> TYPE: PRT
<213> ORGANISM: Rattus sp.

<400> SEQUENCE: 22

Asp Leu Leu Tyr Trp Arg Asp Ile Lys Gln Thr Gly Ile Val Phe Gly
1               5                   10                  15

Ser Phe Leu Leu Leu Phe Ser Leu Thr Gln Phe Ser Val Val Ser
            20                  25                  30

Val Val Ala Tyr Leu Ala Leu Ala Ala Leu Ser Ala Thr Ile Ser Phe
        35                  40                  45

Arg Ile Tyr Lys Ser Val Leu Gln Ala Val Gln Lys Thr Asp Glu Gly
    50                  55                  60

His Pro Phe Lys Ala Tyr Leu Glu Leu Glu Ile Thr Leu Ser Gln Glu
65                  70                  75                  80

Gln Ile Gln Lys Tyr Thr Asp Cys Leu Gln Leu Tyr Val Asn Ser Thr
                85                  90                  95

Leu Lys Glu Leu Arg Arg Leu Phe Leu Val Gln Asp Leu Val Asp Ser
            100                 105                 110

Leu Lys Phe Ala Val Leu Met Trp Leu Leu Thr Tyr Val Gly Ala Leu
        115                 120                 125

Phe Asn Gly Leu Thr Leu Leu Leu Met Ala Val Val Ser Met Phe Thr
    130                 135                 140

```
Leu Pro Val Val Tyr Val Lys His Gln Ala Gln Val Asp Gln Tyr Leu
145                 150                 155                 160

Gly Leu Val Arg Thr His Ile Asn Thr Val Val Ala Lys Ile Gln Ala
            165                 170                 175

Lys Ile Pro Gly Ala Lys Arg His Ala Glu
        180                 185

<210> SEQ ID NO 23
<211> LENGTH: 186
<212> TYPE: PRT
<213> ORGANISM: Gallus gallus

<400> SEQUENCE: 23

Asn Leu Leu Tyr Trp Arg Asp Ile Lys Gln Thr Gly Ile Val Phe Gly
1               5                   10                  15

Ser Leu Leu Leu Leu Phe Ser Leu Thr Gln Phe Ser Val Val Ser
            20                  25                  30

Val Val Ala Tyr Leu Ala Leu Ala Gly Leu Ser Ala Thr Ile Ser Phe
            35                  40                  45

Arg Ile Tyr Lys Ser Val Leu Gln Ala Val Gln Lys Thr Asp Glu Gly
50                  55                  60

His Pro Phe Lys Ala Tyr Leu Asp Met Glu Met Asn Leu Ser Gln Asp
65                  70                  75                  80

Gln Ile Gln Lys Tyr Thr Asp Cys Leu Gln Leu Tyr Val Asn Ser Thr
                85                  90                  95

Val Lys Glu Leu Arg Arg Leu Phe Leu Val Gln Asp Leu Val Asp Ser
            100                 105                 110

Leu Lys Phe Ala Val Leu Met Trp Leu Leu Thr Tyr Val Gly Ala Leu
        115                 120                 125

Phe Asn Gly Leu Thr Leu Leu Ile Met Ala Val Val Ser Met Phe Thr
130                 135                 140

Leu Pro Val Val Tyr Asp Lys Tyr Gln Ala Gln Ile Asp Gln Tyr Leu
145                 150                 155                 160

Gly Leu Val Arg Thr His Ile Asn Thr Val Val Ala Lys Ile Gln Ala
            165                 170                 175

Lys Ile Pro Gly Ala Lys Arg Lys Ala Glu
        180                 185

<210> SEQ ID NO 24
<211> LENGTH: 186
<212> TYPE: PRT
<213> ORGANISM: Bos sp.

<400> SEQUENCE: 24

Asp Leu Leu Tyr Trp Arg Asp Ile Lys Lys Thr Gly Val Val Phe Gly
1               5                   10                  15

Ala Ser Leu Phe Leu Leu Leu Ser Leu Thr Val Phe Ser Ile Val Ser
            20                  25                  30

Val Thr Ala Tyr Ile Ala Leu Ala Leu Leu Ser Val Thr Ile Ser Phe
        35                  40                  45

Arg Ile Tyr Lys Gly Val Ile Gln Ala Ile Gln Lys Ser Asp Glu Gly
50                  55                  60

His Pro Phe Arg Ala Tyr Leu Glu Ser Glu Val Ala Ile Ser Glu Glu
65                  70                  75                  80

Leu Val Gln Lys Tyr Ser Asn Ser Ala Leu Gly His Val Asn Cys Thr
            85                  90                  95
```

```
Ile Lys Glu Leu Arg Arg Leu Phe Leu Val Asp Asp Leu Val Asp Ser
            100                 105                 110

Leu Lys Phe Ala Val Leu Met Trp Val Phe Thr Tyr Val Gly Ala Leu
            115                 120                 125

Phe Asn Gly Leu Thr Leu Leu Ile Leu Ala Leu Ile Ser Leu Phe Ser
            130                 135                 140

Val Pro Val Ile Tyr Glu Arg His Gln Ala Gln Ile Asp His Tyr Leu
145                 150                 155                 160

Gly Leu Ala Asn Lys Asn Val Lys Asp Ala Met Ala Lys Ile Gln Ala
                165                 170                 175

Lys Ile Pro Gly Leu Lys Arg Lys Ala Glu
            180                 185

<210> SEQ ID NO 25
<211> LENGTH: 186
<212> TYPE: PRT
<213> ORGANISM: Rattus sp.

<400> SEQUENCE: 25

Asp Leu Leu Tyr Trp Arg Asp Ile Lys Lys Thr Gly Val Val Phe Gly
1               5                   10                  15

Ala Ser Leu Phe Leu Leu Leu Ser Leu Thr Val Phe Ser Ile Val Ser
            20                  25                  30

Val Thr Ala Tyr Ile Ala Leu Ala Leu Leu Ser Val Thr Ile Ser Phe
        35                  40                  45

Arg Ile Tyr Lys Gly Val Ile Gln Ala Ile Gln Lys Ser Asp Glu Gly
    50                  55                  60

His Pro Phe Arg Ala Tyr Leu Glu Ser Glu Val Ala Ile Ser Glu Glu
65                  70                  75                  80

Leu Val Gln Lys Tyr Ser Asn Ser Ala Leu Gly His Val Asn Ser Thr
                85                  90                  95

Ile Lys Glu Leu Arg Arg Leu Phe Leu Val Asp Asp Leu Val Asp Ser
            100                 105                 110

Leu Lys Phe Ala Val Leu Met Trp Val Phe Thr Tyr Val Gly Ala Leu
            115                 120                 125

Phe Asn Gly Leu Thr Leu Leu Ile Leu Ala Leu Ile Ser Leu Phe Ser
            130                 135                 140

Ile Pro Val Ile Tyr Glu Arg His Gln Val Gln Ile Asp His Tyr Leu
145                 150                 155                 160

Gly Leu Ala Asn Lys Ser Val Lys Asp Ala Met Ala Lys Ile Gln Ala
                165                 170                 175

Lys Ile Pro Gly Leu Lys Arg Lys Ala Asp
            180                 185

<210> SEQ ID NO 26
<211> LENGTH: 194
<212> TYPE: PRT
<213> ORGANISM: C. elegans

<400> SEQUENCE: 26

Asp Val Ile Tyr Trp Arg Asp Ala Lys Lys Ser Ala Ile Val Leu Ser
1               5                   10                  15

Leu Ala Leu Leu Val Leu Phe Val Leu Ala Lys Tyr Pro Leu Leu Thr
            20                  25                  30

Val Val Thr Tyr Ser Leu Leu Leu Ala Leu Gly Ala Ala Ala Gly Phe
        35                  40                  45
```

```
Arg Val Phe Lys Lys Val Glu Ala Gln Ile Lys Lys Thr Asp Ser Glu
         50                  55                  60
His Pro Phe Ser Glu Ile Leu Ala Gln Asp Leu Thr Leu Pro Gln Glu
 65                  70                  75                  80
Lys Val His Ala Gln Ala Asp Val Phe Val Glu His Ala Thr Cys Ile
                 85                  90                  95
Ala Asn Lys Leu Lys Lys Leu Val Phe Val Glu Ser Pro Leu Glu Ser
            100                 105                 110
Ile Lys Phe Gly Leu Val Leu Trp Ser Leu Thr Tyr Ile Ala Ser Trp
        115                 120                 125
Phe Ser Gly Phe Thr Leu Ala Ile Leu Gly Leu Leu Gly Val Phe Ser
130                 135                 140
Val Pro Lys Val Tyr Glu Ser Asn Gln Glu Ala Ile Asp Pro His Leu
145                 150                 155                 160
Ala Thr Ile Ser Gly His Leu Lys Asn Val Gln Asn Ile Ile Asp Glu
                165                 170                 175
Lys Leu Pro Phe Leu Arg Ser Ala Pro Val Ala Ala Glu Glu Lys Lys
            180                 185                 190
Asp Gln

<210> SEQ ID NO 27
<211> LENGTH: 150
<212> TYPE: PRT
<213> ORGANISM: D. melanogaster

<400> SEQUENCE: 27

Asn Leu Leu Leu Trp Arg Asn Ser Arg Lys Thr Leu Ile Val Phe Thr
 1               5                  10                  15
Gly Ile Leu Leu Leu Leu Asp Val Met Val His Ser Val Ile Ser
             20                  25                  30
Val Ile Ser Met Val Gly Ile Thr Val Leu Ile Ala Ala Ile Gly His
         35                  40                  45
Arg Leu Leu Val Gln Phe Trp Ser Ile Trp Lys Lys Asp Glu Asn Lys
 50                  55                  60
Asp Gln Ile Leu Arg Phe Tyr Pro His Pro Lys Ile Glu Ile Pro Arg
 65                  70                  75                  80
Glu Glu Thr Leu Tyr Leu Ala Gly Lys Ala Val Ser His Ile Asn Leu
                 85                  90                  95
Ile Leu Asn Arg Met Ile Glu Leu Leu Leu Val Glu Lys Trp Glu Asp
            100                 105                 110
Ser Leu Lys Phe Leu Val Leu Leu Cys Gly Ile Asn Leu Leu Gly Asp
        115                 120                 125
Cys Phe Asn Gly Leu Thr Leu Leu Ile Phe Gly Met Cys Ile Cys Cys
130                 135                 140
Leu Thr Leu Leu Tyr Leu
145                 150

<210> SEQ ID NO 28
<211> LENGTH: 3833
<212> TYPE: DNA
<213> ORGANISM: Bos sp.

<400> SEQUENCE: 28
ctatctcctc tctcagccgc tgcttttaaa gaacgtgaat accttggtga tttaccagca    60
gtactgccca ctgaaggaac acttccagca acttcaaatg aagcttctaa agcattctca   120
```

```
gagaaggcaa aaaatccatt tgtagagaga aatttaacag aattttcaga attggaatat      180
tcagaaatgg aatcatcatt cagtggctct caaaaggcag aacctgccgt aacagtagcg      240
aatcctaggg acgaaatagt tgtgaggagt agagataaag aagaggactt agttagtctt      300
aacatccttc atactcagca ggagttatct acagtcctta cgaaatcagt tgaagaagaa      360
gatagagttc tgtctccaga aaaaacaaag gacagtttta aggaaagggg agttgcagca      420
gaagcttcta tgggggagga atatgcagac ttcaaaccat ttgagcgagt atgggaagtg      480
aaagatactt acaagcaaga tagtgatgtt ttgattgctg gaggtaatat agagagcaaa      540
ttggaaggta aagtggataa gaaacacttt tcagatagcc ttgaacaaac aaatcgtgaa      600
aaagatagtg aaagcagtaa tgatgacact tcatttccca gtacaccaga agctgtaaga      660
ggtggttccg gagcgtacat cacgtgtgct cccttttaacc caacaactga gaatgtttca      720
acaaacattt ttcccttgtt ggaagatcat acttcggaaa ataagacaga tgaaaaaaag      780
atagaaaaaa aaaggcacaa attgtaacag agaagaatgc aagtgtcaag acatcaaacc      840
cttttccttat ggcagcacag gagtctaaga cagattacgt tacaacagat catgtgtcaa      900
aggtgaccga ggaagtagtg gcaaacatgc ctgaaggtct aacccagat ttggttcagg      960
aagcatgtga agtgaattg aatgaagcta ctggtacaaa aattgccttt gaaacaaaaa     1020
tggacctggt tcaaacttca gaagctgtgc aggagtcact ttaccctgta acacagcttt     1080
gcccatcttt tgaagaatct gaagctactc cgtcaccggt tttgcctgac attgtcatgg     1140
aagcaccatt aaattctgta gttcctagtg ctggtgcttc tgcagtgcag ctcagttcat     1200
caccattaga aactcttcct tcagttaatt atgaaagcat aaagtttgag cctgaaaatc     1260
ccccaccata tgaggaggcc atgaatgtat cactaaaaaa agaatcagga atgaatgaag     1320
aaatcacaga gcctgaaggt attagtgtag ctgttcagga aacagaagct ccttatatat     1380
ctattgcatg tgatttaatt aaagaaacaa agatctctac tgaaccgact ccagatttct     1440
ctagttattc agaaatagca gaagttgcac agccagtgcc cgagcattct gagctagttg     1500
aagattcctc ccccgattct gaaccagttg acttatttag tgatgattca atacccgaag     1560
ttccacaaaa acaagatgaa gctgtaatac ttgtgaaaga aaacctcact gaaatttcat     1620
ctgagtcaat gacaggacat gacaataagg gaaaactcag tgcttcacca tcacctgagg     1680
gaggaaaacc gtatttggag tcttttcagc ccagtttagg catcacaaaa gataccttag     1740
cacctgatga agtttcagca ttgacccaaa aggagaaaat cccttttgcag atggaggagc     1800
tcaatactgc agtttattca agtgatggct tattcattgc tcaggaagca aacctaagag     1860
aaagtgaaac attttcagat tcatctccga ttgagattat agatgagttc ccgacctttg     1920
tcagttctaa agcagattct tctcctacat tagccaggga atacactgac ctagaagtag     1980
cccacaaaag tgaaattgct gacatccagg atggagctgg gtcattggct tgtgcaggat     2040
tgccccatga cctttctttc aagagtatac aacctaaaga ggaagttcat gtcccagatg     2100
agttctccaa agatagggggt gatgtttcaa aggtgcccgt actgcctcca gatgtttctg     2160
cttttggatgc tcaagcagag ataggcagca tagaaaaacc caagttctt gtgaagaag     2220
ccgagagaaa acttccttct gatacagaaa aagagcgaag atctccatct gctatatttt     2280
cagcagagct gagtaaaaact tcagttgttg acctcctcta ctggagagac attaagaaga     2340
ctggagtggt gttttggtgcc agcttgttcc tgctgctctc gctgacagta ttcagcattg     2400
tgagtgtaac ggcctacatt gccttggccc tgctctctgt gactatcagc tttaggatat     2460
ataagggtgt gatccaggct atccagaaat ctgatgaagg ccacccattc agggcatatt     2520
```

-continued

```
tggaatctga agttgctata tctgaggagt tggttcagaa gtacagcaat tctgctcttg    2580
gtcatgttaa ctgcacaata aaagaactca gacgcctctt cttagttgat gatttagttg    2640
attctctgaa gtttgcagtg ttgatgtggg tatttaccta tgttggtgcc ttgttcaatg    2700
gtctgacact actaattttg gctctgattt cactcttcag tgttcctgtt atttatgaac    2760
ggcatcaggc gcaaatagat cattatctgg gacttgcaaa taagaatgtt aaagatgcta    2820
tggctaaaat ccaagcaaaa atccctggat tgaagcgtaa agctgaatga aaagcctga    2880
aagagttaac aatagaggag tttatcttta aggggatat tcatttgatt ccattgggga    2940
gggtcaggga agaacaaagc cttgacattg cagtgcagtt tcacagatct ttattttag    3000
caacgcagtg tctgaggaaa aatgacctgt cttgactgcc ctgtgttcat catcttaagt    3060
attgtaagct gctatgtatg gatttaaatc gtaatcatat ttgttttcc tgtatgaggc    3120
actggtgaat aaacaaagat ctgagaaagc tgtatattac actttgtcgc aggtagtctt    3180
gctgtatttg gggaattgca agaaagtgg agctgacaga aataacccct tcacagttt    3240
gtgcactgtg tacggtctgt gtaggttgat gcagattttc tgaaatgaaa tgtttagacg    3300
agatcatgcc accaaggcag gagtgaaaaa gcttgccttt cctggtatgt tctaggtgta    3360
ttgtgaaatt tactgttgta ttaattgcca atataagtaa atatagatta tatatatcta    3420
tatatagtgt ttcacgaagc ttagcccttt accttccag ctgccccaca gtgcttgata    3480
cttctgtcat gggttttatg tgtgtagtcc caaagcacat aagctaggga gaaacgtact    3540
tctaggcgca ctaccatctg tttttcaacac gaaccgacgc catgcaaaca gaactcctca    3600
acataaactt cactgcacag acttactgta gttaatttta tcacaaactc tggactgaat    3660
ctaatgcttc caaaaatgtt tgcaaatatc aaacattgtt atgtaagaaa atataaatga    3720
cgatttatac aattgtggtt taagctgtat tgaactaaat ctgtggaatg cattgtgaac    3780
tgtaaaagca agtatcaat aaagcttata gacttaaaaa aaaaaaaaaa aaa            3833
```

<210> SEQ ID NO 29
<211> LENGTH: 1178
<212> TYPE: PRT
<213> ORGANISM: Homo sapiens
<220> FEATURE:
<221> NAME/KEY: VARIANT
<222> LOCATION: (1)...(1178) at all Xaa position
<223> OTHER INFORMATION: Xaa = any amino acid

<400> SEQUENCE: 29

```
Met Glu Asp Leu Asp Gln Ser Pro Leu Val Ser Ser Asp Ser Pro
 1               5                  10                  15

Pro Arg Pro Gln Pro Ala Phe Lys Tyr Gln Phe Val Arg Glu Pro Glu
                20                  25                  30

Asp Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Pro Leu Ser Ala Ala Ala Val
            115                     120                     125
```

```
Ser Pro Ser Lys Leu Pro Glu Asp Asp Glu Pro Ala Arg Pro Pro
    130                 135                 140

Pro Pro Pro Ala Ser Val Ser Pro Gln Ala Glu Pro Val Trp Thr
145                 150                 155                 160

Pro Pro Ala Pro Ala Pro Ala Ala Pro Ser Thr Pro Ala Ala Pro
                165                 170                 175

Lys Arg Arg Gly Ser Ser Gly Ala Val Val Xaa Xaa Xaa Lys Ile
                180                 185                 190

Met Asp Leu Lys Glu Gln Pro Gly Asn Thr Ile Ser Ala Gly Gln Glu
            195                 200                 205

Asp Phe Pro Ser Val Leu Leu Glu Thr Ala Ala Ser Xaa Pro Ser Leu
    210                 215                 220

Ser Pro Leu Ser Ala Ala Ser Phe Lys Glu His Glu Tyr Leu Gly Asn
225                 230                 235                 240

Leu Ser Thr Val Leu Pro Thr Glu Gly Thr Leu Gln Glu Asn Val Ser
                245                 250                 255

Glu Ala Ser Lys Glu Val Ser Glu Lys Ala Lys Thr Leu Leu Ile Asp
            260                 265                 270

Arg Asp Leu Thr Glu Phe Ser Glu Leu Glu Tyr Ser Glu Met Gly Ser
    275                 280                 285

Ser Phe Ser Val Ser Pro Lys Ala Glu Ser Ala Val Ile Val Ala Asn
290                 295                 300

Pro Arg Glu Glu Ile Ile Val Lys Asn Lys Asp Glu Glu Lys Leu
305                 310                 315                 320

Val Ser Asn Asn Ile Leu His Xaa Gln Gln Glu Leu Pro Thr Ala Leu
                325                 330                 335

Thr Lys Leu Val Lys Glu Asp Glu Val Val Ser Ser Lys Ala Lys
            340                 345                 350

Asp Ser Phe Asn Glu Lys Arg Val Ala Val Glu Ala Pro Met Arg Glu
            355                 360                 365

Glu Tyr Ala Asp Phe Lys Pro Phe Glu Arg Val Trp Glu Val Lys Asp
    370                 375                 380

Ser Lys Glu Asp Ser Asp Met Leu Ala Ala Gly Gly Lys Ile Glu Ser
385                 390                 395                 400

Asn Leu Glu Ser Lys Val Asp Lys Lys Cys Phe Ala Asp Ser Leu Glu
                405                 410                 415

Gln Thr Asn His Glu Lys Asp Ser Glu Ser Ser Asn Asp Thr Ser
            420                 425                 430

Phe Pro Ser Thr Pro Glu Gly Ile Lys Asp Arg Ser Gly Ala Tyr Ile
            435                 440                 445

Thr Cys Ala Pro Phe Asn Pro Ala Ala Thr Glu Ser Ile Ala Thr Asn
    450                 455                 460

Ile Phe Pro Leu Leu Glu Asp Pro Thr Ser Glu Asn Xaa Thr Asp Glu
465                 470                 475                 480

Lys Lys Ile Glu Glu Lys Lys Ala Gln Ile Val Thr Glu Lys Asn Thr
                485                 490                 495

Ser Thr Lys Thr Ser Asn Pro Phe Phe Val Ala Ala Gln Asp Ser Glu
            500                 505                 510

Thr Asp Tyr Val Thr Thr Asp Asn Leu Thr Lys Val Thr Glu Glu Val
            515                 520                 525

Val Ala Asn Met Pro Glu Gly Leu Thr Pro Asp Leu Val Gln Glu Ala
530                 535                 540
```

```
Cys Glu Ser Glu Leu Asn Glu Val Thr Gly Thr Lys Ile Ala Tyr Glu
545                 550                 555                 560

Thr Lys Met Asp Leu Val Gln Thr Ser Glu Val Met Gln Glu Ser Leu
                565                 570                 575

Tyr Pro Ala Ala Gln Leu Cys Pro Ser Phe Glu Glu Ser Glu Ala Thr
                580                 585                 590

Pro Ser Pro Val Leu Pro Asp Ile Val Met Glu Ala Pro Leu Asn Ser
            595                 600                 605

Ala Val Pro Ser Ala Gly Ala Ser Val Ile Gln Pro Ser Ser Ser Pro
        610                 615                 620

Leu Glu Ala Ser Ser Val Asn Tyr Glu Ser Ile Lys His Glu Pro Glu
625                 630                 635                 640

Asn Pro Pro Pro Tyr Glu Glu Ala Met Ser Val Ser Leu Lys Val Ser
                645                 650                 655

Gly Ile Lys Glu Glu Ile Lys Glu Pro Glu Asn Ile Asn Ala Ala Leu
                660                 665                 670

Gln Glu Thr Glu Ala Pro Tyr Ile Ser Ile Ala Cys Asp Leu Ile Lys
            675                 680                 685

Glu Thr Lys Leu Ser Ala Glu Pro Ala Pro Asp Phe Ser Asp Tyr Ser
        690                 695                 700

Glu Met Ala Lys Val Glu Gln Pro Val Pro Asp His Ser Glu Leu Val
705                 710                 715                 720

Glu Asp Ser Ser Pro Asp Ser Glu Pro Val Asp Leu Phe Ser Asp Asp
                725                 730                 735

Ser Ile Pro Asp Val Pro Gln Lys Gln Asp Glu Thr Val Met Leu Val
                740                 745                 750

Lys Glu Ser Leu Thr Glu Thr Ser Phe Glu Ser Met Ile Glu Tyr Glu
            755                 760                 765

Asn Lys Glu Lys Leu Ser Ala Leu Pro Pro Glu Gly Gly Lys Pro Tyr
        770                 775                 780

Leu Glu Ser Phe Lys Leu Ser Leu Asp Asn Thr Lys Asp Thr Leu Leu
785                 790                 795                 800

Pro Asp Glu Val Ser Thr Leu Ser Lys Lys Glu Lys Ile Pro Leu Gln
                805                 810                 815

Met Glu Glu Leu Ser Thr Ala Val Tyr Ser Asn Asp Asp Leu Phe Ile
            820                 825                 830

Ser Lys Glu Ala Gln Ile Arg Glu Thr Glu Thr Phe Ser Asp Ser Ser
        835                 840                 845

Pro Ile Glu Ile Ile Asp Glu Phe Pro Thr Leu Ile Ser Ser Lys Thr
850                 855                 860

Asp Ser Phe Ser Lys Leu Ala Arg Glu Tyr Thr Asp Leu Glu Val Ser
865                 870                 875                 880

His Lys Ser Glu Ile Ala Asn Ala Pro Asp Gly Ala Gly Ser Leu Pro
                885                 890                 895

Cys Thr Glu Leu Pro His Asp Leu Ser Leu Lys Asn Ile Gln Pro Lys
                900                 905                 910

Val Glu Glu Lys Ile Ser Phe Ser Asp Asp Phe Ser Lys Asn Gly Ser
            915                 920                 925

Ala Thr Ser Lys Val Leu Leu Leu Pro Pro Asp Val Ser Ala Leu Gly
        930                 935                 940

His Thr Gln Ala Glu Ile Glu Ser Ile Val Lys Pro Lys Val Leu Glu
945                 950                 955                 960
```

-continued

Lys Glu Ala Glu Lys Lys Leu Pro Ser Asp Thr Lys Glu Asp Arg
                965                 970                 975

Ser Pro Ser Ala Ile Phe Ser Ala Asp Leu Gly Lys Thr Ser Val Val
                980                 985                 990

Asp Leu Leu Tyr Trp Arg Asp Ile Lys Lys Thr Gly Val Val Phe Gly
                995                 1000                1005

Ala Ser Leu Phe Leu Leu Leu Ser Leu Thr Val Phe Ser Ile Val Ser
            1010                1015                1020

Val Thr Ala Tyr Ile Ala Leu Ala Leu Leu Ser Val Thr Ile Ser Phe
1025                1030                1035                1040

Arg Ile Tyr Lys Gly Val Ile Gln Ala Ile Gln Lys Ser Asp Glu Gly
                1045                1050                1055

His Pro Phe Arg Ala Tyr Leu Glu Ser Glu Val Ala Ile Ser Glu Glu
            1060                1065                1070

Leu Val Gln Lys Tyr Ser Asn Ser Ala Leu Gly His Val Asn Cys Thr
                1075                1080                1085

Ile Lys Glu Leu Arg Arg Leu Phe Leu Val Asp Asp Leu Val Asp Ser
            1090                1095                1100

Leu Lys Phe Ala Val Leu Met Trp Val Phe Thr Tyr Val Gly Ala Leu
1105                1110                1115                1120

Phe Asn Gly Leu Thr Leu Leu Ile Leu Ala Leu Ile Ser Leu Phe Ser
                1125                1130                1135

Val Pro Val Ile Tyr Glu Arg His Gln Ala Gln Ile Asp His Tyr Leu
                1140                1145                1150

Gly Leu Ala Asn Lys Asn Val Lys Asp Ala Met Ala Lys Ile Gln Ala
            1155                1160                1165

Lys Ile Pro Gly Leu Lys Arg Lys Ala Glu
        1170                1175

<210> SEQ ID NO 30
<211> LENGTH: 1163
<212> TYPE: PRT
<213> ORGANISM: Rattus sp.
<220> FEATURE:
<221> NAME/KEY: VARIANT
<222> LOCATION: (1)...(1163) at all Xaa position
<223> OTHER INFORMATION: Xaa = any amino acid

<400> SEQUENCE: 30

Met Glu Asp Ile Asp Gln Ser Ser Leu Val Ser Ser Thr Asp Ser
 1               5                  10                  15

Pro Pro Arg Pro Pro Ala Phe Lys Tyr Gln Phe Val Thr Glu Pro
                20                  25                  30

Glu Asp Glu Glu Asp Glu Glu Glu Glu Asp Glu Glu Glu Asp Asp
                35                  40                  45

Glu Asp Leu Glu Glu Leu Glu Val Leu Glu Arg Lys Pro Ala Ala Gly
            50                  55                  60

Leu Ser Ala Ala Val Pro Pro Ala Ala Ala Pro Leu Leu Asp
65                  70                  75              80

Phe Ser Asp Ser Val Pro Ala Pro Arg Gly Pro Leu Pro Ala
                85                  90                  95

Ala Pro Pro Ala Ala Pro Glu Arg Gln Pro Ser Trp Glu Arg Ser Pro
            100                 105                 110

Ala Ala Pro Ala Pro Ser Leu Pro Pro Ala Ala Val Leu Pro Ser
            115                 120                 125

```
Lys Leu Pro Glu Asp Asp Glu Pro Pro Ala Arg Pro Pro Pro Pro
130                 135                 140

Pro Ala Gly Ala Ser Pro Leu Ala Glu Pro Ala Ala Pro Pro Ser Thr
145                 150                 155                 160

Pro Ala Ala Pro Lys Arg Arg Gly Ser Gly Ser Val Asp Glu Thr Leu
                165                 170                 175

Phe Ala Leu Pro Ala Ala Ser Glu Pro Val Ile Pro Ser Ser Ala Glu
                180                 185                 190

Lys Ile Met Asp Leu Met Glu Gln Pro Gly Asn Thr Val Ser Ser Gly
                195                 200                 205

Gln Glu Asp Phe Pro Ser Val Leu Leu Glu Thr Ala Ala Ser Leu Pro
210                 215                 220

Ser Leu Ser Pro Leu Ser Thr Val Ser Phe Lys Glu His Gly Tyr Leu
225                 230                 235                 240

Gly Asn Leu Ser Ala Val Ser Ser Ser Glu Gly Thr Ile Glu Glu Thr
                245                 250                 255

Leu Asn Glu Ala Ser Lys Glu Leu Pro Glu Arg Ala Thr Asn Pro Phe
                260                 265                 270

Val Asn Arg Asp Leu Ala Glu Phe Ser Glu Leu Glu Tyr Ser Glu Met
                275                 280                 285

Gly Ser Ser Phe Lys Gly Ser Pro Lys Gly Glu Ser Ala Ile Leu Val
290                 295                 300

Glu Asn Thr Lys Glu Glu Val Ile Val Arg Ser Lys Asp Lys Glu Asp
305                 310                 315                 320

Leu Val Cys Ser Ala Ala Leu His Ser Pro Gln Glu Ser Pro Val Gly
                325                 330                 335

Lys Glu Asp Arg Val Val Ser Pro Glu Lys Thr Met Asp Ile Phe Asn
                340                 345                 350

Glu Met Gln Met Ser Val Val Ala Pro Val Arg Glu Glu Tyr Ala Asp
                355                 360                 365

Phe Lys Pro Phe Glu Gln Ala Trp Glu Val Lys Asp Thr Tyr Glu Gly
                370                 375                 380

Ser Arg Asp Val Leu Ala Ala Arg Ala Asn Val Glu Ser Lys Val Asp
385                 390                 395                 400

Arg Lys Cys Leu Glu Asp Ser Leu Glu Gln Lys Ser Leu Gly Lys Asp
                405                 410                 415

Ser Glu Gly Arg Asn Glu Asp Ala Ser Phe Pro Ser Thr Pro Glu Pro
                420                 425                 430

Val Lys Asp Ser Ser Arg Ala Tyr Ile Thr Cys Ala Ser Phe Thr Ser
                435                 440                 445

Ala Thr Glu Ser Thr Thr Ala Asn Thr Phe Pro Leu Leu Glu Asp His
                450                 455                 460

Thr Ser Glu Asn Xaa Thr Asp Glu Lys Lys Ile Glu Glu Arg Lys Ala
465                 470                 475                 480

Gln Ile Ile Thr Glu Lys Thr Ser Pro Lys Thr Ser Asn Pro Phe Leu
                485                 490                 495

Val Ala Val Gln Asp Ser Glu Ala Asp Tyr Val Thr Thr Asp Thr Leu
                500                 505                 510

Ser Lys Val Thr Glu Ala Ala Val Ser Asn Met Pro Glu Gly Leu Thr
                515                 520                 525

Pro Asp Leu Val Gln Glu Ala Cys Glu Ser Glu Leu Asn Glu Ala Thr
530                 535                 540
```

```
Gly Thr Lys Ile Ala Tyr Glu Thr Lys Val Asp Leu Val Gln Thr Ser
545                 550                 555                 560

Glu Ala Ile Gln Glu Ser Leu Tyr Pro Thr Ala Gln Leu Cys Pro Ser
                565                 570                 575

Phe Glu Ala Glu Ala Thr Pro Ser Pro Val Leu Pro Asp Ile Val
            580                 585                 590

Met Glu Ala Pro Leu Asn Ser Leu Leu Pro Ser Ala Gly Ala Ser Val
                595                 600                 605

Val Gln Pro Ser Val Ser Pro Leu Glu Ala Pro Pro Val Ser Tyr
    610                 615                 620

Asp Ser Ile Lys Leu Glu Pro Glu Asn Pro Pro Tyr Glu Glu Ala
625                 630                 635                 640

Met Asn Val Ala Leu Lys Ala Leu Gly Thr Lys Glu Gly Ile Lys Glu
                645                 650                 655

Pro Glu Ser Phe Asn Ala Ala Val Gln Glu Thr Glu Ala Pro Tyr Ile
                660                 665                 670

Ser Ile Ala Cys Asp Leu Ile Lys Glu Thr Lys Leu Ser Thr Glu Pro
                675                 680                 685

Ser Pro Asp Phe Ser Asn Tyr Ser Glu Ile Ala Lys Phe Glu Lys Ser
                690                 695                 700

Val Pro Glu His Ala Glu Leu Val Glu Asp Ser Ser Pro Glu Ser Glu
705                 710                 715                 720

Pro Val Asp Leu Phe Ser Asp Asp Ser Ile Pro Glu Val Pro Gln Thr
                725                 730                 735

Gln Glu Glu Ala Val Met Leu Met Lys Glu Ser Leu Thr Glu Val Ser
                740                 745                 750

Glu Thr Val Ala Gln His Lys Glu Glu Arg Leu Ser Ala Ser Pro Gln
                755                 760                 765

Glu Leu Gly Lys Pro Tyr Leu Glu Ser Phe Gln Pro Asn Leu His Ser
                770                 775                 780

Thr Lys Asp Ala Ala Ser Asn Asp Ile Pro Thr Leu Thr Lys Lys Glu
785                 790                 795                 800

Lys Ile Ser Leu Gln Met Glu Glu Phe Asn Thr Ala Ile Tyr Ser Asn
                805                 810                 815

Asp Asp Leu Leu Ser Ser Lys Glu Asp Lys Ile Lys Glu Ser Glu Thr
                820                 825                 830

Phe Ser Asp Ser Ser Pro Ile Glu Ile Asp Glu Phe Pro Thr Phe
                835                 840                 845

Val Ser Ala Lys Asp Asp Ser Pro Lys Leu Ala Lys Glu Tyr Thr Asp
850                 855                 860

Leu Glu Val Ser Asp Lys Ser Glu Ile Ala Asn Ile Gln Ser Gly Ala
865                 870                 875                 880

Asp Ser Leu Pro Cys Leu Glu Leu Pro Cys Asp Leu Ser Phe Lys Asn
                885                 890                 895

Ile Tyr Pro Lys Asp Glu Val His Val Ser Asp Glu Phe Ser Glu Asn
                900                 905                 910

Arg Ser Ser Val Ser Lys Ala Ser Ile Ser Pro Ser Asn Val Ser Ala
                915                 920                 925

Leu Glu Pro Gln Thr Glu Met Gly Ser Ile Val Lys Ser Lys Ser Leu
                930                 935                 940

Thr Lys Glu Ala Glu Lys Lys Leu Pro Ser Asp Thr Glu Lys Glu Asp
945                 950                 955                 960
```

-continued

```
Arg Ser Leu Ser Ala Val Leu Ser Ala Glu Leu Ser Lys Thr Ser Val
            965                 970                 975
Val Asp Leu Leu Tyr Trp Arg Asp Ile Lys Lys Thr Gly Val Val Phe
            980                 985                 990
Gly Ala Ser Leu Phe Leu Leu Leu Ser Leu Thr Val Phe Ser Ile Val
            995                 1000                1005
Ser Val Thr Ala Tyr Ile Ala Leu Ala Leu Leu Ser Val Thr Ile Ser
        1010                1015                1020
Phe Arg Ile Tyr Lys Gly Val Ile Gln Ala Ile Gln Lys Ser Asp Glu
1025                1030                1035                1040
Gly His Pro Phe Arg Ala Tyr Leu Glu Ser Glu Val Ala Ile Ser Glu
                1045                1050                1055
Glu Leu Val Gln Lys Tyr Ser Asn Ser Ala Leu Gly His Val Asn Ser
            1060                1065                1070
Thr Ile Lys Glu Leu Arg Arg Leu Phe Leu Val Asp Asp Leu Val Asp
        1075                1080                1085
Ser Leu Lys Phe Ala Val Leu Met Trp Val Phe Thr Tyr Val Gly Ala
        1090                1095                1100
Leu Phe Asn Gly Leu Thr Leu Leu Ile Leu Ala Leu Ile Ser Leu Phe
1105                1110                1115                1120
Ser Ile Pro Val Ile Tyr Glu Arg His Gln Val Gln Ile Asp His Tyr
            1125                1130                1135
Leu Gly Leu Ala Asn Lys Ser Val Lys Asp Ala Met Ala Lys Ile Gln
            1140                1145                1150
Ala Lys Ile Pro Gly Leu Lys Arg Lys Ala Asp
            1155                1160
```

<210> SEQ ID NO 31
<211> LENGTH: 1568
<212> TYPE: DNA
<213> ORGANISM: Rattus sp.

<400> SEQUENCE: 31

```
caggcttagt ctggggaagc gggtgtttca tgtctcaggg agaattttgc agtttacagc    60
gtttctgttg gtatgcataa tttgtaattg ctgctggagg gcagatcgtg gcaagaaatg   120
gacggacaga agaaacattg gaaggacaag gttgttgacc tcctctactg gagagacatt   180
aagaagactg gagtggtgtt tggtgccagc ttattcctgc tgctgtctct gacagtgttc   240
agcattgtca gtgtaacggc ctacattgcc ttggccctgc tctcggtgac tatcagcttt   300
aggatatata agggcgtgat ccaggctatc cagaaatcag atgaaggcca cccattcagg   360
gcatatttag aatctgaagt tgctatatca gaggaattgg ttcagaaata cagtaattct   420
gctcttggtc atgtgaacag cacaataaaa gaactgaggc ggcttttctt agttgatgat   480
ttagttgatt ccctgaagtt tgcagtgttg atgtgggtgt ttacttatgt tggtgccttg   540
ttcaatggtc tgacactact gattttagct ctgatctcac tcttcagtat tcctgttatt   600
tatgaacggc atcaggtgca gatagatcat tatctaggac ttgcaaacaa gagtgttaag   660
gatgccatgg ccaaaatcca agcaaaaatc cctggattga gcgcaaagc agattgaaaa   720
agccccaaac agaagttcat ctttaaaggg gacactcact tgattacggg ggtgggaggt   780
caggggtgag cccttggtgg ccgtgcggtt tcagctcttt atttttagca gtgcactgtt   840
tgaggaaaaa ttacctgtct tgacttcctg tgtttatcat cttaagtatt gtaagctgct   900
gtgtatggat ctcattgtag tcacacttgt cttccccaat gaggcgcctg gtgaataaag   960
```

```
gactcgggga aagctgtgca ttgtatctgc tgcagggtag tctagctgta tgcagagagt    1020
tgtaaagaag gcaaatctgg gggcagggaa aacccttttc acagtgtact gtgtttggtc    1080
agtgtaaaac tgatgcagat ttttctgaaa tgaaatgttt agatgagagc atactactaa    1140
agcagagtgg aaaactctgt ctttatggtg tgttctaggt gtattgtgaa tttactgtta    1200
tattgccaat ataagtaaat atagacctaa tctatatata gtgtttcaca aagcttagat    1260
ctttaacctt gcagctgccc cacagtgctt gacctctgag tcattggtta tgcagtgtag    1320
tcccaagcac ataaactagg aagagaaatg tatttgtagg agtgctacct accacctgtt    1380
ttcaagaaaa tatagaactc aacaaaaat atagaatgtc atttcaaaga cttactgtat     1440
gtatagttaa ttttgtcaca gactctgaaa ttctatggac tgaatttcat gcttccaaat    1500
gtttgcagtt atcaaacatt gttatgcaag aaatcataaa atgaagactt ataccattgt    1560
ggtttaag                                                              1568
```

<210> SEQ ID NO 32
<211> LENGTH: 141
<212> TYPE: PRT
<213> ORGANISM: Rattus sp.

<400> SEQUENCE: 32

```
Gln Ala Ser Gly Glu Ala Gly Val Ser Cys Leu Arg Glu Asn Phe Ala
 1               5                  10                  15

Val Tyr Ser Val Ser Val Gly Met His Asn Leu Leu Leu Leu Glu Gly
                20                  25                  30

Arg Ser Trp Gln Glu Met Asp Gly Gln Lys Lys His Trp Lys Asp Lys
            35                  40                  45

Val Val Asp Leu Leu Tyr Trp Arg Asp Ile Lys Lys Thr Gly Val Val
        50                  55                  60

Phe Gly Ala Ser Leu Phe Leu Leu Leu Ser Leu Thr Val Phe Ser Ile
 65                  70                  75                  80

Val Ser Val Thr Ala Tyr Ile Ala Leu Ala Leu Leu Ser Val Thr Ile
                 85                  90                  95

Ser Phe Arg Ile Tyr Lys Gly Val Ile Gln Ala Ile Ala Lys Ser Asp
                100                 105                 110

Glu Gly His Pro Phe Arg Ala Tyr Leu Glu Ser Glu Val Ala Ile Ser
            115                 120                 125

Glu Glu Leu Val Gln Lys Tyr Ser Asn Ser Ala Leu Gly
        130                 135                 140
```

<210> SEQ ID NO 33
<211> LENGTH: 18
<212> TYPE: PRT
<213> ORGANISM: Bos sp.

<400> SEQUENCE: 33

```
Ser Tyr Asp Ser Ile Lys Leu Glu Pro Glu Asn Pro Pro Tyr Glu
 1               5                  10                  15

Glu Ala
```

<210> SEQ ID NO 34
<211> LENGTH: 13
<212> TYPE: DNA
<213> ORGANISM: Homo sapiens

<400> SEQUENCE: 34

```
gccgccrcca tgg                                                          13
```

<210> SEQ ID NO 35
<211> LENGTH: 248
<212> TYPE: DNA
<213> ORGANISM: Homo sapiens
<220> FEATURE:
<221> NAME/KEY: misc_feature
<222> LOCATION: (1)...(248) at all n positions
<223> OTHER INFORMATION: n=a, c, g or t

<400> SEQUENCE: 35

| | | |
|---|---|---|
| gagccgtcac cacagtaggt ccctcggctc agtcggccca gccctctca gtcctcccca | 60 |
| acccccacaa ccgcccgcgc tcctgagacg cgccccggcg gcggcggcan agctgcagca | 120 |
| tcatctccac cctccagcca tggaagacct ggaccagtct cctctggtct cgtcctcgga | 180 |
| cagcccaccc cggccgcagc ccgcgttcaa gtaccagttc gtgagggagc ccgaggacga | 240 |
| ggaggaag | 248 |

<210> SEQ ID NO 36
<211> LENGTH: 379
<212> TYPE: DNA
<213> ORGANISM: Homo sapiens
<220> FEATURE:
<221> NAME/KEY: misc_feature
<222> LOCATION: (1)...(36) at all n positions
<223> OTHER INFORMATION: n=a, c, g or t

<400> SEQUENCE: 36

| | | |
|---|---|---|
| gaaaatatgg acttgaagga gcagccaggt aacactattt cggctggtca agaggatttc | 60 |
| ccatctgtcc tgcttgaaac tgctgcttct nttccttctc tgtctcctct ctcagccgct | 120 |
| tctttcaaag aacatgaata ccttggtaat ttgtcaacag tattacccac tgaaggaaca | 180 |
| cttcaagaaa atgtcagtga agcttctaaa gaggtctcag agaaggcaaa aactctactc | 240 |
| atagatagag atttaacaga gttttcagaa ttaggaatac tcagaaatgg gatcatcgtt | 300 |
| cagtgtctct ccaaaagcag aatctgccgt aaatagtagg caaatcctag gggaagaaat | 360 |
| aattcgtgga aaaataaag | 379 |

<210> SEQ ID NO 37
<211> LENGTH: 281
<212> TYPE: DNA
<213> ORGANISM: Homo sapiens
<220> FEATURE:
<221> NAME/KEY: misc_feature
<222> LOCATION: (1)...(281) at all n positions
<223> OTHER INFORMATION: n=a, c, g or t

<400> SEQUENCE: 37

| | | |
|---|---|---|
| gatagagatt taacagagtt ttcagaatta gaatactcag aaatgggatc atcgttcagt | 60 |
| gtctctccaa aagcagaatc tgccgtaata gtagcaaatc ctagggaaga aataatcgtg | 120 |
| aaaaataaag atgaagaaga gaagttagtt agtaataaca tccttcatan tcaacaagag | 180 |
| ttacctacag ctcttactaa attggttaaa gaggatgaag ttgtgtcttc agaaaaagca | 240 |
| aaagacagtt ttatgaaaga gagttgcagt ggaantccctt g | 281 |

<210> SEQ ID NO 38
<211> LENGTH: 640
<212> TYPE: DNA
<213> ORGANISM: Homo sapiens
<220> FEATURE:
<221> NAME/KEY: misc_feature
<222> LOCATION: (1)...(640) at all n positions
<223> OTHER INFORMATION: n=a, c, g or t

```
<400> SEQUENCE: 38
ttaaagagga tgaagttgtg tcttcagaaa aagcaaaaga cagttttaat gaaaagagag        60
ttgcagtgga agctcctatg agggaggaat atgcagactt caaaccattt gagcgagtat       120
gggaagtgaa agatagtaag gaagatagtg atatgttggc tgctggaggt aaaatcgaga       180
gcaacttgga agtaaagtg gataaaaaat gttttgcaga tagccttgag caaactaatc       240 acgaaaaga tagtgagagt agtaatgatg atacttcttt ccccagtacg ccagaaggta       300
taaaggatcg ttcaggagca tatatcacat gtgctccctt taacccagca gcaactgaga      360
gcattgcaac naacattttt cctttgttgg agatcctact tcagaaaatt agaccgtgaa      420
aaaaaataga agaaaagaag gccnaatgtt accgagaaga atactagcac aaanctcaac      480
cctttcttgt gcagcacagg ntctgngaca gatatgtccc acgnttatta ccaagtgctg      540
agantcttgc aacatcctga ngctgactcc gattgttccn gagctttgaa tggattgtgg      600
ttctggtcaa gttntttgan caaatggctt gtcactcgat                            640

<210> SEQ ID NO 39
<211> LENGTH: 346
<212> TYPE: DNA
<213> ORGANISM: Homo sapiens
<220> FEATURE:
<221> NAME/KEY: misc_feature
<222> LOCATION: (1)...(346) at all n positions
<223> OTHER INFORMATION: n=a, c, g or t

<400> SEQUENCE: 39
ctgtgcccgg ccccaccccc tgggcagatg tcccccactg ctaaggctgc tggcttcagg       60
gagggttagc ctgcaccgcc gccaccctgc ccctaagtta ttacctctcc agttcctacc      120
gtactccctg caccgtctca ctgtgtgtnt cgtgtcagta atttatatgg tgttaaaatg      180
tgtatatttt tgtatgtnac tatttnact agggctgagg ggcctgcgcc cagagctggc      240
ctcccncaac acctgctgcg cttggtaggt gtggtggcgt tatggcagcc cggctgctgc     300
ttggatgcga gnttggnctt gggccggtgc tggggggcac agttgt                    346

<210> SEQ ID NO 40
<211> LENGTH: 325
<212> TYPE: DNA
<213> ORGANISM: Homo sapiens

<400> SEQUENCE: 40
gtggcaaaca tgcctgaagg cctgactcca gatttagtac aggaagcatg tgaaagtgaa       60
ttgaatgaag ttactggtac aaagattgct tatgaaacaa aatggacttg gttcaaacat      120
cagaagttat gcaagagtca ctctatcctg cagcacagct ttgcccatca tttgaagagt      180
cagaagctac tccttcacca gttttgcctg acattgttat ggaagcacca ttgaattctg      240
cagttcctag tgctggtgct tccgtgatac agcccagctc atcaccatta gaggcttctt      300
cagttaatta tgaagcataa acatg                                            325

<210> SEQ ID NO 41
<211> LENGTH: 338
<212> TYPE: DNA
<213> ORGANISM: Homo sapiens

<400> SEQUENCE: 41
gcatgtgaaa gtgaattgaa tgaagttact ggtacaaaga ttgcttatga aacaaaaatg       60
gacttggttc aaacatcaga agttatgcaa gagtcactct atcctgcagc acagctttgc      120
```

```
ccatcatttg aagagtcaga agctactcct tcaccagttt tgcctgacat tgttatggaa      180
gcaccattga attctgcagt tcctagtgct ggtgcttccg tgatacagcc cagctcatca      240
ccattagaag cttcttcagt taattatgaa agcataaaac atgagcctga aaaccccca      300 ccatatgaag aggccatgag tgtatcacta aaaaaagt                              338

<210> SEQ ID NO 42
<211> LENGTH: 480
<212> TYPE: DNA
<213> ORGANISM: Homo sapiens
<220> FEATURE:
<221> NAME/KEY: misc_feature
<222> LOCATION: (1)... (480) at all n positions
<223> OTHER INFORMATION: n=a, c, g or t

<400> SEQUENCE: 42
aagactggag tggtgtttgg tgccagccta ttcctgctgc tttcattgac agtattcagc       60
attgtgagcg taacagccta cattgccttg ccctgctct ctgtgaccat cagctttagg      120
atatacaagg gtgtgatcca agctatccag aaatcagatg aaggccaccc attcagggca     180
tatctggaat ctgaagttgc tatatctgag gagttggttc agaagtacag taattctgct     240
cttggtcatg tgaactgcac gataaaggaa ctcaggcgcc tcttcttagt tgatgattta    300
gttgattctc tgaagtttgc agtgttgatg tgggtattta cctatgttgg tgccttgttt     360
aatggtctga cactactgat ttnggctctc attccactcc tncaagtgtt cctggtattt     420
ntgaacggca tcnggcacag ntagatcatt atccaggact tgcaataggg aatgtaaaga    480

<210> SEQ ID NO 43
<211> LENGTH: 13
<212> TYPE: PRT
<213> ORGANISM: Homo sapiens

<400> SEQUENCE: 43

Met Glu Asp Leu Asp Gln Ser Pro Leu Val Ser Ser Ser
  1               5                  10

<210> SEQ ID NO 44
<211> LENGTH: 16
<212> TYPE: PRT
<213> ORGANISM: Homo sapiens

<400> SEQUENCE: 44

Lys Ile Met Asp Leu Lys Glu Gln Pro Gly Asn Thr Ile Ser Ala Gly
  1               5                  10                  15

<210> SEQ ID NO 45
<211> LENGTH: 19
<212> TYPE: PRT
<213> ORGANISM: Homo sapiens

<400> SEQUENCE: 45

Lys Glu Asp Glu Val Val Ser Ser Glu Lys Ala Lys Asp Ser Phe Asn
  1               5                  10                  15

Glu Lys Arg

<210> SEQ ID NO 46
<211> LENGTH: 50
<212> TYPE: PRT
<213> ORGANISM: Homo sapiens
```

-continued

```
<400> SEQUENCE: 46

Gln Glu Ser Leu Tyr Pro Ala Ala Gln Leu Cys Pro Ser Phe Glu Glu
 1               5                  10                  15

Ser Glu Ala Thr Pro Ser Pro Val Leu Pro Asp Ile Val Met Glu Ala
            20                  25                  30

Pro Leu Asn Ser Ala Val Pro Ser Ala Gly Ala Ser Val Ile Gln Pro
        35                  40                  45

Ser Ser
   50

<210> SEQ ID NO 47
<211> LENGTH: 26
<212> TYPE: DNA
<213> ORGANISM: Artificial Sequence
<220> FEATURE:
<223> OTHER INFORMATION: degenerate oligonucleotides designed from the
      bovine NI220 peptide 1 sequence
<220> FEATURE:
<221> NAME/KEY: modified_base
<222> LOCATION: (1)...(26) at all n positions
<223> OTHER INFORMATION: n=inosine

<400> SEQUENCE: 47
tcngtnggya anacngcngg yaartc                                            26

<210> SEQ ID NO 48
<211> LENGTH: 23
<212> TYPE: DNA
<213> ORGANISM: Artificial Sequence
<220> FEATURE:
<223> OTHER INFORMATION: degenerate oligonucleotides designed from the
      bovine NI220 peptide 1 sequence
<220> FEATURE:
<221> NAME/KEY: modified_base
<222> LOCATION: (1)...(23) at all n positions
<223> OTHER INFORMATION: n=inosine

<400> SEQUENCE: 48
tcngtnggna gnacnggyaa ytc                                               23

<210> SEQ ID NO 49
<211> LENGTH: 25
<212> TYPE: DNA
<213> ORGANISM: Artificial Sequence
<220> FEATURE:
<223> OTHER INFORMATION: degenerate oligonucleotides designed from the
      bovine NI220 peptide 1 sequence
<220> FEATURE:
<221> NAME/KEY: modified_base
<222> LOCATION: (1)...(25) at all n positions
<223> OTHER INFORMATION: n=inosine

<400> SEQUENCE: 49
tcngtnggya anacngcggn agrtc                                             25

<210> SEQ ID NO 50
<211> LENGTH: 26
<212> TYPE: DNA
<213> ORGANISM: Artificial Sequence
<220> FEATURE:
<223> OTHER INFORMATION: degenerate oligonucleotides designed from the
      bovine NI220 peptide 1 sequence
<220> FEATURE:
<221> NAME/KEY: modified_base
<222> LOCATION: (1)...(26) at all n positions
<223> OTHER INFORMATION: n=inosine
```

-continued

```
<400> SEQUENCE: 50
tcngtnggna gnacngcngg nagrtc                                          26

<210> SEQ ID NO 51
<211> LENGTH: 26
<212> TYPE: DNA
<213> ORGANISM: Artificial Sequence
<220> FEATURE:
<223> OTHER INFORMATION: degenerate oligonucleotides designed from the
      bovine NI220 peptide 2 sequence
<220> FEATURE:
<221> NAME/KEY: modified_base
<222> LOCATION: (1)...(26) at all n positions
<223> OTHER INFORMATION: n=inosine

<400> SEQUENCE: 51
garathgcng anathcarga yggnga                                          26
```